(12) United States Patent
Lee et al.

(10) Patent No.: US 11,007,267 B2
(45) Date of Patent: May 18, 2021

(54) ANTI-CD3 ANTIBODIES AND METHODS OF USE

(71) Applicant: Genentech, Inc., South San Francisco, CA (US)

(72) Inventors: Chingwei Vivian Lee, Foster City, CA (US); Mark S. Dennis, San Carlos, CA (US); Germaine Fuh, Pacifica, CA (US)

(73) Assignee: Genentech, Inc., South San Francisco, CA (US)

( * ) Notice: Subject to any disclaimer, the term of this patent is extended or adjusted under 35 U.S.C. 154(b) by 582 days.

(21) Appl. No.: 15/836,107

(22) Filed: Dec. 8, 2017

(65) Prior Publication Data

US 2018/0117152 A1 May 3, 2018

Related U.S. Application Data

(63) Continuation of application No. PCT/US2016/034992, filed on May 31, 2016.

(60) Provisional application No. 62/180,462, filed on Jun. 16, 2015.

(51) Int. Cl.
| | |
|---|---|
| *A61K 39/00* | (2006.01) |
| *A61K 39/395* | (2006.01) |
| *C07K 16/28* | (2006.01) |
| *C07K 16/30* | (2006.01) |
| *A61P 35/00* | (2006.01) |
| *C07K 14/725* | (2006.01) |

(52) U.S. Cl.
CPC ........ *A61K 39/39558* (2013.01); *A61P 35/00* (2018.01); *C07K 14/7051* (2013.01); *C07K 16/2809* (2013.01); *C07K 16/30* (2013.01); *A61K 2039/505* (2013.01); *C07K 2317/24* (2013.01); *C07K 2317/31* (2013.01); *C07K 2317/92* (2013.01)

(58) Field of Classification Search
CPC ............................................... A61K 2039/505
See application file for complete search history.

(56) References Cited

U.S. PATENT DOCUMENTS

| | | | |
|---|---|---|---|
| 5,821,337 A | 10/1998 | Carter et al. | |
| 7,612,181 B2 | 11/2009 | Wu et al. | |
| 7,951,546 B2 | 5/2011 | Frantz et al. | |
| 8,258,268 B2 | 9/2012 | Wu et al. | |
| 8,722,859 B2 | 5/2014 | Miller et al. | |
| 9,011,864 B2 | 4/2015 | Schulz et al. | |
| 10,501,545 B2 * | 12/2019 | Kelley | A61K 45/06 |
| 2012/0244577 A1 | 9/2012 | Dixit et al. | |
| 2013/0150558 A1 | 6/2013 | Williams et al. | |
| 2014/0170149 A1 | 6/2014 | Neijssen et al. | |
| 2014/0187753 A1 | 7/2014 | Blein et al. | |
| 2015/0133640 A1 | 5/2015 | Blein et al. | |
| 2015/0166661 A1 | 6/2015 | Chen et al. | |
| 2015/0266966 A1 | 9/2015 | Smith et al. | |
| 2015/0284475 A1 | 10/2015 | Zhou et al. | |
| 2016/0000916 A1 | 1/2016 | Crotts et al. | |
| 2016/0145339 A1 | 5/2016 | Zhou et al. | |
| 2017/0008971 A1 | 1/2017 | Dennis et al. | |
| 2017/0022274 A1 | 1/2017 | Chang et al. | |

FOREIGN PATENT DOCUMENTS

| | | |
|---|---|---|
| CN | 101675077 A | 3/2010 |
| EP | 1923072 A1 | 5/2008 |
| EP | 2482212 A1 | 8/2012 |
| EP | 2769989 A1 | 8/2014 |
| EP | 2789630 A1 | 10/2014 |
| EP | 2840091 A1 | 2/2015 |
| WO | WO-94/04679 A1 | 3/1994 |
| WO | WO-03/087131 A2 | 10/2003 |
| WO | WO-2004/106380 A2 | 12/2004 |
| WO | WO-2007/146968 A2 | 12/2007 |
| WO | WO-2008/119566 A2 | 10/2008 |
| WO | WO-2010/081173 A2 | 7/2010 |
| WO | WO-2010/114940 A1 | 10/2010 |
| WO | WO-2011/028952 A1 | 3/2011 |
| WO | WO-2011/090754 A1 | 7/2011 |
| WO | WO-2011/090762 A1 | 7/2011 |
| WO | WO-2011/143545 A1 | 11/2011 |
| WO | WO-2012/075581 A1 | 6/2012 |
| WO | WO-2012/123949 A1 | 9/2012 |
| WO | WO-2012/143524 A2 | 10/2012 |
| WO | WO-2012/162067 A2 | 11/2012 |
| WO | WO-2013128194 A1 | 9/2013 |
| WO | WO-2013/163631 A2 | 10/2013 |
| WO | WO-2013/192546 A1 | 12/2013 |
| WO | WO-2013/192550 A2 | 12/2013 |
| WO | WO-2014/012085 A2 | 1/2014 |
| WO | WO-2014/083178 A1 | 6/2014 |
| WO | WO-2014/108483 A1 | 7/2014 |
| WO | WO-2014/107599 A2 | 10/2014 |
| WO | WO-2014/170063 A1 | 10/2014 |
| WO | WO-2015/006749 A2 | 1/2015 |

(Continued)

OTHER PUBLICATIONS

Durben et al. (Mol. Ther. Apr. 2015; 23 (4): 648-55).*
Mallya et al. (Protein Sci. 2006; 15: 2244-56).*
Brack et al. "A Bispecific HER2-Targeting FynomAb with Superior Antitumor Activity and Novel Mode of Action," Mol Cancer Ther. 13(8): 2030-39 (2014) (11 pages).
Brinkmann et al. "The making of bispecific anitbodies," MAbs. 9(2): 182-212 (2017).
Buhmann et al. "Immunotherapy of recurrent B-cell malignancies after allo-SCT with Bi20 (FBTA05), a trifunctional anti-CD3 x anti-CD20 antibody and donor lymphocyte infusion," Bone Marrow Transplant. 43(5):383-97 (2009).

(Continued)

*Primary Examiner* — Stephen L Rawlings
(74) *Attorney, Agent, or Firm* — Clark & Elbing LLP; Karen L. Elbing

(57) ABSTRACT

The invention provides anti-cluster of differentiation 3 (CD3) antibodies and methods of using the same.

27 Claims, 3 Drawing Sheets

Specification includes a Sequence Listing.

(56) References Cited

FOREIGN PATENT DOCUMENTS

| WO | WO-2015/013671 A1 | 1/2015 |
|----|---|---|
| WO | WO-2015/018527 A1 | 2/2015 |
| WO | WO-2015/143079 A1 | 9/2015 |
| WO | WO-2015/184203 A1 | 12/2015 |
| WO | WO-2015/184207 A1 | 12/2015 |
| WO | WO-2016/014942 A1 | 1/2016 |
| WO | WO-2016/019969 A1 | 2/2016 |
| WO | WO-2016/081490 A1 | 5/2016 |
| WO | WO-2016110576 A1 | 7/2016 |
| WO | WO-2016/201300 A1 | 12/2016 |

OTHER PUBLICATIONS

Choi et al. "Bispecific antibodies engage T cells for antitumor immunotherapy," Expert Opin Biol Ther. 11(7): 843-53 (2011).
Desnoyers et al."Tumor-Specific Activation of an EGFR-Targeting Probody Enhances Therapeutic Index," Sci. Transl. Med. 5(207):207ra144 (2013) (10 pages).
Diefenbach et al., "An individualized risk mitigation approach for safety: experience from the mosunetuzumab (CD20/CD3 bispecific antibody) development program in relation to neurotoxicity risk," 61st Ash Annual Meeting & Exposition 10 (2019).
Drent et al. "A Rational Strategy for Reducing On-Target Off-Tumor Effects of CD38-Chimeric Antigen Receptors by Affinity Optimization," Mol Ther. 25(8): 1946-58 (2017).
Hosseini et al., "Abstract B043: Systems pharmacology modeling of anti-CD20/CD3 T-cell dependent bispecific antibody and its application to clinical trial design," Proceedings of the Second CRI-CIMT-EATI-AACR International Cancer Immunotherapy Conference: Translating Science into Survival; Sep. 25-28; New York, NY. Cancer Immunol Res. 4(11 Suppl):Abstract nr B043 (2016) (4 pages).
Huang et al. "In Vivo Deamidation Characterization of Monoclonal Antibody by LC/MS/MS," Anal Chem. 77(5): 1432-9 (2005).
Igawa et al. "VH/VL interface engineering to promote selective expression and inhibit conformational isomerization of thrombopoietin receptor agonist single-chain diabody," Protein Eng Des Sel. 23(8):667-77 (2010) (11 pages).
Kelley et al. "Thermodynamic Analysis of an Antibody Functional Epitope," Biochemistry. 32(27): 6828-35 (1993).
Kiewe et al. "Phase I trial of the trifunctional anti-HER2 x anti-CD3 antibody ertumaxomab in metastatic breast cancer," 2005 ASCO Annual Meeting Proceedings. J Clin Oncol. 23(16S):Abstract 2530 (2005).
Kortt et al. "Dimeric and trimeric antibodies: high avidity scFvs for cancer targeting," Biomol Eng. 18:95-108 (2001) (15 pages).
Lee et al. "Current concepts in the diagnosis and management of cytokine release syndrome," retrieved from <www.ncbi.nlm.nih.gov/pmc/articles/PMC4093680/?report=printable> on Feb. 19, 2020, Blood 124(2):188-95 (2014) (18 pages).
Li et al. "Exposure-response analyses indicate a promising benefit/risk profile of mosunetuzumab in relapsed and refractory non-Hodgkin lymphoma," 61st Ash Annual Meeting & Exposition (2019).
Liu et al. "Affinity-Tuned ErbB2 or EGFR Chimeric Antigen Receptor T Cells Exhibit an Increased Therapeutic Index against Tumors in Mice," Cancer Res. 75(17): 3596-607 (2015) (13 pages).
Liu et al. "Heteroantibody duplexes target cells for lysis by cytotoxic T lymphocytes," Proc Natl Acad Sci U S A. 82(24):8648-52 (1985).
Milner et al. "Differential responses of invariant V alpha 24J alpha Q T cells and MHC class II-restricted CD4+ T cells to dexamethasone," J Immunol. 163(5):2522-9 (1999).
Nishimoto et al., "Toxicity, pharmacokinetics, and dose-finding study of repetitive treatment with the humanized anti-interleukin 6 receptor antibody MRA in rheumatoid arthritis. Phase I/II clinical study," J Rheumatol. 30(7):1426-35 (2003).
Roosnek et al. "Triggering T Cells by Otherwise Inert Hybrid Anti-CD3/Antitumor Antibodies Requires Encounter with the Specific Target Cell," J Exp Med. 170(1):297-302 (1989) (6 pages).
Seung et al., "Immunotherapy with long-lived anti-CD20 x anti-CD3 bispecific antibodies stimulates potent t cell-mediated killing of human b cell lines and of circuating and lymphoid b cells in monkeys: a potential therapy for b cell lymphomas and leukemias," Blood. 124(21):311 (2014).
Spiess et al. "Alternative molecular formats and therapeutic applications for bispecific antibodies," Mol immunol. 67:95-106 (2015).
Sun et al. "Anti-CD20/CD3 T cell-dependent bispecific antibody for the treatment of B cell malignancies," Sci Transl Med. 7(287):287ra70 (2015) (11 pages).
Weidle et al. "The Intriguing Options of Multispecific Antibody Formats for Treatment of Cancer," Cancer Genomics & Proteomics. 10:1-18 (2013) (18 pages).
Wuellner et al. "Bispecific CD3/HER2 Targeting FynomAb Induces Redirected T Cell-Mediated Cytolysis with High Potency and Enhanced Tumor Selectivity," Antibodies. 4(4): 426-440 (2015) (15 pages).
Yan et al., "Succinimide Formation at Asn 55 in the Complementarity Determining Region of a Recombinant Monoclonal Antibody IgG1 Heavy Chain," J Pharm Sci. 98(10): 3509-21 (2009).
Zhu et al. "Engineering high affinity humanized anti-p185HER2/anti-CD3 bispecific F(ab')2 for efficient lysis of p185HER2 overexpressing tumor cells," Int J Cancer. 62(3):319-24 (1995).
Wu et al., "Humanization of a murine monoclonal antibody by simultaneous optimization of framework and CDR residues," J Mol Biol. 294(1):151-62 (1999).
Communication pursuant to Article 94(3) EPC for European Patent Application No. 16728531.1, dated Jul. 16, 2019 (10 pages).
Chatenoud et al., "CD3-specific antibodies: a portal to the treatment of autoimmunity," Nat Rev Immunol. 7(8):622-32 (2007).
Huehls et al., "Bispecific T-cell engagers for cancer immunotherapy," Immunol Cell Biol. 93(3):290-6 (2015).
Lum et al., "Targeting T cells with bispecific antibodies for cancer therapy," available in PMC Oct. 8, 2013, published in final edited form as: BioDrugs. 25(6):365-79 (2011) (24 pages).
Reusch et al., "A tetravalent bispecific TandAb (CD19/CD3), AFM11, efficiently recruits T cells for the potent lysis of CD19(+) tumor cells," MAbs. 7(3):584-604 (2015) (22 pages).
Wark et al., "Latest technologies for the enhancement of antibody affinity," Adv Drug Deliv Rev. 58(5-6):657-70 (2006).
International Preliminary Report on Patentability for International Patent Application No. PCT/US2016/034992, dated Dec. 19, 2017 (10 pages).
International Search Report and Written Opinion for International Patent Application No. PCT/US2016/034992, dated Oct. 4, 2016 (19 pages).
Anderson, et al "G19.4(alpha CD3) x B43(alpha CD19) monoclonal antibody heteroconjugate triggers CD19 antigen-specific lysis of t(4;11) acute lymphoblastic leukemia cells by activated CD3 antigen-positive cytotoxic T cells," Blood. Dec. 1, 1992;80(11):2826-34.
Baeuerle et al., "Bispecific T-cell engaging antibodies for cancer therapy," Cancer Res. 69(12):4941-4. (2009) doi: 10.1158/0008-5472.CAN-09-0547.
Bortoletto et al., "Optimizing anti-CD3 affinity for effective T cell targeting against tumor cells" Eur J Immunol. 32(11):3102-7 (2002).
Che-Leung Law et al., "Expression and characterization of recombinant soluble human CD3 molecules: presentation of antigenic epitopes defined on the native TCR-CD3 complex," Int Immunol. 14(4):389-400 (2002).
Lippow et al., "Computational design of antibody-affinity improvement beyond in vivo maturation," Nat Biotechnol. 25(10):1171-6 (2007).

* cited by examiner

Light chain variable domain (VL) of 38E4v11

| Kabat number | 1 2 3 4 5 6 7 8 9 10 11 12 13 14 15 16 17 18 19 20 21 22 23 24 25 26 27 a b c d e f 28 29 30 31 32 33 34 35 36 |
|---|---|
| 38E4v11 | D I V M T Q S P D S L A V S L G E R A T I N C K S S Q S L L N S R T R K N Y L A W Y |

HVR-L1 (SEQ ID NO: 4)

| Kabat number | 37 38 39 40 41 42 43 44 45 46 47 48 49 50 51 52 53 54 55 56 57 58 59 60 61 62 63 64 65 66 67 68 69 70 71 |
|---|---|
| 38E4v11 | Q Q K P G Q S P K L L I Y W T S T R . . . K S G V P D R F S G S G S G T D F |

HVR-L2 (SEQ ID NO: 5)

| Kabat number | 72 73 74 75 76 77 78 79 80 81 82 83 84 85 86 87 88 89 90 91 92 93 94 95 96 97 98 99 100 101 102 103 104 105 106 107 |
|---|---|
| 38E4v11 | T L T I S S L Q A E D V A V Y Y C T Q S F I L . . . . R T F G Q G T K V E I K |

HVR-L3 (SEQ ID NO: 6)    SEQ ID NO: 8

B

Heavy chain variable domain (VH) of 38E4v11

| Kabat number | 1 2 3 4 5 6 7 8 9 10 11 12 13 14 15 16 17 18 19 20 21 22 23 24 25 26 27 28 29 30 31 32 33 34 35 36 37 38 39 40 41 42 43 44 |
|---|---|
| 38E4v11 | E V Q L V Q S G A E V K K P G A S V K V S C K A S G F T F T S Y Y I H . . W V R Q A P G Q G |

HVR-H1 (SEQ ID NO: 1)

| Kabat number | 45 46 47 48 49 50 51 52 a 53 54 55 56 57 58 59 60 61 62 63 64 65 66 67 68 69 70 71 72 73 74 75 76 77 78 79 80 81 82 a b c 83 84 |
|---|---|
| 38E4v11 | L E W I G W I Y P . . E N D N T K Y N E K F K D R V T I T A D T S T S T A Y L E L S S L R S |

HVR-H2 (SEQ ID NO: 2)

| Kabat number | 85 86 87 88 89 90 91 92 93 94 95 96 97 98 99 100 a 101 102 103 104 105 106 107 108 109 110 111 112 113 |
|---|---|
| 38E4v11 | E D T A V Y Y C A R D G Y S R Y Y . . . . . F D Y W G Q G T L V T V S S |

HVR-H3 (SEQ ID NO: 3)    SEQ ID NO: 7

```
                              SEQUENCE LISTING

<160> NUMBER OF SEQ ID NOS: 79

<210> SEQ ID NO 1
<211> LENGTH: 5
<212> TYPE: PRT
<213> ORGANISM: Artificial Sequence
<220> FEATURE:
<223> OTHER INFORMATION: Synthetic Construct

<400> SEQUENCE: 1

Ser Tyr Tyr Ile His
1               5

<210> SEQ ID NO 2
<211> LENGTH: 17
<212> TYPE: PRT
<213> ORGANISM: Artificial Sequence
<220> FEATURE:
<223> OTHER INFORMATION: Synthetic Construct

<400> SEQUENCE: 2

Trp Ile Tyr Pro Glu Asn Asp Asn Thr Lys Tyr Asn Glu Lys Phe Lys
1               5                   10                  15

Asp

<210> SEQ ID NO 3
<211> LENGTH: 10
<212> TYPE: PRT
<213> ORGANISM: Artificial Sequence
<220> FEATURE:
<223> OTHER INFORMATION: Synthetic Construct

<400> SEQUENCE: 3

Asp Gly Tyr Ser Arg Tyr Tyr Phe Asp Tyr
1               5                   10

<210> SEQ ID NO 4
<211> LENGTH: 17
<212> TYPE: PRT
<213> ORGANISM: Artificial Sequence
<220> FEATURE:
<223> OTHER INFORMATION: Synthetic Construct

<400> SEQUENCE: 4

Lys Ser Ser Gln Ser Leu Leu Asn Ser Arg Thr Arg Lys Asn Tyr Leu
1               5                   10                  15

Ala

<210> SEQ ID NO 5
<211> LENGTH: 7
<212> TYPE: PRT
<213> ORGANISM: Artificial Sequence
<220> FEATURE:
<223> OTHER INFORMATION: Synthetic Construct

<400> SEQUENCE: 5

Trp Thr Ser Thr Arg Lys Ser
1               5
```

```
<210> SEQ ID NO 6
<211> LENGTH: 8
<212> TYPE: PRT
<213> ORGANISM: Artificial Sequence
<220> FEATURE:
<223> OTHER INFORMATION: Synthetic Construct

<400> SEQUENCE: 6

Thr Gln Ser Phe Ile Leu Arg Thr
1               5

<210> SEQ ID NO 7
<211> LENGTH: 119
<212> TYPE: PRT
<213> ORGANISM: Artificial Sequence
<220> FEATURE:
<223> OTHER INFORMATION: Synthetic Construct

<400> SEQUENCE: 7

Glu Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Thr Ser Tyr
            20                  25                  30

Tyr Ile His Trp Val Arg Gln Ala Pro Gly Gln Gly Leu Glu Trp Ile
        35                  40                  45

Gly Trp Ile Tyr Pro Glu Asn Asp Asn Thr Lys Tyr Asn Glu Lys Phe
    50                  55                  60

Lys Asp Arg Val Thr Ile Thr Ala Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Asp Gly Tyr Ser Arg Tyr Tyr Phe Asp Tyr Trp Gly Gln Gly
            100                 105                 110

Thr Leu Val Thr Val Ser Ser
        115

<210> SEQ ID NO 8
<211> LENGTH: 112
<212> TYPE: PRT
<213> ORGANISM: Artificial Sequence
<220> FEATURE:
<223> OTHER INFORMATION: Synthetic Construct

<400> SEQUENCE: 8

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Ser Pro Lys Leu Leu Ile Tyr Trp Thr Ser Thr Arg Lys Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Thr Gln
                85                  90                  95

Ser Phe Ile Leu Arg Thr Phe Gly Gln Gly Thr Lys Val Glu Ile Lys
            100                 105                 110

<210> SEQ ID NO 9
```

<211> LENGTH: 30
<212> TYPE: PRT
<213> ORGANISM: Artificial Sequence
<220> FEATURE:
<223> OTHER INFORMATION: Synthetic Construct

<400> SEQUENCE: 9

Glu Val Gln Leu Val Gln Ser Gly Ala Glu Val Lys Lys Pro Gly Ala
1               5                   10                  15
Ser Val Lys Val Ser Cys Lys Ala Ser Gly Phe Thr Phe Thr
            20                  25                  30

<210> SEQ ID NO 10
<211> LENGTH: 14
<212> TYPE: PRT
<213> ORGANISM: Artificial Sequence
<220> FEATURE:
<223> OTHER INFORMATION: Synthetic Construct

<400> SEQUENCE: 10

Trp Val Arg Gln Ala Pro Gly Gln Gly Leu Glu Trp Ile Gly
1               5                   10

<210> SEQ ID NO 11
<211> LENGTH: 32
<212> TYPE: PRT
<213> ORGANISM: Artificial Sequence
<220> FEATURE:
<223> OTHER INFORMATION: Synthetic Construct

<400> SEQUENCE: 11

Arg Val Thr Ile Thr Ala Asp Thr Ser Thr Ser Thr Ala Tyr Leu Glu
1               5                   10                  15
Leu Ser Ser Leu Arg Ser Glu Asp Thr Ala Val Tyr Tyr Cys Ala Arg
            20                  25                  30

<210> SEQ ID NO 12
<211> LENGTH: 11
<212> TYPE: PRT
<213> ORGANISM: Artificial Sequence
<220> FEATURE:
<223> OTHER INFORMATION: Synthetic Construct

<400> SEQUENCE: 12

Trp Gly Gln Gly Thr Leu Val Thr Val Ser Ser
1               5                   10

<210> SEQ ID NO 13
<211> LENGTH: 23
<212> TYPE: PRT
<213> ORGANISM: Artificial Sequence
<220> FEATURE:
<223> OTHER INFORMATION: Synthetic Construct

<400> SEQUENCE: 13

Asp Ile Val Met Thr Gln Ser Pro Asp Ser Leu Ala Val Ser Leu Gly
1               5                   10                  15
Glu Arg Ala Thr Ile Asn Cys
            20

<210> SEQ ID NO 14
<211> LENGTH: 15
<212> TYPE: PRT
<213> ORGANISM: Artificial Sequence
<220> FEATURE:
<223> OTHER INFORMATION: Synthetic Construct

<400> SEQUENCE: 14

Trp Tyr Gln Gln Lys Pro Gly Gln Ser Pro Lys Leu Leu Ile Tyr
1               5                   10                  15

<210> SEQ ID NO 15
<211> LENGTH: 32
<212> TYPE: PRT
<213> ORGANISM: Artificial Sequence
<220> FEATURE:
<223> OTHER INFORMATION: Synthetic Construct

<400> SEQUENCE: 15

Gly Val Pro Asp Arg Phe Ser Gly Ser Gly Ser Gly Thr Asp Phe Thr
1               5                   10                  15

Leu Thr Ile Ser Ser Leu Gln Ala Glu Asp Val Ala Val Tyr Tyr Cys
            20                  25                  30

<210> SEQ ID NO 16
<211> LENGTH: 10
<212> TYPE: PRT
<213> ORGANISM: Artificial Sequence
<220> FEATURE:
<223> OTHER INFORMATION: Synthetic Construct

<400> SEQUENCE: 16

Phe Gly Gln Gly Thr Lys Val Glu Ile Lys
1               5                   10

<210> SEQ ID NO 17
<211> LENGTH: 10
<212> TYPE: PRT
<213> ORGANISM: Artificial Sequence
<220> FEATURE:
<223> OTHER INFORMATION: Synthetic Construct

<400> SEQUENCE: 17

Gly Tyr Thr Phe Thr Ser Tyr Asn Met His
1               5                   10

<210> SEQ ID NO 18
<211> LENGTH: 17
<212> TYPE: PRT
<213> ORGANISM: Artificial Sequence
<220> FEATURE:
<223> OTHER INFORMATION: Synthetic Construct

<400> SEQUENCE: 18

Ala Ile Tyr Pro Gly Asn Gly Asp Thr Ser Tyr Asn Gln Lys Phe Lys
1               5                   10                  15

Gly

<210> SEQ ID NO 19
<211> LENGTH: 13
<212> TYPE: PRT
<213> ORGANISM: Artificial Sequence
<220> FEATURE:
<223> OTHER INFORMATION: Synthetic Construct

<400> SEQUENCE: 19

Val Val Tyr Tyr Ser Asn Ser Tyr Trp Tyr Phe Asp Val
1               5                   10

<210> SEQ ID NO 20
<211> LENGTH: 10

```
<212> TYPE: PRT
<213> ORGANISM: Artificial Sequence
<220> FEATURE:
<223> OTHER INFORMATION: Synthetic Construct

<400> SEQUENCE: 20

Arg Ala Ser Ser Ser Val Ser Tyr Met His
1               5                   10

<210> SEQ ID NO 21
<211> LENGTH: 7
<212> TYPE: PRT
<213> ORGANISM: Artificial Sequence
<220> FEATURE:
<223> OTHER INFORMATION: Synthetic Construct

<400> SEQUENCE: 21

Ala Pro Ser Asn Leu Ala Ser
1               5

<210> SEQ ID NO 22
<211> LENGTH: 9
<212> TYPE: PRT
<213> ORGANISM: Artificial Sequence
<220> FEATURE:
<223> OTHER INFORMATION: Synthetic Construct

<400> SEQUENCE: 22

Gln Gln Trp Ser Phe Asn Pro Pro Thr
1               5

<210> SEQ ID NO 23
<211> LENGTH: 25
<212> TYPE: PRT
<213> ORGANISM: Artificial Sequence
<220> FEATURE:
<223> OTHER INFORMATION: Synthetic Construct

<400> SEQUENCE: 23

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 24
<211> LENGTH: 14
<212> TYPE: PRT
<213> ORGANISM: Artificial Sequence
<220> FEATURE:
<223> OTHER INFORMATION: Synthetic Construct

<400> SEQUENCE: 24

Trp Val Arg Gln Ala Pro Gly Lys Gly Leu Glu Trp Val Gly
1               5                   10

<210> SEQ ID NO 25
<211> LENGTH: 32
<212> TYPE: PRT
<213> ORGANISM: Artificial Sequence
<220> FEATURE:
<223> OTHER INFORMATION: Synthetic Construct

<400> SEQUENCE: 25

Arg Phe Thr Ile Ser Val Asp Lys Ser Lys Asn Thr Leu Tyr Leu Gln
1               5                   10                  15

Met Asn Ser Leu Arg Ala Glu Asp Thr Ala Val Tyr Tyr Cys Ala Arg
```

```
                    20                  25                  30
```

<210> SEQ ID NO 26
<211> LENGTH: 11
<212> TYPE: PRT
<213> ORGANISM: Artificial Sequence
<220> FEATURE:
<223> OTHER INFORMATION: Synthetic Construct

<400> SEQUENCE: 26

```
Trp Gly Gln Gly Thr Leu Val Thr Val Ser Ser
1               5                   10
```

<210> SEQ ID NO 27
<211> LENGTH: 23
<212> TYPE: PRT
<213> ORGANISM: Artificial Sequence
<220> FEATURE:
<223> OTHER INFORMATION: Synthetic Construct

<400> SEQUENCE: 27

```
Asp Ile Gln Met Thr Gln Ser Pro Ser Ser Leu Ser Ala Ser Val Gly
1               5                   10                  15

Asp Arg Val Thr Ile Thr Cys
            20
```

<210> SEQ ID NO 28
<211> LENGTH: 15
<212> TYPE: PRT
<213> ORGANISM: Artificial Sequence
<220> FEATURE:
<223> OTHER INFORMATION: Synthetic Construct

<400> SEQUENCE: 28

```
Trp Tyr Gln Gln Lys Pro Gly Lys Ala Pro Lys Pro Leu Ile Tyr
1               5                   10                  15
```

<210> SEQ ID NO 29
<211> LENGTH: 32
<212> TYPE: PRT
<213> ORGANISM: Artificial Sequence
<220> FEATURE:
<223> OTHER INFORMATION: Synthetic Construct

<400> SEQUENCE: 29

```
Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30
```

<210> SEQ ID NO 30
<211> LENGTH: 10
<212> TYPE: PRT
<213> ORGANISM: Artificial Sequence
<220> FEATURE:
<223> OTHER INFORMATION: Synthetic Construct

<400> SEQUENCE: 30

```
Phe Gly Gln Gly Thr Lys Val Glu Ile Lys
1               5                   10
```

<210> SEQ ID NO 31
<211> LENGTH: 122
<212> TYPE: PRT
<213> ORGANISM: Artificial Sequence
<220> FEATURE:

<223> OTHER INFORMATION: Synthetic Construct

<400> SEQUENCE: 31

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Ser Tyr
            20                  25                  30

Asn Met His Trp Val Arg Gln Ala Pro Gly Lys Gly Leu Glu Trp Val
        35                  40                  45

Gly Ala Ile Tyr Pro Gly Asn Gly Asp Thr Ser Tyr Asn Gln Lys Phe
    50                  55                  60

Lys Gly Arg Phe Thr Ile Ser Val Asp Lys Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Val Tyr Tyr Ser Asn Ser Tyr Trp Tyr Phe Asp Val Trp
            100                 105                 110

Gly Gln Gly Thr Leu Val Thr Val Ser Ser
        115                 120

<210> SEQ ID NO 32
<211> LENGTH: 106
<212> TYPE: PRT
<213> ORGANISM: Artificial Sequence
<220> FEATURE:
<223> OTHER INFORMATION: Synthetic Construct

<400> SEQUENCE: 32

Asp Ile Gln Met Thr Gln Ser Pro Ser Ser Leu Ser Ala Ser Val Gly
1               5                   10                  15

Asp Arg Val Thr Ile Thr Cys Arg Ala Ser Ser Ser Val Ser Tyr Met
            20                  25                  30

His Trp Tyr Gln Gln Lys Pro Gly Lys Ala Pro Lys Pro Leu Ile Tyr
        35                  40                  45

Ala Pro Ser Asn Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Ser Phe Asn Pro Pro Thr
                85                  90                  95

Phe Gly Gln Gly Thr Lys Val Glu Ile Lys
            100                 105

<210> SEQ ID NO 33
<211> LENGTH: 5
<212> TYPE: PRT
<213> ORGANISM: Artificial Sequence
<220> FEATURE:
<223> OTHER INFORMATION: Synthetic Construct

<400> SEQUENCE: 33

Arg Phe Gly Val His
1               5

<210> SEQ ID NO 34
<211> LENGTH: 16
<212> TYPE: PRT
<213> ORGANISM: Artificial Sequence
<220> FEATURE:
<223> OTHER INFORMATION: Synthetic Construct

```
<400> SEQUENCE: 34

Val Ile Trp Arg Gly Gly Ser Thr Asp Tyr Asn Ala Ala Phe Met Ser
1               5                   10                  15

<210> SEQ ID NO 35
<211> LENGTH: 12
<212> TYPE: PRT
<213> ORGANISM: Artificial Sequence
<220> FEATURE:
<223> OTHER INFORMATION: Synthetic Construct

<400> SEQUENCE: 35

His Tyr Tyr Gly Ser Ser Asp Tyr Ala Leu Asp Asn
1               5                   10

<210> SEQ ID NO 36
<211> LENGTH: 11
<212> TYPE: PRT
<213> ORGANISM: Artificial Sequence
<220> FEATURE:
<223> OTHER INFORMATION: Synthetic Construct

<400> SEQUENCE: 36

Lys Ala Ser Gln Asp Val Ser Asn Ile Val Val
1               5                   10

<210> SEQ ID NO 37
<211> LENGTH: 7
<212> TYPE: PRT
<213> ORGANISM: Artificial Sequence
<220> FEATURE:
<223> OTHER INFORMATION: Synthetic Construct

<400> SEQUENCE: 37

Ser Ala Ser Tyr Arg Tyr Thr
1               5

<210> SEQ ID NO 38
<211> LENGTH: 9
<212> TYPE: PRT
<213> ORGANISM: Artificial Sequence
<220> FEATURE:
<223> OTHER INFORMATION: Synthetic Construct

<400> SEQUENCE: 38

Gln Gln His Tyr Ser Ser Pro Tyr Thr
1               5

<210> SEQ ID NO 39
<211> LENGTH: 30
<212> TYPE: PRT
<213> ORGANISM: Artificial Sequence
<220> FEATURE:
<223> OTHER INFORMATION: Synthetic Construct

<400> SEQUENCE: 39

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr
            20                  25                  30

<210> SEQ ID NO 40
<211> LENGTH: 14
<212> TYPE: PRT
<213> ORGANISM: Artificial Sequence
```

<220> FEATURE:
<223> OTHER INFORMATION: Synthetic Construct

<400> SEQUENCE: 40

Trp Val Arg Gln Ser Pro Gly Lys Gly Leu Glu Trp Leu Gly
1               5                   10

<210> SEQ ID NO 41
<211> LENGTH: 32
<212> TYPE: PRT
<213> ORGANISM: Artificial Sequence
<220> FEATURE:
<223> OTHER INFORMATION: Synthetic Construct

<400> SEQUENCE: 41

Arg Leu Thr Ile Thr Lys Asp Asn Ser Lys Ser Gln Val Phe Phe Lys
1               5                   10                  15

Leu Asn Ser Leu Lys Val Asp Asp Thr Ala Ile Tyr Tyr Cys Ser Asn
            20                  25                  30

<210> SEQ ID NO 42
<211> LENGTH: 11
<212> TYPE: PRT
<213> ORGANISM: Artificial Sequence
<220> FEATURE:
<223> OTHER INFORMATION: Synthetic Construct

<400> SEQUENCE: 42

Trp Gly Gln Gly Ile Ser Val Thr Val Ser Ser
1               5                   10

<210> SEQ ID NO 43
<211> LENGTH: 23
<212> TYPE: PRT
<213> ORGANISM: Artificial Sequence
<220> FEATURE:
<223> OTHER INFORMATION: Synthetic Construct

<400> SEQUENCE: 43

Asp Ile Val Met Thr Gln Ser His Lys Ile Met Ser Thr Ser Val Gly
1               5                   10                  15

Asp Arg Val Ser Ile Thr Cys
            20

<210> SEQ ID NO 44
<211> LENGTH: 15
<212> TYPE: PRT
<213> ORGANISM: Artificial Sequence
<220> FEATURE:
<223> OTHER INFORMATION: Synthetic Construct

<400> SEQUENCE: 44

Trp Phe Gln Gln Lys Pro Gly Gln Ser Pro Asn Leu Leu Ile Tyr
1               5                   10                  15

<210> SEQ ID NO 45
<211> LENGTH: 32
<212> TYPE: PRT
<213> ORGANISM: Artificial Sequence
<220> FEATURE:
<223> OTHER INFORMATION: Synthetic Construct

<400> SEQUENCE: 45

Gly Val Pro Asp Arg Phe Thr Gly Ser Gly Ser Gly Thr Asp Phe Thr
1               5                   10                  15

```
Phe Thr Ile Ser Ser Val Gln Ala Glu Asp Leu Ala Val Tyr Tyr Cys
                20                  25                  30
```

<210> SEQ ID NO 46
<211> LENGTH: 10
<212> TYPE: PRT
<213> ORGANISM: Artificial Sequence
<220> FEATURE:
<223> OTHER INFORMATION: Synthetic Construct

<400> SEQUENCE: 46

```
Phe Gly Gly Gly Thr Lys Leu Glu Ile Lys
1               5                   10
```

<210> SEQ ID NO 47
<211> LENGTH: 120
<212> TYPE: PRT
<213> ORGANISM: Artificial Sequence
<220> FEATURE:
<223> OTHER INFORMATION: Synthetic Construct

<400> SEQUENCE: 47

```
Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Arg Phe
                20                  25                  30

Gly Val His Trp Val Arg Gln Ser Pro Gly Lys Gly Leu Glu Trp Leu
            35                  40                  45

Gly Val Ile Trp Arg Gly Gly Ser Thr Asp Tyr Asn Ala Ala Phe Met
        50                  55                  60

Ser Arg Leu Thr Ile Thr Lys Asp Asn Ser Lys Ser Gln Val Phe Phe
65                  70                  75                  80

Lys Leu Asn Ser Leu Lys Val Asp Asp Thr Ala Ile Tyr Tyr Cys Ser
                85                  90                  95

Asn His Tyr Tyr Gly Ser Ser Asp Tyr Ala Leu Asp Asn Trp Gly Gln
            100                 105                 110

Gly Ile Ser Val Thr Val Ser Ser
        115                 120
```

<210> SEQ ID NO 48
<211> LENGTH: 107
<212> TYPE: PRT
<213> ORGANISM: Artificial Sequence
<220> FEATURE:
<223> OTHER INFORMATION: Synthetic Construct

<400> SEQUENCE: 48

```
Asp Ile Val Met Thr Gln Ser His Lys Ile Met Ser Thr Ser Val Gly
1               5                   10                  15

Asp Arg Val Ser Ile Thr Cys Lys Ala Ser Gln Asp Val Ser Asn Ile
                20                  25                  30

Val Val Trp Phe Gln Gln Lys Pro Gly Gln Ser Pro Asn Leu Leu Ile
            35                  40                  45

Tyr Ser Ala Ser Tyr Arg Tyr Thr Gly Val Pro Asp Arg Phe Thr Gly
        50                  55                  60

Ser Gly Ser Gly Thr Asp Phe Thr Phe Thr Ile Ser Ser Val Gln Ala
65                  70                  75                  80

Glu Asp Leu Ala Val Tyr Tyr Cys Gln Gln His Tyr Ser Ser Pro Tyr
                85                  90                  95

Thr Phe Gly Gly Gly Thr Lys Leu Glu Ile Lys
```

<210> SEQ ID NO 49
<211> LENGTH: 6
<212> TYPE: PRT
<213> ORGANISM: Artificial Sequence
<220> FEATURE:
<223> OTHER INFORMATION: Synthetic Construct

<400> SEQUENCE: 49

Ser Asp Tyr Val Trp Asn
1               5

<210> SEQ ID NO 50
<211> LENGTH: 16
<212> TYPE: PRT
<213> ORGANISM: Artificial Sequence
<220> FEATURE:
<223> OTHER INFORMATION: Synthetic Construct

<400> SEQUENCE: 50

Tyr Ile His Tyr Ser Gly Gly Thr Ser Tyr Asn Pro Ser Leu Lys Ser
1               5                   10                  15

<210> SEQ ID NO 51
<211> LENGTH: 9
<212> TYPE: PRT
<213> ORGANISM: Artificial Sequence
<220> FEATURE:
<223> OTHER INFORMATION: Synthetic Construct

<400> SEQUENCE: 51

Gly Asn Tyr Asp Trp Ala Phe Ala Tyr
1               5

<210> SEQ ID NO 52
<211> LENGTH: 11
<212> TYPE: PRT
<213> ORGANISM: Artificial Sequence
<220> FEATURE:
<223> OTHER INFORMATION: Synthetic Construct

<400> SEQUENCE: 52

Arg Ala Ser Lys Ser Ile Ser Lys Tyr Leu Ala
1               5                   10

<210> SEQ ID NO 53
<211> LENGTH: 7
<212> TYPE: PRT
<213> ORGANISM: Artificial Sequence
<220> FEATURE:
<223> OTHER INFORMATION: Synthetic Construct

<400> SEQUENCE: 53

Ser Gly Ser Thr Leu Gln Ser
1               5

<210> SEQ ID NO 54
<211> LENGTH: 9
<212> TYPE: PRT
<213> ORGANISM: Artificial Sequence
<220> FEATURE:
<223> OTHER INFORMATION: Synthetic Construct

<400> SEQUENCE: 54

Gln Gln His Asn Glu Tyr Pro Trp Thr
1               5

<210> SEQ ID NO 55
<211> LENGTH: 471
<212> TYPE: PRT
<213> ORGANISM: Artificial Sequence
<220> FEATURE:
<223> OTHER INFORMATION: Synthetic Construct

<400> SEQUENCE: 55

```
Met Lys Lys Asn Ile Ala Phe Leu Leu Ala Ser Met Phe Val Phe Ser
1               5                   10                  15

Ile Ala Thr Asn Ala Tyr Ala Glu Val Gln Leu Val Glu Ser Gly Pro
            20                  25                  30

Gly Leu Val Lys Pro Ser Glu Thr Leu Ser Leu Thr Cys Thr Val Ser
        35                  40                  45

Gly Tyr Ser Ile Thr Ser Asp Tyr Val Trp Asn Trp Ile Arg Gln Pro
    50                  55                  60

Pro Gly Lys Gly Leu Glu Trp Ile Gly Tyr Ile His Tyr Ser Gly Gly
65                  70                  75                  80

Thr Ser Tyr Asn Pro Ser Leu Lys Ser Arg Val Thr Ile Ser Arg Asp
                85                  90                  95

Thr Ser Lys Asn Gln Phe Ser Leu Lys Leu Ser Ser Val Thr Ala Ala
            100                 105                 110

Asp Thr Ala Val Tyr Tyr Cys Ala Arg Gly Asn Tyr Asp Trp Ala Phe
        115                 120                 125

Ala Tyr Trp Gly Gln Gly Thr Leu Val Thr Val Ser Ser Ala Ser Thr
    130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Gln Thr Tyr Ile Cys
    210                 215                 220

Asn Val Asn His Lys Pro Ser Asn Thr Lys Val Asp Lys Lys Val Glu
225                 230                 235                 240

Pro Lys Ser Cys Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser His Glu Asp Pro Glu Val Lys Phe Asn Trp Tyr Val Asp
    290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
        355                 360                 365
```

```
Glu Pro Gln Val Tyr Thr Leu Pro Pro Ser Arg Glu Met Thr Lys
        370                 375                 380

Asn Gln Val Ser Leu Trp Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
        435                 440                 445

Cys Ser Val Met His Glu Ala Leu His Asn His Tyr Thr Gln Lys Ser
    450                 455                 460

Leu Ser Leu Ser Pro Gly Lys
465             470
```

<210> SEQ ID NO 56
<211> LENGTH: 237
<212> TYPE: PRT
<213> ORGANISM: Artificial Sequence
<220> FEATURE:
<223> OTHER INFORMATION: Synthetic Construct

<400> SEQUENCE: 56

```
Met Lys Lys Asn Ile Ala Phe Leu Leu Ala Ser Met Phe Val Phe Ser
1               5                   10                  15

Ile Ala Thr Asn Ala Tyr Ala Asp Ile Gln Met Thr Gln Ser Pro Ser
                20                  25                  30

Ser Leu Ser Ala Ser Val Gly Asp Arg Val Thr Ile Thr Cys Arg Ala
        35                  40                  45

Ser Lys Ser Ile Ser Lys Tyr Leu Ala Trp Tyr Gln Gln Lys Pro Gly
    50                  55                  60

Lys Ala Asn Lys Leu Leu Ile Ser Ser Gly Ser Thr Leu Gln Ser Gly
65                  70                  75                  80

Val Pro Ser Arg Phe Ser Gly Ser Gly Ser Gly Thr Asp Phe Thr Leu
                85                  90                  95

Thr Ile Ser Ser Leu Gln Pro Glu Asp Phe Ala Thr Tyr Tyr Cys Gln
                100                 105                 110

Gln His Asn Glu Tyr Pro Trp Thr Phe Gly Gly Gly Thr Lys Val Glu
            115                 120                 125

Ile Lys Arg Thr Val Ala Ala Pro Ser Val Phe Ile Phe Pro Pro Ser
    130                 135                 140

Asp Glu Gln Leu Lys Ser Gly Thr Ala Ser Val Val Cys Leu Leu Asn
145                 150                 155                 160

Asn Phe Tyr Pro Arg Glu Ala Lys Val Gln Trp Lys Val Asp Asn Ala
                165                 170                 175

Leu Gln Ser Gly Asn Ser Gln Glu Ser Val Thr Glu Gln Asp Ser Lys
            180                 185                 190

Asp Ser Thr Tyr Ser Leu Ser Ser Thr Leu Thr Leu Ser Lys Ala Asp
        195                 200                 205

Tyr Glu Lys His Lys Val Tyr Ala Cys Glu Val Thr His Gln Gly Leu
    210                 215                 220

Ser Ser Pro Val Thr Lys Ser Phe Asn Arg Gly Glu Cys
225                 230                 235
```

<210> SEQ ID NO 57

```
<211> LENGTH: 5
<212> TYPE: PRT
<213> ORGANISM: Artificial Sequence
<220> FEATURE:
<223> OTHER INFORMATION: Synthetic Construct

<400> SEQUENCE: 57

Ser Tyr Tyr Ile His
1               5

<210> SEQ ID NO 58
<211> LENGTH: 17
<212> TYPE: PRT
<213> ORGANISM: Artificial Sequence
<220> FEATURE:
<223> OTHER INFORMATION: Synthetic Construct

<400> SEQUENCE: 58

Trp Ile Tyr Pro Glu Asn Asp Asn Thr Lys Tyr Asn Glu Lys Phe Lys
1               5                   10                  15

Asp

<210> SEQ ID NO 59
<211> LENGTH: 10
<212> TYPE: PRT
<213> ORGANISM: Artificial Sequence
<220> FEATURE:
<223> OTHER INFORMATION: Synthetic Construct

<400> SEQUENCE: 59

Asp Gly Tyr Ser Arg Tyr Tyr Phe Asp Tyr
1               5                   10

<210> SEQ ID NO 60
<211> LENGTH: 17
<212> TYPE: PRT
<213> ORGANISM: Artificial Sequence
<220> FEATURE:
<223> OTHER INFORMATION: Synthetic Construct

<400> SEQUENCE: 60

Lys Ser Ser Gln Ser Leu Leu Asn Ser Arg Thr Arg Lys Asn Tyr Leu
1               5                   10                  15

Ala

<210> SEQ ID NO 61
<211> LENGTH: 7
<212> TYPE: PRT
<213> ORGANISM: Artificial Sequence
<220> FEATURE:
<223> OTHER INFORMATION: Synthetic Construct

<400> SEQUENCE: 61

Trp Thr Ser Thr Arg Lys Ser
1               5

<210> SEQ ID NO 62
<211> LENGTH: 8
<212> TYPE: PRT
<213> ORGANISM: Artificial Sequence
<220> FEATURE:
<223> OTHER INFORMATION: Synthetic Construct

<400> SEQUENCE: 62

Lys Gln Ser Phe Ile Leu Arg Thr
1               5
```

<210> SEQ ID NO 63
<211> LENGTH: 119
<212> TYPE: PRT
<213> ORGANISM: Artificial Sequence
<220> FEATURE:
<223> OTHER INFORMATION: Synthetic Construct

<400> SEQUENCE: 63

Glu Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Thr Ser Tyr
            20                  25                  30

Tyr Ile His Trp Val Arg Gln Ala Pro Gly Gln Gly Leu Glu Trp Ile
        35                  40                  45

Gly Trp Ile Tyr Pro Glu Asn Asp Asn Thr Lys Tyr Asn Glu Lys Phe
    50                  55                  60

Lys Asp Arg Val Thr Ile Thr Ala Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Asp Gly Tyr Ser Arg Tyr Tyr Phe Asp Tyr Trp Gly Gln Gly
            100                 105                 110

Thr Leu Val Thr Val Ser Ser
        115

<210> SEQ ID NO 64
<211> LENGTH: 112
<212> TYPE: PRT
<213> ORGANISM: Artificial Sequence
<220> FEATURE:
<223> OTHER INFORMATION: Synthetic Construct

<400> SEQUENCE: 64

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Ser Pro Lys Leu Leu Ile Tyr Trp Thr Ser Thr Arg Lys Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Ser Phe Ile Leu Arg Thr Phe Gly Gln Gly Thr Lys Val Glu Ile Lys
            100                 105                 110

<210> SEQ ID NO 65
<211> LENGTH: 5
<212> TYPE: PRT
<213> ORGANISM: Artificial Sequence
<220> FEATURE:
<223> OTHER INFORMATION: Synthetic Construct

<400> SEQUENCE: 65

Asn Tyr Tyr Ile His
1               5

```
<210> SEQ ID NO 66
<211> LENGTH: 17
<212> TYPE: PRT
<213> ORGANISM: Artificial Sequence
<220> FEATURE:
<223> OTHER INFORMATION: Synthetic Construct

<400> SEQUENCE: 66

Trp Ile Tyr Pro Gly Asp Gly Asn Thr Lys Tyr Asn Glu Lys Phe Lys
1               5                   10                  15

Gly

<210> SEQ ID NO 67
<211> LENGTH: 10
<212> TYPE: PRT
<213> ORGANISM: Artificial Sequence
<220> FEATURE:
<223> OTHER INFORMATION: Synthetic Construct

<400> SEQUENCE: 67

Asp Ser Tyr Ser Asn Tyr Tyr Phe Asp Tyr
1               5                   10

<210> SEQ ID NO 68
<211> LENGTH: 17
<212> TYPE: PRT
<213> ORGANISM: Artificial Sequence
<220> FEATURE:
<223> OTHER INFORMATION: Synthetic Construct

<400> SEQUENCE: 68

Lys Ser Ser Gln Ser Leu Leu Asn Ser Arg Thr Arg Lys Asn Tyr Leu
1               5                   10                  15

Ala

<210> SEQ ID NO 69
<211> LENGTH: 7
<212> TYPE: PRT
<213> ORGANISM: Artificial Sequence
<220> FEATURE:
<223> OTHER INFORMATION: Synthetic Construct

<400> SEQUENCE: 69

Trp Ala Ser Thr Arg Glu Ser
1               5

<210> SEQ ID NO 70
<211> LENGTH: 8
<212> TYPE: PRT
<213> ORGANISM: Artificial Sequence
<220> FEATURE:
<223> OTHER INFORMATION: Synthetic Construct

<400> SEQUENCE: 70

Thr Gln Ser Phe Ile Leu Arg Thr
1               5

<210> SEQ ID NO 71
<211> LENGTH: 119
<212> TYPE: PRT
<213> ORGANISM: Artificial Sequence
<220> FEATURE:
<223> OTHER INFORMATION: Synthetic Construct

<400> SEQUENCE: 71
```

```
Gln Val Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Asn Tyr
            20                  25                  30

Tyr Ile His Trp Val Lys Gln Arg Pro Gly Gln Gly Leu Glu Trp Ile
        35                  40                  45

Gly Trp Ile Tyr Pro Gly Asp Gly Asn Thr Lys Tyr Asn Glu Lys Phe
    50                  55                  60

Lys Gly Lys Ala Thr Leu Thr Ala Asp Thr Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Asp Ser Tyr Ser Asn Tyr Tyr Phe Asp Tyr Trp Gly Gln Gly
            100                 105                 110

Thr Thr Leu Thr Val Ser Ser
            115
```

<210> SEQ ID NO 72
<211> LENGTH: 112
<212> TYPE: PRT
<213> ORGANISM: Artificial Sequence
<220> FEATURE:
<223> OTHER INFORMATION: Synthetic Construct

<400> SEQUENCE: 72

```
Asp Ile Val Met Thr Gln Ser Pro Ser Ser Leu Ala Val Ser Ala Gly
1               5                   10                  15

Glu Lys Val Thr Met Ser Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Thr Gln
                85                  90                  95

Ser Phe Ile Leu Arg Thr Phe Gly Gly Gly Thr Lys Leu Glu Ile Lys
            100                 105                 110
```

<210> SEQ ID NO 73
<211> LENGTH: 207
<212> TYPE: PRT
<213> ORGANISM: Homo sapiens

<400> SEQUENCE: 73

```
Met Gln Ser Gly Thr His Trp Arg Val Leu Gly Leu Cys Leu Leu Ser
1               5                   10                  15

Val Gly Val Trp Gly Gln Asp Gly Asn Glu Glu Met Gly Gly Ile Thr
            20                  25                  30

Gln Thr Pro Tyr Lys Val Ser Ile Ser Gly Thr Thr Val Ile Leu Thr
        35                  40                  45

Cys Pro Gln Tyr Pro Gly Ser Glu Ile Leu Trp Gln His Asn Asp Lys
    50                  55                  60

Asn Ile Gly Gly Asp Glu Asp Asp Lys Asn Ile Gly Ser Asp Glu Asp
65                  70                  75                  80

His Leu Ser Leu Lys Glu Phe Ser Glu Leu Glu Gln Ser Gly Tyr Tyr
```

```
                     85                  90                  95
Val Cys Tyr Pro Arg Gly Ser Lys Pro Glu Asp Ala Asn Phe Tyr Leu
                100                 105                 110

Tyr Leu Arg Ala Arg Val Cys Glu Asn Cys Met Glu Met Asp Val Met
            115                 120                 125

Ser Val Ala Thr Ile Val Ile Val Asp Ile Cys Ile Thr Gly Gly Leu
        130                 135                 140

Leu Leu Leu Val Tyr Tyr Trp Ser Lys Asn Arg Lys Ala Lys Ala Lys
145                 150                 155                 160

Pro Val Thr Arg Gly Ala Gly Gly Arg Gln Arg Gly Gln Asn
                165                 170                 175

Lys Glu Arg Pro Pro Val Pro Asn Pro Asp Tyr Glu Pro Ile Arg
            180                 185                 190

Lys Gly Gln Arg Asp Leu Tyr Ser Gly Leu Asn Gln Arg Ile
            195                 200                 205

<210> SEQ ID NO 74
<211> LENGTH: 198
<212> TYPE: PRT
<213> ORGANISM: Macaca fascicularis

<400> SEQUENCE: 74

Met Gln Ser Gly Thr Arg Trp Arg Val Leu Gly Leu Cys Leu Leu Ser
1               5                   10                  15

Ile Gly Val Trp Gly Gln Asp Gly Asn Glu Glu Met Gly Ser Ile Thr
            20                  25                  30

Gln Thr Pro Tyr Gln Val Ser Ile Ser Gly Thr Thr Val Ile Leu Thr
        35                  40                  45

Cys Ser Gln His Leu Gly Ser Glu Ala Gln Trp Gln His Asn Gly Lys
    50                  55                  60

Asn Lys Glu Asp Ser Gly Asp Arg Leu Phe Leu Pro Glu Phe Ser Glu
65                  70                  75                  80

Met Glu Gln Ser Gly Tyr Tyr Val Cys Tyr Pro Arg Gly Ser Asn Pro
                85                  90                  95

Glu Asp Ala Ser His His Leu Tyr Leu Lys Ala Arg Val Cys Glu Asn
                100                 105                 110

Cys Met Glu Met Asp Val Met Ala Val Ala Thr Ile Val Ile Val Asp
            115                 120                 125

Ile Cys Ile Thr Leu Gly Leu Leu Leu Val Tyr Tyr Trp Ser Lys
        130                 135                 140

Asn Arg Lys Ala Lys Ala Lys Pro Val Thr Arg Gly Ala Gly Ala Gly
145                 150                 155                 160

Gly Arg Gln Arg Gly Gln Asn Lys Glu Arg Pro Pro Val Pro Asn
                165                 170                 175

Pro Asp Tyr Glu Pro Ile Arg Lys Gly Gln Gln Asp Leu Tyr Ser Gly
            180                 185                 190

Leu Asn Gln Arg Arg Ile
            195

<210> SEQ ID NO 75
<211> LENGTH: 182
<212> TYPE: PRT
<213> ORGANISM: Homo sapiens

<400> SEQUENCE: 75

Met Glu Gln Gly Lys Gly Leu Ala Val Leu Ile Leu Ala Ile Ile Leu
```

```
            1               5                  10                 15
Leu Gln Gly Thr Leu Ala Gln Ser Ile Lys Gly Asn His Leu Val Lys
                20                  25                 30

Val Tyr Asp Tyr Gln Glu Asp Gly Ser Val Leu Leu Thr Cys Asp Ala
                35                  40                 45

Glu Ala Lys Asn Ile Thr Trp Phe Lys Asp Gly Lys Met Ile Gly Phe
                50                  55                 60

Leu Thr Glu Asp Lys Lys Lys Trp Asn Leu Gly Ser Asn Ala Lys Asp
65                  70                  75                 80

Pro Arg Gly Met Tyr Gln Cys Lys Gly Ser Gln Asn Lys Ser Lys Pro
                85                  90                 95

Leu Gln Val Tyr Tyr Arg Met Cys Gln Asn Cys Ile Glu Leu Asn Ala
                100                 105                110

Ala Thr Ile Ser Gly Phe Leu Phe Ala Glu Ile Val Ser Ile Phe Val
                115                 120                125

Leu Ala Val Gly Val Tyr Phe Ile Ala Gly Gln Asp Gly Val Arg Gln
                130                 135                140

Ser Arg Ala Ser Asp Lys Gln Thr Leu Leu Pro Asn Asp Gln Leu Tyr
145                 150                 155                160

Gln Pro Leu Lys Asp Arg Glu Asp Asp Gln Tyr Ser His Leu Gln Gly
                165                 170                175

Asn Gln Leu Arg Arg Asn
                180

<210> SEQ ID NO 76
<211> LENGTH: 181
<212> TYPE: PRT
<213> ORGANISM: Macaca fascicularis

<400> SEQUENCE: 76

Met Val Gln Gly Lys Gly Leu Thr Gly Phe Ile Leu Ala Ile Ile Leu
1               5                   10                 15

Leu Gln Gly Ser Leu Ala Gln Ser Phe Glu Glu Asn Arg Lys Leu Asn
                20                  25                 30

Val Tyr Asn Gln Glu Asp Gly Ser Val Leu Leu Thr Cys His Val Lys
                35                  40                 45

Asn Thr Asn Ile Thr Trp Phe Lys Glu Gly Lys Met Ile Asp Ile Leu
                50                  55                 60

Thr Ala His Lys Asn Lys Trp Asn Leu Gly Ser Asn Thr Lys Asp Pro
65                  70                  75                 80

Arg Gly Val Tyr Gln Cys Lys Gly Ser Lys Asp Lys Ser Lys Thr Leu
                85                  90                 95

Gln Val Tyr Tyr Arg Met Cys Gln Asn Cys Ile Glu Leu Asn Ala Ala
                100                 105                110

Thr Ile Leu Gly Phe Val Phe Ala Glu Ile Ile Ser Ile Phe Phe Leu
                115                 120                125

Ala Val Gly Val Tyr Phe Ile Ala Gly Gln Asp Gly Val Arg Gln Ser
                130                 135                140

Arg Ala Ser Asp Lys Gln Thr Leu Leu Pro Asn Asp Gln Leu Tyr Gln
145                 150                 155                160

Pro Leu Lys Asp Arg Glu Asp Asp Gln Tyr Ser His Leu Gln Gly Asn
                165                 170                175

Gln Leu Arg Met Asn
                180
```

```
<210> SEQ ID NO 77
<211> LENGTH: 27
<212> TYPE: PRT
<213> ORGANISM: Artificial Sequence
<220> FEATURE:
<223> OTHER INFORMATION: Synthetic Construct

<400> SEQUENCE: 77

Gln Asp Gly Asn Glu Glu Met Gly Gly Ile Thr Gln Thr Pro Tyr Lys
1               5                   10                  15

Val Ser Ile Ser Gly Thr Thr Val Ile Leu Thr
            20                  25

<210> SEQ ID NO 78
<211> LENGTH: 28
<212> TYPE: PRT
<213> ORGANISM: Artificial Sequence
<220> FEATURE:
<223> OTHER INFORMATION: Synthetic Construct

<400> SEQUENCE: 78

Gln Asp Gly Asn Glu Glu Met Gly Gly Ile Thr Gln Thr Pro Tyr Lys
1               5                   10                  15

Val Ser Ile Ser Gly Thr Thr Val Ile Leu Thr Cys
            20                  25

<210> SEQ ID NO 79
<211> LENGTH: 16
<212> TYPE: PRT
<213> ORGANISM: Artificial Sequence
<220> FEATURE:
<223> OTHER INFORMATION: Synthetic Construct

<400> SEQUENCE: 79

Gln Asp Gly Asn Glu Glu Met Gly Gly Ile Thr Gln Thr Pro Tyr Lys
1               5                   10                  15
```

ANTI-CD3 ANTIBODIES AND METHODS OF USE

SEQUENCE LISTING

The instant application contains a Sequence Listing which has been submitted electronically in ASCII format and is hereby incorporated by reference in its entirety. Said ASCII copy, created on Dec. 6, 2017, is named 50474-118002_Sequence_Listing_12.6.17_ST25 and is 39,674 bytes in size.

FIELD OF THE INVENTION

The present invention relates to anti-cluster of differentiation 3 (CD3) antibodies and methods of using the same.

BACKGROUND

Cell proliferative disorders, such as cancer, are characterized by the uncontrolled growth of cell subpopulations. They are the leading cause of death in the developed world and the second leading cause of death in developing countries, with over 12 million new cancer cases diagnosed and 7 million cancer deaths occurring each year. The American Cancer Society estimates that greater than half a million Americans will die of cancer in 2015, accounting for nearly one out of every four deaths in the country. As the elderly population has grown, the incidence of cancer has concurrently risen, as the probability of developing cancer is more than two-fold higher after the age of seventy. Cancer care thus represents a significant and ever-increasing societal burden.

Longstanding approaches to cancer treatment include chemotherapy, radiation therapy, and surgery to remove solid tumors. Recently, T cell-targeting therapeutic antibodies have been developed. These therapeutic antibodies include bispecific antibodies that are capable of simultaneously binding cell surface antigens on T cells and cell surface antigens on tumor cells, thereby enabling the bound T cells to contribute to the destruction of the tumor cells.

Existing bispecific antibodies currently undergoing clinical trials for treating cancer are limited by their short half-lives and/or variable efficacy. Thus, there is an unmet need in the field for the development of effective bispecific antibodies for use in cancer treatment.

SUMMARY

The present invention relates to anti-cluster of differentiation 3 (CD3) antibodies and methods of using the same.

In one aspect, the invention features an anti-CD3 antibody, wherein the anti-CD3 antibody comprises a binding domain comprising the following six hypervariable regions (HVRs): (a) an HVR-H1 comprising the amino acid sequence of SEQ ID NO: 1; (b) an HVR-H2 comprising the amino acid sequence of SEQ ID NO: 2; (c) an HVR-H3 comprising the amino acid sequence of SEQ ID NO: 3; (d) an HVR-L1 comprising the amino acid sequence of SEQ ID NO: 4; (e) an HVR-L2 comprising the amino acid sequence of SEQ ID NO: 5; and (f) an HVR-L3 comprising the amino acid sequence of SEQ ID NO: 6. In some embodiments, the binding domain comprises (a) a heavy chain variable (VH) domain comprising an amino acid sequence having at least 95% sequence identity to the amino acid sequence of SEQ ID NO: 7; (b) a light chain variable (VL) domain comprising an amino acid sequence having at least 95% sequence identity to the amino acid sequence of SEQ ID NO: 8; or (c) a VH domain as in (a) and a VL domain as in (b). In some embodiments, the VH domain comprises the amino acid sequence of SEQ ID NO: 7. In some embodiments, the VL domain comprises the amino acid sequence of SEQ ID NO: 8. In some embodiments, the binding domain comprises (a) a heavy chain variable (VH) domain comprising an amino acid sequence having at least 95% sequence identity to the amino acid sequence of SEQ ID NO: 7 and (b) a light chain variable (VL) domain comprising an amino acid sequence having at least 95% sequence identity to the amino acid sequence of SEQ ID NO: 8. In some embodiments, the VH domain comprises the amino acid sequence of SEQ ID NO: 7. In some embodiments, the VL domain comprises the amino acid sequence of SEQ ID NO: 8. In some embodiments, the anti-CD3 antibody binds the human CD3ε polypeptide with a $K_D$ of 0.7 nM or lower (e.g., a $K_D$ of 0.6 nM or lower, e.g., a $K_D$ of 0.5 nM or lower, e.g., a $K_D$ of 0.4 nM or lower, e.g., a $K_D$ of 0.3 nM or lower, e.g., a $K_D$ of 0.2 nM or lower, e.g., a $K_D$ of 0.1 nM or lower).

In some embodiments, any one of the preceding anti-CD3 antibodies can be monoclonal, human, humanized, or chimeric. In some embodiments, any one of the preceding anti-CD3 antibodies can be an antibody fragment that binds CD3. In some embodiments, the antibody fragment is selected from the group consisting of Fab, Fab'-SH, Fv, scFv, and (Fab')$_2$ fragments. In other embodiments, the anti-CD3 antibody is a full-length antibody. In some embodiments, the anti-CD3 antibody is an IgG antibody (e.g., an IgG1, IgG2, or IgG3 antibody). In some embodiments, the anti-CD3 antibody is a monospecific antibody. In some embodiments, the anti-CD3 antibody is a Bispecific T-Cell Engager (BiTE®) antibody).

In some embodiments, the anti-CD3 antibody is a multispecific antibody. In some embodiments, the multispecific antibody is a bispecific antibody, such as a Ly6G6D TDB antibody. In some embodiments, the bispecific antibody comprises a second binding domain that binds to a second biological molecule, wherein the second biological molecule is a cell surface antigen (e.g., a cell surface antigen on a target cell other than an immune effector cell). In some embodiments, the cell surface antigen is expressed in low copy number on the target cell. For example, the cell surface antigen may be expressed at less than 35,000 copies per target cell. In some embodiments, the low-copy cell surface antigen may be expressed at about 100 copies per target cell to about 30,000 copies per target cell.

In some embodiments, the cell surface antigen is a tumor antigen. In some embodiments, the tumor antigen is selected from the group consisting of Ly6G6D (lymphocyte antigen 6 complex, locus G61); Ly6-D, MEGT1); CD20; FcRH5 (Fc Receptor-like 5); HER2; LYPD1; PMEL17 (silver homolog; SILV; D12S53E; PMEL17; (SI); (SIL); ME20; gp100); Ly6E (lymphocyte antigen 6 complex, locus E; Ly67, RIG-E, SCA-2, TSA-1); CD19; CD33; CD22 (B-cell receptor CD22-B isoform); CD79a (CD79A, CD79a, immunoglobulin-associated alpha; BMPR1B (bone morphogenetic protein receptor-type IB); CD79b (CD79B, CD79β, 1 Gb (immunoglobulin-associated beta), B29); EDAR (Ectodysplasin A Receptor); GFRA1 (GDNF-Ra1); MRP4 (Multidrug Resistance Protein 4); RET; STEAP1 (six transmembrane epithelial antigen of prostate); TENB2 (putative transmembrane proteoglycan); E16 (LAT1, SLC7A5); 0772P (CA125, MUC16); MPF (MPF, MSLN, SMR, megakaryocyte potentiating factor, mesothelin); Napi2b (NAPI-2B, NPTIIb, SLC34A2, solute carrier family 34 (sodium phosphate), member 2, type II sodium-dependent phosphate transporter 3b); Sema 5b; PSCA hlg (2700050C12Rik, C530008O16Rik, RIKEN cDNA 2700050C12, RIKEN cDNA 2700050C12 gene); ETBR (Endothelin type B receptor); MSG783 (RNF124, hypothetical protein FLJ20315); STEAP2; TrpM4 (BR22450, FLJ20041, TRPM4, TRPM4B, transient receptor potential cation channel, subfamily M, member 4); CRIPTO (CR, CR1, CRGF, CRIPTO, TDGF1, teratocarcinoma-derived growth factor); CD21 (CR2 (Complement receptor 2) or C3DR (C3d/Epstein Barr virus receptor) or Hs.73792); FcRH2 (IFGP4, IRTA4, SPAP1A (SH2 domain containing phosphatase anchor protein 1a), SPAP1B, SPAP1C); NCA; MDP; IL20Rα; Brevican; EphB2R; ASLG659; PSCA; GEDA; BAFF-R (B cell-activating factor receptor, BLyS receptor 3, BR3); CXCR5 (Burkitt's lymphoma receptor 1; HLA-DOB (Beta subunit of MHC class II molecule); P2X5 (Purinergic receptor P2X ligand-gated ion channel 5; CD72 (B-cell differentiation antigen CD72, Lyb-2); LY64 (Lymphocyte antigen 64 (RP105), type I membrane protein of the leucine rich repeat (LRR) family); FcRH1 (Fc receptor-like protein 1); IRTA2 (Immunoglobulin superfamily receptor translocation associated 2); TMEFF1; TMEM46 (shisa homolog 2 (*Xenopus laevis*); SHISA2); LGR5 (leucine-rich repeat-containing G protein-coupled receptor 5; GPR49, GPR67); LY6K (lymphocyte antigen 6 complex, locus K; LY6K; HSJ001348; FLJ35226); GPR19 (G protein-coupled receptor 19; Mm 4787); GPR54 (KISS1 receptor; KISS1R; GPR54; HOT7T175; AXOR12); ASPHD1 (aspartate beta-hydroxylase domain containing 1; LOC253982); Tyrosinase (TYR; OCAIA; OCA1A; tyrosinase; SHEP3); TMEM118 (ring finger protein, transmembrane 2; RNFT2; FLJ14627); GPR172A (G protein-coupled receptor 172A; GPCR41; FLJ11856; D15Ertd747e); GPC3 (Glypican 3); CLL1 (C-Type Lectin-like molecule 1); B7-H4 (B7x; B7S1); RNF43 (Ring finger protein 43); CD70; CXORF61 (Chromosome X open reading frame 61); HAVCR1; Epiregulin; Amphiregulin; EGFR; EGFR-L858R; EGFR-L861Q; EGFR-G719A; EGFR-G719S; EGFR-G719C; EGFR-T790M; EGFR-S7681; adipophilin; AIM-2; ALDH1A1; alpha-actinin-4; alpha-foetoprotein; ARTC1; B-RAF; BAGE-1; BCLX (L); BCR-ABL fusion protein (b3a2); beta-catenin; BING-4; CALCA; CASP-5; CASP-8; CD45; Cdc27; CDK4; CDKN2A; CEA; CLPP; COA-1; CPSF; Cw6; cyclin D1; Cyclin-A1; dek-can fusion protein; DKK1; DR1; DR13; EFTUD2; Elongation factor 2; ENAH (hMena); EpCAM; EphA3; ETV6-AML1 fusion protein; EZH2; FLT3-ITD; FN1; G250; MN; CAIX; GAGE-1;2;8; GAGE-3;4;5;6;7; glypican-3; GnTVf; gp100/Pmel17; GPNMB; HERV-K-MEL; hsp70-2; IDO1; IGF2B3; IL13Ralpha2; Intestinal carboxyl esterase; K-ras; Kallikrein 4; KIF20A; KK-LC-1; KM-HN-1; LAGE-1; LDLR-fucosytransferaseASfusion protein; Lengsin; M-CSF; MAGE-A1; MAGE-A10; MAGE-A12; MAGE-A2; MAGE-A3; MAGE-A4; MAGE-A6; MAGE-A9; MAGE-C1; MAGE-C2; mammaglobin-A; MART2; MCSP; mdm-2; ME1; Melan-A/MART-1; Meloe; MMP-2; MMP-7; MUC1; MUC5AC; mucin; MUM-1f; MUM-2; MUM-3; Myosin class I; N-ras; NA88-A; neo-PAP; NFYC; NY-BR-1; NY-ESO-1/LAGE-2; OA1; OGT; OS-9; p53; PAP; PAX5; PBF; pml-RARalpha fusion protein; PRAME; PRDX5; PSMA; PTPRK; RAB38/NY-MEL-1; RAGE-1; RBAF600; RGS5; RhoC; RNF43; RU2AS; SAGE; secernin 1; SIRT2; SNRPD1; SOX10; Sp17; SSX-2; SSX-4; STEAP1; survivin; SYT-SSX1 or -SSX2 fusion protein; TAG-1; TAG-2; Telomerase; TGF-betaRII; TRAG-3; Triosephosphate isomerase; TRP-1/gp75; TRP-2; TRP2-INT2; tyrosinase; VEGF; WT1; XAGE-1b/GAGED2a; and SLC35D3. In some embodiments, the tumor antigen is selected from the group consisting of LY6G6D, CD20, FcRH5, HER2, LYPD1, PMEL17, LY6E, CD19, CD33, CD22, CD79A, CD79B, EDAR, GFRA1, MRP4, RET, Steap1, and TenB2.

In some embodiments, the tumor antigen is Ly6G6D, which may be present on the cell surface of the target cell at between about 20,000 copies per target cell to about 30,000 copies per target cell. In some embodiments, copy number may be determined by Scatchard plot analysis.

In a related aspect, the invention features an anti-CD3 antibody, wherein the anti-CD3 antibody is a bispecific antibody that binds to CD3 located on an immune effector cell and a cell surface antigen that is expressed in low copy number on a target cell other than the immune effector cell, wherein the bispecific antibody comprises an anti-CD3 arm comprising a first binding domain comprising the following six HVRs: (a) an HVR-H1 comprising the amino acid sequence of SEQ ID NO: 1; (b) an HVR-H2 comprising the amino acid sequence of SEQ ID NO: 2; (c) an HVR-H3 comprising the amino acid sequence of SEQ ID NO: 3; (d) an HVR-L1 comprising the amino acid sequence of SEQ ID NO: 4; (e) an HVR-L2 comprising the amino acid sequence of SEQ ID NO: 5; and (f) an HVR-L3 comprising the amino acid sequence of SEQ ID NO: 6; and an anti-cell surface antigen arm comprising a second binding domain. In some embodiments, the cell surface antigen is a tumor antigen. In some embodiments, the tumor antigen is Ly6G6D.

In some embodiments, any one of the preceding anti-CD3 antibodies may comprise a substitution mutation in the Fc region that reduces effector function. In some embodiments, the substitution mutation is an aglycosylation site mutation. In some embodiments, the aglycosylation site mutation is at amino acid residue N297, 1234, 1235, and/or D265 (EU numbering). In some embodiments, the aglycosylation site mutation is selected from the group consisting of N297G, N297A, L234A, L235A, and D265A. In some embodiments, the mutation is an N297G mutation. In some embodiments, the aglycosylation site mutation reduces effector function of the anti-CD3 antibody.

In some embodiments, any one of the preceding anti-CD3 antibodies can comprise one or more heavy chain constant domains, wherein the one or more heavy chain constant domains are selected from a first CH1 ($CH1_1$) domain, a first CH2 ($CH2_1$) domain, a first CH3 ($CH3_1$) domain, a second CH1 ($CH1_2$) domain, second CH2 ($CH2_2$) domain, and a second CH3 ($CH3_2$) domain. In some embodiments, at least one of the one or more heavy chain constant domains is paired with another heavy chain constant domain. In some embodiments, the $CH3_1$ and $CH3_2$ domains each comprise a protuberance or cavity, and wherein the protuberance or cavity in the $CH3_1$ domain is positionable in the cavity or protuberance, respectively, in the $CH3_2$ domain. In some embodiments, the $CH3_1$ and $CH3_2$ domains meet at an interface between said protuberance and cavity. In some embodiments, the $CH2_1$ and $CH2_2$ domains each comprise a protuberance or cavity, and wherein the protuberance or cavity in the $CH2_1$ domain is positionable in the cavity or protuberance, respectively, in the $CH2_2$ domain. In some embodiments, the $CH2_1$ and $CH2_2$ domains meet at an interface between said protuberance and cavity.

In some embodiments, the invention features an immunoconjugate comprising any one of the preceding anti-CD3 antibodies conjugated to a cytotoxic agent. Also provided is a composition comprising any one of the preceding anti-CD3 antibodies. In some embodiments, the composition further comprises a pharmaceutically acceptable carrier, excipient, or diluent. In some embodiments, the composition is a pharmaceutical composition. In some embodiments, the composition further comprises a PD-1 axis binding antagonist or an additional therapeutic agent. In another aspect, the invention features an isolated nucleic acid that encodes any of the anti-CD3 antibodies disclosed herein. In some embodiments, a vector (e.g., an expression vector) comprising the nucleic acid encoding an anti-CD3 antibody is provided (e.g., a vector for expressing the anti-CD3 antibody).

In another aspect, the invention features host cells comprising the preceding nucleic acids and/or vectors. In some embodiments, the host cell is a mammalian cell (e.g., a Chinese hamster ovary (CHO) cell). In other embodiments, the host cell is a prokaryotic cell (e.g., an E. coli cell). A method of producing any one of the preceding anti-CD3 antibodies is also provided, the method comprising culturing the host cell that produces the anti-CD3 antibody and recovering the anti-CD3 antibody from the host cell or the culture medium.

In some aspects, any one of the preceding anti-CD3 antibodies can be for use as a medicament. In some embodiments, any one of the preceding anti-CD3 antibodies can be for use in treating or delaying progression of a cell proliferative disorder or an autoimmune disorder in a subject in need thereof. In some embodiments, any one of the preceding anti-CD3 antibodies can be for use in enhancing immune function in a subject having a cell proliferative disorder or an autoimmune disorder.

In some aspects, the invention features the use of any one of the preceding anti-CD3 antibodies in the manufacture of a medicament for treating or delaying progression of a cell proliferative disorder or an autoimmune disorder. In some aspects, the invention features the use of any one of the preceding anti-CD3 antibodies in the manufacture of a medicament for enhancing immune function in a subject having a cell proliferative disorder or an autoimmune disorder.

A further aspect of the invention is a method of treating or delaying the progression of a cell proliferative disorder or an autoimmune disorder in a subject in need thereof, the method comprising administering to the subject an effective amount any one of the preceding anti-CD3 antibodies. In another aspect, the invention features a method of enhancing immune function in a subject having a cell proliferative disorder or an autoimmune disorder, the method comprising administering to the subject any one of the preceding anti-CD3 antibodies. In some embodiments, the anti-CD3 antibody binds to (a) a CD3 molecule located on an immune effector cell and (b) a second biological molecule located on a target cell other than the immune effector cell. In some embodiments, the anti-CD3 antibody activates the immune effector cell following binding to (a) and (b). In some embodiments, the activated immune effector cell is capable of exerting a cytotoxic effect and/or an apoptotic effect on the target cell. In some embodiments, the anti-CD3 antibody is administered to the subject in a dosage of about 0.01 mg/kg to about 10 mg/kg. In some embodiments, the anti-CD3 antibody is administered to the subject in a dosage of about 0.1 mg/kg to about 10 mg/kg. In some embodiments, the anti-CD3 antibody is administered to the subject in a dosage of about 1 mg/kg. In some embodiments, the anti-CD3 antibody is administered subcutaneously, intravenously, intramuscularly, topically, orally, transdermally, intraperitoneally, intraorbitally, by implantation, by inhalation, intrathecally, intraventricularly, or intranasally. In some embodiments, the anti-CD3 antibody is administered subcutaneously. In some embodiments, the anti-CD3 antibody is administered intravenously.

In some embodiments, the method further comprises administering to the subject a PD-1 axis binding antagonist or an additional therapeutic agent. In some embodiments, the additional therapeutic agent is administered prior to or subsequent to the administration of the anti-CD3 antibody. In some embodiments, the additional therapeutic agent is administered concurrently with the anti-CD3 antibody. In some embodiments, the PD-1 axis binding antagonist is selected from the group consisting of a PD-1 binding antagonist, a PD-1 binding antagonist, and a PD-L2 binding antagonist.

In some embodiments, the PD-1 axis binding antagonist is a PD-1 binding antagonist. In some embodiments, the PD-1 binding antagonist is an anti-PD-1 antibody, antigen-binding fragment thereof, immunoadhesin, fusion protein, oligopeptide, or other molecule that decreases, blocks, inhibits, abrogates, or interferes with signal transduction resulting from the interaction of PD-1 with PD-1 and/or PD-L2. In some embodiments, the PD-1 binding antagonist is an anti-PD-1 antibody. In a specific embodiment, the PD-1 binding antagonist is MDX-1106 (nivolumab). In another specific embodiment, the PD-1 binding antagonist is MK-3475 (pembrolizumab). In another specific embodiment, the PD-1 binding antagonist is CT-011 (pidilizumab). In another specific embodiment, the PD-1 binding antagonist is AMP-224. In another specific embodiment, the PD-1 binding antagonist is MED1-0680. In another specific embodiment, the PD-1 binding antagonist is PDR001. In another specific embodiment, the PD-1 binding antagonist is REGN2810. In another specific embodiment, the PD-1 binding antagonist is BGB-108.

In other embodiments, the PD-1 axis binding antagonist is a PD-1 binding antagonist. In some embodiments, the PD-1 binding antagonist is an anti-PD-L1 antibody, antigen binding fragment thereof, immunoadhesin, fusion protein, oligopeptide, or other molecule that decreases, blocks, inhibits, abrogates, or interferes with signal transduction resulting from the interaction of PD-1 with one or more of its binding partners, such as PD-1, B7-1. In some embodiments, the PD-L1 binding antagonist is an anti-PD-L1 antibody. In still another specific embodiment, the anti-PD-L1 antibody is MPDL3280A (atezolizumab). In a specific embodiment, the anti-PD-1 antibody is YW243.55.S70. In another specific embodiment, the anti-PD-1 antibody is MDX-1105. In another specific embodiment, the anti PD-L1 antibody is MSB0015718C. In still another specific embodiment, the anti-PD-L1 antibody is MED4736.

In other embodiments, the PD-1 axis binding antagonist is a PD-L2 binding antagonist. In some embodiments, the PD-L2 binding antagonist is an anti-PD-L2 antibody, antigen binding fragment thereof, immunoadhesin, fusion protein, oligopeptide, or other molecule that decreases, blocks, inhibits, abrogates, or interferes with signal transduction resulting from the interaction of PD-L2 with one or more of its binding partners, such as PD-1. In some embodiments, the PD-L2 binding antagonist is an anti-PD-L2 antibody. In some embodiments, the PD-L2 binding antagonist is an immunoadhesin.

In some aspects, the invention features a method of treating or delaying the progression of a cell proliferative disorder or an autoimmune disorder in a subject in need thereof, the method comprising administering to the subject an anti-CD3 antibody and a PD-1 axis binding antagonist, wherein the anti-CD3 antibody comprises an anti-CD3 arm and an anti-Ly6G6D arm. In some aspects, the invention features a method of enhancing immune function in a subject having a cell proliferative disorder or an autoimmune disorder, the method comprising administering to the subject an anti-CD3 antibody and a PD-1 axis binding antagonist, wherein the anti-CD3 antibody comprises an anti-CD3 arm and an anti-Ly6G6D arm (i.e., a Ly6G6D TDB antibody). In some embodiments, the anti-CD3 arm comprises a first binding domain comprising (i) a VH domain comprising an amino acid sequence of SEQ ID NO: 7, and (ii) a VL domain comprising an amino acid sequence of SEQ ID NO: 8. In some embodiments, the method includes administering to the subject an anti-CD3 antibody, wherein the anti-CD3 antibody comprises (i) an anti-CD3 arm having a VH domain comprising an amino acid sequence of SEQ ID NO: 7 and a VL domain comprising an amino acid sequence of SEQ ID NO: 8 and (ii) an anti-Ly6G6D arm (i.e., a Ly6G6D TDB antibody), and a PD-1 axis binding antagonist that is an anti-PD-1 antibody.

In other embodiments, an anti-CD3 antibody (e.g., a Ly6G6D TDB) is co-administered (concurrently, as a single or multiple (e.g., 1, 2, 3, 4, 5, or 6 or more) compositions (e.g., formulations)) with one or more (e.g., 1, 2, 3, 4, 5, 6, 7, 8, 9, 10, or 11) additional therapeutic agents selected from FOLFOX (oxaliplatin (ELOXATIN™) combined with 5-fluorouracil and leucovorin), capecitabine (XELODA®), 5-fluorouracil (5-FU), CapeOx (XELOX®; capecitabine with oxaliplatin), leucovorin (folinic acid), bevacizumab (AVASTIN®), cetuximab (ERBITUX®), panitumumab (VECTIBIX®), regorafenib (STIVARGA®), irinotecan (CPT-11; CAMPTOSAR®), and FLOX (5-fluorouracil with oxaliplatin). In other embodiments, an anti-CD3 antibody (e.g., a Ly6G6D TDB) is administered before one or more additional therapeutic agents, such as any one, two, three, four, five, six, seven, eight, nine, ten, or all eleven of the following: FOLFOX (oxaliplatin (ELOXATIN™) combined with 5-fluorouracil and leucovorin), capecitabine (XELODA®), 5-fluorouracil (5-FU), CapeOx (XELOX®; capecitabine with oxaliplatin), leucovorin (folinic acid), bevacizumab (AVASTIN®), cetuximab (ERBITUX®), panitumumab (VECTIBIX®), regorafenib (STIVARGA®), irinotecan (CPT-11; CAMPTOSAR®), and FLOX (5-fluorouracil with oxaliplatin). In other embodiments, an anti-CD3 antibody (e.g., a Ly6G6D TDB) is administered after one or more additional therapeutic agents, such as any one, two, three, four, five, six, seven, eight, nine, ten, or all eleven of the following: FOLFOX (oxaliplatin (ELOXATIN™) combined with 5-fluorouracil and leucovorin), capecitabine (XELODA®), 5-fluorouracil (5-FU), CapeOx (XELOX®; capecitabine with oxaliplatin), leucovorin (folinic acid), bevacizumab (AVASTIN®), cetuximab (ERBITUX®), panitumumab (VECTIBIX®), regorafenib (STIVARGA®), irinotecan (CPT-11; CAMPTOSAR®), and FLOX (5-fluorouracil with oxaliplatin).

In some embodiments, the method further comprises administering to the subject a glucocorticoid. In some embodiments, the glucocorticoid is selected from the group consisting of dexamethasone, hydrocortisone, cortisone, prednisolone, prednisone, methylprednisone, triamcinolone, paramethasone, betamethasone, fludrocortisone, and pharmaceutically acceptable esters, salts, and complexes thereof. In some embodiments, the glucocorticoid is dexamethasone. In some embodiments, the glucocorticoid is a pharmaceutically acceptable ester, salt, or complex of dexamethasone.

In some embodiments, the method further comprises administering to the subject rituximab. In some embodiments, the method further comprises administering to the subject obinutuzumab. In some embodiments, the method further comprises administering to the subject an antibody-drug conjugate (ADC).

In any of the preceding uses or methods, the cell proliferative disorder can be cancer. In some embodiments, the cancer is selected from the group consisting of esophageal cancer, stomach cancer, small intestine cancer, large intestine cancer, colorectal cancer, breast cancer, non-small cell lung cancer, non-Hodgkin's lymphoma (NHL), B cell lymphoma, B cell leukemia, multiple myeloma, renal cancer, prostate cancer, liver cancer, head and neck cancer, melanoma, ovarian cancer, mesothelioma, glioblastoma, germinal-center B-cell-like (GCB) DLBCL, activated B-cell-like (ABC) DLBCL, follicular lymphoma (FL), mantle cell lymphoma (MCL), acute myeloid leukemia (AML), chronic lymphoid leukemia (CLL), marginal zone lymphoma (MZL), small lymphocytic leukemia (SLL), lymphoplasmacytic lymphoma (LL), Waldenstrom macroglobulinemia (WM), central nervous system lymphoma (CNSL), Burkitt's lymphoma (BL), B-cell prolymphocytic leukemia, Splenic marginal zone lymphoma, Hairy cell leukemia, Splenic lymphoma/leukemia, unclassifiable, Splenic diffuse red pulp small B-cell lymphoma, Hairy cell leukemia variant, Waldenström macroglobulinemia, Heavy chain diseases, a Heavy chain disease, γ Heavy chain disease, μ Heavy chain disease, Plasma cell myeloma, Solitary plasmacytoma of bone, Extraosseous plasmacytoma, Extranodal marginal zone lymphoma of mucosa-associated lymphoid tissue (MALT lymphoma), Nodal marginal zone lymphoma, Pediatric nodal marginal zone lymphoma, Pediatric follicular lymphoma, Primary cutaneous follicle centre lymphoma, T-cell/histiocyte rich large B-cell lymphoma, Primary DLBCL of the CNS, Primary cutaneous DLBCL, leg type, EBV-positive DLBCL of the elderly, DLBCL associated with chronic inflammation, Lymphomatoid granulomatosis, Primary mediastinal (thymic) large B-cell lymphoma, Intravascular large B-cell lymphoma, ALK-positive large B-cell lymphoma, Plasmablastic lymphoma, Large B-cell lymphoma arising in HHV8-associated multicentric Castleman disease, Primary effusion lymphoma: B-cell lymphoma, unclassifiable, with features intermediate between diffuse large B-cell lymphoma and Burkitt lymphoma, and B-cell lymphoma, unclassifiable, with features intermediate between diffuse large B-cell lymphoma and classical Hodgkin lymphoma.

In some embodiments, the cancer is esophageal cancer. In some embodiments, the cancer is an adenocarcinoma, for example, a metatstatic adenocarcinoma (e.g., a colorectal adenocarcinoma, a gastric adenocarcinoma, or a pancreatic adenocarcinoma).

In any of the preceding uses or methods, the autoimmune disorder can be selected from the group consisting of rheumatoid arthritis, juvenile rheumatoid arthritis, systemic lupus erythematosus (SLE), Wegener's disease, inflammatory bowel disease, idiopathic thrombocytopenic purpura (ITP), thrombotic thrombocytopenic purpura (TTP), autoimmune thrombocytopenia, multiple sclerosis, psoriasis, IgA nephropathy, IgM polyneuropathies, myasthenia gravis, vasculitis, diabetes mellitus, Reynaud's syndrome, Sjorgen's syndrome, glomerulonephritis, Neuromyelitis Optica (NMO), and IgG neuropathy.

In another aspect, the invention features a kit comprising: (a) a composition comprising any one of the preceding anti-CD3 antibodies and (b) a package insert comprising instructions for administering the composition to a subject to treat or delay progression of a cell proliferative disorder.

In any of the preceding uses or methods, the subject can be a human.

BRIEF DESCRIPTION OF THE DRAWINGS

FIG. 1A shows the amino acid sequence of the light chain variable domain (VL) of the anti-CD3 antibody 38E4v11 (SEQ ID NO: 8). HVR-L1 (SEQ ID NO: 4), HVR-L2 (SEQ ID NO: 5), and HVR-L3 (SEQ ID NO: 6) sequences are delimited by the denoted boxes.

FIG. 1B shows the amino acid sequence of the heavy chain variable domain (VH) of the anti-CD3 antibody 38E4v11 (SEQ ID NO: 7). HVR-H1 (SEQ ID NO: 1), HVR-H2 (SEQ ID NO: 2), and HVR-H3 (SEQ ID NO: 3) sequences are delimited by the denoted boxes.

DETAILED DESCRIPTION OF EMBODIMENTS OF THE INVENTION

I. Definitions

Figure 2:
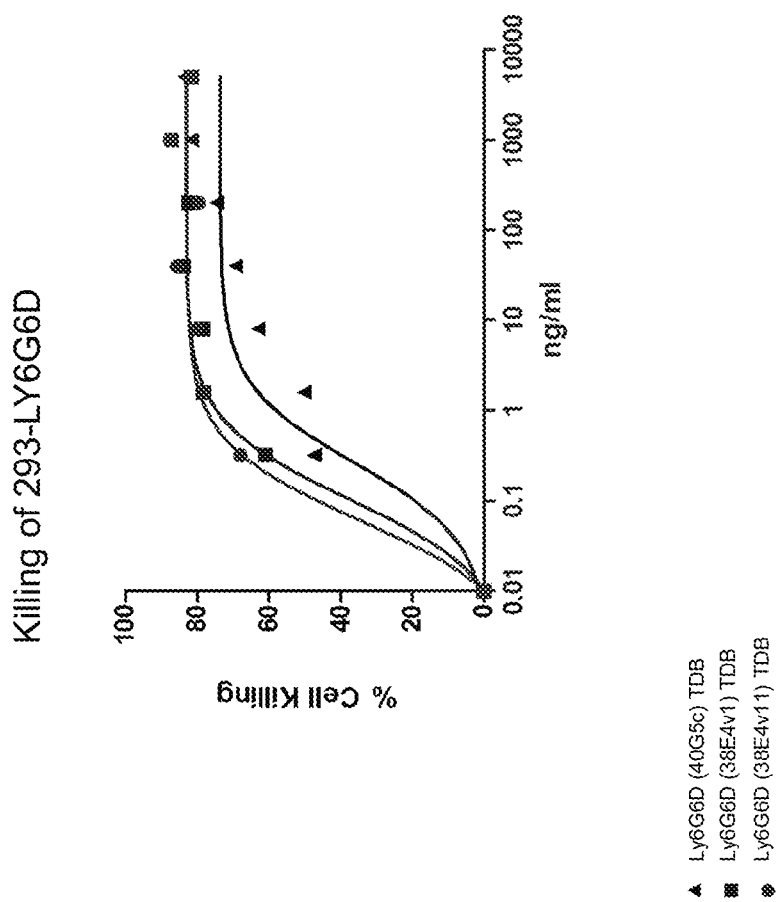
FIG. 2 is a graph showing the percentage of Ly6G6D-transfected 293 target cells killed in an in vitro target cell killing assay as a function of Ly6G6D TDB antibody concentration for three different Ly6G6D TDBs having different anti-CD3 arms: Ly6G6D (38E4v11) TDB, Ly6G6D (40G5c) TDB, and Ly6G6D (38E4v1) TDB.

The term "about" as used herein refers to the usual error range for the respective value readily known to the skilled person in this technical field. Reference to "about" a value or parameter herein includes (and describes) embodiments that are directed to that value or parameter per se.

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant ($K_D$). Affinity can be measured by common methods known in the art, including those described herein. Specific illustrative and exemplary embodiments for measuring binding affinity are described in the following.

An "affinity matured" antibody refers to an antibody with one or more alterations in one or more hypervariable regions (HVRs), compared to a parent antibody which does not possess such alterations, such alterations resulting in an improvement in the affinity of the antibody for antigen.

The terms "anti-CD3 antibody" and "an antibody that binds to CD3" refer to an antibody that is capable of binding CD3 with sufficient affinity such that the antibody is useful as a diagnostic and/or therapeutic agent in targeting CD3. In one embodiment, the extent of binding of an anti-CD3 antibody to an unrelated, non-CD3 protein is less than about 10% of the binding of the antibody to CD3 as measured, e.g., by a radioimmunoassay (RIA). In certain embodiments, an antibody that binds to CD3 has a dissociation constant ($K_D$) of $\leq 1$ µM, $\leq 100$ nM, $\leq 10$ nM, $\leq 1$ nM, $\leq 0.1$ nM, $\leq 0.01$ nM, or $\leq 0.001$ nM (e.g., $10^{-8}$M or less, e.g., from $10^{-8}$M to $10^{-13}$M, e.g., from $10^{-9}$M to $10^{-13}$M). In certain embodiments, an anti-CD3 antibody binds to an epitope of CD3 that is conserved among CD3 from different species.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies; linear antibodies; single-chain antibody molecules (e.g., scFv); and multispecific antibodies formed from antibody fragments.

By "binding domain" is meant a part of a compound or a molecule that specifically binds to a target epitope, antigen, ligand, or receptor. Binding domains include but are not limited to antibodies (e.g., monoclonal, polyclonal, recombinant, humanized, and chimeric antibodies), antibody fragments or portions thereof (e.g., Fab fragments, Fab'$_2$, scFv antibodies, SMIP, domain antibodies, diabodies, minibodies, scFv-Fc, affibodies, nanobodies, and VH and/or VL domains of antibodies), receptors, ligands, aptamers, and other molecules having an identified binding partner.

A "chemotherapeutic agent" is a chemical compound useful in the treatment of cancer. Examples of chemotherapeutic agents include alkylating agents such as thiotepa and cyclosphosphamide (CYTOXAN®); akyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-

TM1); eleutherobin; pancratistatin; a sarcodictyin; spongistatin; nitrogen mustards such as chlorambucil, chlornaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omegaII (see, e.g., Nicolaou et al., *Angew. Chem Intl. Ed. Engl.*, 33:183-186 (1994)); CDP323, an oral alpha-4 integrin inhibitor; dynemicin, including dynemicin A; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycins, dactinomycin, daunorubicin, detorubicin, 6-diazo-5-oxo-L-norleucine, doxorubicin (including ADRIAMYCIN®, morpholino-doxorubicin, cyanomorpholino-doxorubicin, 2-pyrrolino-doxorubicin, doxorubicin HCl liposome injection (DOXIL®), liposomal doxorubicin TLC D-99 (MYOCET®), peglylated liposomal doxorubicin (CAELYX®), and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate, gemcitabine (GEMZAR®), tegafur (UFTORAL®), capecitabine (XELODA®), an epothilone, and 5-fluorouracil (5-FU); combretastatin; folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethyihydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2''-trichlorotriethyamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); thiotepa; taxoid, e.g., paclitaxel (TAXOL®, Bristol-Myers Squibb Oncology, Princeton, N.J.), albumin-engineered nanoparticle formulation of paclitaxel (ABRAXANE™), and docetaxel (TAXOTERE®, Rhome-Poulene Rorer, Antony, France); chloranbucil; 6-thioguanine; mercaptopurine; methotrexate; platinum agents such as cisplatin, oxaliplatin (e.g., ELOXATIN®), and carboplatin; vincas, which prevent tubulin polymerization from forming microtubules, including vinblastine (VELBAN®), vincristine (ONCOVIN®), vindesine (ELDISINE®, FILDESIN®), and vinorelbine (NAVELBINE®); etoposide (VP-16); ifosfamide; mitoxantrone; leucovorin; novantrone; edatrexate; daunomycin; aminopterin; ibandronate; topoisomerase inhibitor RFS 2000; difluoromethylornithine (DMFO); retinoids such as retinoic acid, including bexarotene (TARGRETIN®); bisphosphonates such as clodronate (for example, BONEFOS® or OSTAC®), etidronate (DIDROCAL®), NE-58095, zoledronic acid/zoledronate (ZOMETA®), alendronate (FOSAMAX®), pamidronate (AREDIA®), tiludronate (SKELID®), or risedronate (ACTONEL®); troxacitabine (a 1,3-dioxolane nucleoside cytosine analog); antisense oligonucleotides, particularly those that inhibit expression of genes in signaling pathways implicated in aberrant cell proliferation, such as, for example, PKC-alpha, Raf, H-Ras, and epidermal growth factor receptor (EGF-R) (e.g., erlotinib (Tarceva™)); and VEGF-A that reduce cell proliferation; vaccines such as THERATOPE® vaccine and gene therapy vaccines, for example, ALLOVECTIN® vaccine, LEUVECTIN® vaccine, and VAXID® vaccine; topoisomerase 1 inhibitor (e.g., LURTOTECAN®); rmRH (e.g., ABARELIX®); BAY439006 (sorafenib; Bayer); SU-11248 (sunitinib, SUTENT®, Pfizer); perifosine, COX-2 inhibitor (e.g. celecoxib or etoricoxib), proteosome inhibitor (e.g. PS341); bortezomib (VELCADE®); CCI-779; tipifarnib (R11577); orafenib, ABT510; Bcl-2 inhibitor such as oblimersen sodium (GENASENSE®); pixantrone; EGFR inhibitors; tyrosine kinase inhibitors; serine-threonine kinase inhibitors such as rapamycin (sirolimus, RAPAMUNE®); farnesytransferase inhibitors such as lonafarnib (SCH 6636, SARASAR™); and pharmaceutically acceptable salts, acids or derivatives of any of the above; as well as combinations of two or more of the above such as CHOP, an abbreviation for a combined therapy of cyclophosphamide, doxorubicin, vincristine, and prednisolone; and FOLFOX, an abbreviation for a treatment regimen with oxaliplatin (ELOXATIN™) combined with 5-FU and leucovorin, and pharmaceutically acceptable salts, acids or derivatives of any of the above; as well as combinations of two or more of the above.

Chemotherapeutic agents as defined herein include "anti-hormonal agents" or "endocrine therapeutics" which act to regulate, reduce, block, or inhibit the effects of hormones that can promote the growth of cancer. They may be hormones themselves, including, but not limited to: anti-estrogens and selective estrogen receptor modulators (SERMs), including, for example, tamoxifen (including NOLVADEX® tamoxifen), raloxifene, droloxifene, 4-hydroxytamoxfen, trioxifene, keoxifene, LY117018, onapristone, and FARESTON® toremifene; aromatase inhibitors that inhibit the enzyme aromatase, which regulates estrogen production in the adrenal glands, such as, for example, 4(5)-imidazoles, aminoglutethimide, MEGASE® megestrol acetate, AROMASIN® exemestane, formestanie, fadrozole, RIVISOR® vorozole, FEMARA® letrozole, and ARIMIDEX® anastrozole; and anti-androgens such as flutamide, nilutamide, bicalutamide, leuprolide, and goserelin; as well as troxacitabine (a 1,3-dioxolane nucleoside cytosine analog); antisense oligonucleotides, particularly those which inhibit expression of genes in signaling pathways implicated in abherant cell proliferation, such as, for example, PKC-alpha, Raf and H-Ras; ribozymes such as a VEGF expression inhibitor (e.g., ANGIOZYME® ribozyme) and a HER2 expression inhibitor; vaccines such as gene therapy vaccines, for example, ALLOVECTIN® vaccine, LEUVECTIN® vaccine, and VAXID® vaccine; PROLEUKIN® rIL-2; LURTOTECAN® topoisomerase 1 inhibitor; ABARELIX® rmRH; Vinorelbine and Esperamicins (see U.S. Pat. No. 4,675,187), and pharmaceutically acceptable salts, acids or derivatives of any of the above; as well as combinations of two or more of the above.

The term "chimeric" antibody refers to an antibody in which a portion of the heavy and/or light chain is derived from a particular source or species, while the remainder of the heavy and/or light chain is derived from a different source or species.

The term "cluster of differentiation 3" or "CD3," as used herein, refers to any native CD3 from any vertebrate source, including mammals such as primates (e.g. humans) and rodents (e.g., mice and rats), unless otherwise indicated, including, for example, CD3ε, CD3γ, CD3α, and CD3β chains. The term encompasses "full-length," unprocessed CD3 (e.g., unprocessed or unmodified CD3ε or CD3γ), as well as any form of CD3 that results from processing in the cell. The term also encompasses naturally occurring variants of CD3, including, for example, splice variants or allelic variants. CD3 includes, for example, human CD3ε protein (NCBI RefSeq No. NP_000724), which is 207 amino acids in length, and human CD3γ protein (NCBI RefSeq No. NP_000064), which is 182 amino acids in length.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., IgG1, IgG2, IgG3, IgG4, $IgA_1$, and $IgA_2$. The heavy chain constant domains that correspond to the different classes of immunoglobulins are called α, δ, ε, γ, and μ, respectively.

It is understood that aspects and embodiments of the invention described herein include "comprising," "consisting," and "consisting essentially of" aspects and embodiments.

The term "cytotoxic agent" as used herein refers to a substance that inhibits or prevents a cellular function and/or causes cell death or destruction. Cytotoxic agents include, but are not limited to, radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu); chemotherapeutic agents or drugs (e.g., methotrexate, adriamicin, vinca alkaloids (vincristine, vinblastine, etoposide), doxorubicin, melphalan, mitomycin C, chlorambucil, daunorubicin or other intercalating agents); growth inhibitory agents; enzymes and fragments thereof such as nucleolytic enzymes; antibiotics; toxins such as small molecule toxins or enzymatically active toxins of bacterial, fungal, plant or animal origin, including fragments and/or variants thereof; and the various antitumor or anti-cancer agents disclosed below.

A "disorder" is any condition that would benefit from treatment including, but not limited to, chronic and acute disorders or diseases including those pathological conditions which predispose the mammal to the disorder in question.

The terms "cell proliferative disorder" and "proliferative disorder" refer to disorders that are associated with some degree of abnormal cell proliferation. In one embodiment, the cell proliferative disorder is cancer. In one embodiment, the cell proliferative disorder is a tumor.

The terms "cancer" and "cancerous" refer to or describe the physiological condition in mammals that is typically characterized by unregulated cell growth. Examples of cancer include but are not limited to, adenocarcinoma (e.g., colorectal adenocarcinoma, gastric adenocarcinoma, or pancreatic adenocarcinoma), which may be metastatic adenocarcinoma (e.g., metastatic colorectal adenocarcinoma, metastatic gastric adenocarcinoma, or metastatic pancreatic adenocarcinoma), carcinoma, lymphoma, blastoma, sarcoma, and leukemia or lymphoid malignancies. More particular examples of such cancers include, but are not limited to, esophageal cancer, small intestine cancer, large intestine cancer, squamous cell cancer (e.g., epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer and gastrointestinal stromal cancer, pancreatic cancer, glioblastoma, cervical cancer, ovarian cancer, liver cancer, bladder cancer, cancer of the urinary tract, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, melanoma, superficial spreading melanoma, lentigo maligna melanoma, acral lentiginous melanomas, nodular melanomas, multiple myeloma and B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); hairy cell leukemia; chronic myeloblastic leukemia; and post-transplant lymphoproliferative disorder (PTLD), as well as abnormal vascular proliferation associated with phakomatoses, edema (such as that associated with brain tumors), Meigs' syndrome, brain, as well as head and neck cancer, and associated metastases. In certain embodiments, cancers that are amenable to treatment by the antibodies of the invention include adenocarcinomas (e.g., colorectal adenocarcinoma, gastric adenocarcinoma, or pancreatic adenocarcinoma), which may be metastatic adenocarcinomas (e.g., metastatic colorectal adenocarcinoma, metastatic gastric adenocarcinoma, or metastatic pancreatic adenocarcinoma), esophageal cancer, stomach cancer, small intestine cancer, large intestine cancer, colorectal cancer, breast cancer, colorectal cancer, rectal cancer, non-small cell lung cancer, glioblastoma, non-Hodgkins lymphoma (NHL), renal cell cancer, prostate cancer, liver cancer, pancreatic cancer, soft-tissue sarcoma, kaposi's sarcoma, carcinoid carcinoma, head and neck cancer, ovarian cancer, mesothelioma, and multiple myeloma. In some embodiments, the cancer is selected from: adenocarcinomas (e.g., colorectal adenocarcinoma, gastric adenocarcinoma, or pancreatic adenocarcinoma), which may be metastatic adenocarcinomas (e.g., metastatic colorectal adenocarcinoma, metastatic gastric adenocarcinoma, or metastatic pancreatic adenocarcinoma), esophageal cancer, stomach cancer, small intestine cancer, large intestine cancer, small cell lung cancer, glibastoma, neuroblastomas, melanoma, breast carcinoma, gastric cancer, colorectal cancer (CRC), and hepatocellular carcinoma. Yet, in some embodiments, the cancer is selected from: adenocarcinomas (e.g., colorectal adenocarcinoma, gastric adenocarcinoma, or pancreatic adenocarcinoma), esophageal cancer, stomach cancer, small intestine cancer, large intestine cancer, non-small cell lung cancer, colorectal cancer, glioblastoma and breast carcinoma, including metastatic forms of those cancers. In other embodiments, the cancer is selected from a class of mature B-Cell cancers excluding Hodgkin's Lymphoma but including germinal-center B-cell-like (GCB) DLBCL, activated B-cell-like (ABC) DLBCL, follicular lymphoma (FL), mantle cell lymphoma (MCL), acute myeloid leukemia (AML), chronic lymphoid leukemia (CLL), marginal zone lymphoma (MZL), small lymphocytic leukemia (SLL), lymphoplasmacytic lymphoma (LL), Waldenstrom macroglobulinemia (WM), central nervous system lymphoma (CNSL), Burkitt's lymphoma (BL), B-cell prolymphocytic leukemia, Splenic marginal zone lymphoma, Hairy cell leukemia, Splenic lymphoma/leukemia, unclassifiable, Splenic diffuse red pulp small B-cell lymphoma, Hairy cell leukemia variant, Waldenström macroglobulinemia, Heavy chain diseases, a Heavy chain disease, γ Heavy chain disease, μ Heavy chain disease, Plasma cell myeloma, Solitary plasmacytoma of bone, Extraosseous plasmacytoma, Extranodal marginal zone lymphoma of mucosa-associated lymphoid tissue (MALT lymphoma), Nodal marginal zone lymphoma, Pediatric nodal marginal zone lymphoma, Pediatric follicular lymphoma, Primary cutaneous follicle centre lymphoma, T-cell/histiocyte rich large B-cell lymphoma, Primary DLBCL of the CNS, Primary cutaneous DLBCL, leg type, EBV-positive DLBCL of the elderly, DLBCL associated with chronic inflammation, Lymphomatoid granulomatosis, Primary mediastinal (thymic) large B-cell lymphoma, Intravascular large B-cell lymphoma, ALK-positive large B-cell lymphoma, Plasmablastic lymphoma, Large B-cell lymphoma arising in HHV8-associated multicentric Castleman disease, Primary effusion lymphoma: B-cell lymphoma, unclassifiable, with features intermediate between diffuse large B-cell lymphoma and Burkitt lymphoma, and B-cell lymphoma, unclassifiable, with features intermediate between diffuse large B-cell lymphoma and classical Hodgkin lymphoma.

"Tumor," as used herein, refers to all neoplastic cell growth and proliferation, whether malignant or benign, and all pre-cancerous and cancerous cells and tissues. The terms "cancer", "cancerous", "cell proliferative disorder", "proliferative disorder," and "tumor" are not mutually exclusive as referred to herein.

The term "tumor antigen," as used herein, may be understood as those antigens that are presented on tumor cells. These antigens can be presented on the cell surface with an extracellular part, which is often combined with a transmembrane and cytoplasmic part of the molecule. These antigens can sometimes be presented only by tumor cells and never by the normal ones. Tumor antigens can be exclusively expressed on tumor cells or might represent a tumor-specific mutation compared to normal cells. In this case, they are called tumor-specific antigens. More common are tumor antigens that are presented by tumor cells and normal cells, and they are called tumor-associated antigens. These tumor-associated antigens can be overexpressed compared to normal cells or are accessible for antibody binding in tumor cells due to the less compact structure of the tumor tissue compared to normal tissue. Tumor antigens may exhibit inconsistent expression or may be expressed in low copy number on certain types of tumor cells. In instances in which a targeted tumor antigen is expressed in low copy number (i.e., weakly expressed) on tumor cells, it may be desirable to use a TDB antibody of the invention having a high-affinity arm against CD3 or another molecule located on an immune effector cell. In one aspect, the tumor antigen is selected from those set forth in Table 1 below.

"Effector functions" refer to those biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation.

An "effective amount" of a compound, for example, an anti-CD3 antibody of the invention or a composition (e.g., pharmaceutical composition) thereof, is at least the minimum amount required to achieve the desired therapeutic or prophylactic result, such as a measurable improvement or prevention of a particular disorder (e.g., a cell proliferative disorder, e.g., cancer). An effective amount herein may vary according to factors such as the disease state, age, sex, and weight of the patient, and the ability of the antibody to elicit a desired response in the individual. An effective amount is also one in which any toxic or detrimental effects of the treatment are outweighed by the therapeutically beneficial effects. For prophylactic use, beneficial or desired results include results such as eliminating or reducing the risk, lessening the severity, or delaying the onset of the disease, including biochemical, histological and/or behavioral symptoms of the disease, its complications and intermediate pathological phenotypes presenting during development of the disease. For therapeutic use, beneficial or desired results include clinical results such as decreasing one or more symptoms resulting from the disease, increasing the quality of life of those suffering from the disease, decreasing the dose of other medications required to treat the disease, enhancing effect of another medication such as via targeting, delaying the progression of the disease, and/or prolonging survival. In the case of cancer or tumor, an effective amount of the drug may have the effect in reducing the number of cancer cells; reducing the tumor size; inhibiting (i.e., slow to some extent or desirably stop) cancer cell infiltration into peripheral organs; inhibit (i.e., slow to some extent and desirably stop) tumor metastasis; inhibiting to some extent tumor growth; and/or relieving to some extent one or more of the symptoms associated with the disorder. An effective amount can be administered in one or more administrations. For purposes of this invention, an effective amount of drug, compound, or pharmaceutical composition is an amount sufficient to accomplish prophylactic or therapeutic treatment either directly or indirectly. As is understood in the clinical context, an effective amount of a drug, compound, or pharmaceutical composition may or may not be achieved in conjunction with another drug, compound, or pharmaceutical composition. Thus, an "effective amount" may be considered in the context of administering one or more therapeutic agents, and a single agent may be considered to be given in an effective amount if, in conjunction with one or more other agents, a desirable result may be or is achieved.

The term "Fc region" herein is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., *Sequences of Proteins of Immunological Interest*, 5th Ed. Public Health Service, National Institutes of Health, Bethesda, Md., 1991.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

The terms "full-length antibody," "intact antibody," and "whole antibody" are used herein interchangeably to refer to an antibody having a structure substantially similar to a native antibody structure or having heavy chains that contain an Fc region as defined herein.

A "growth inhibitory agent" when used herein refers to a compound or composition which inhibits growth of a cell either in vitro or in vivo. In one embodiment, growth inhibitory agent is growth inhibitory antibody that prevents or reduces proliferation of a cell expressing an antigen to which the antibody binds. In another embodiment, the growth inhibitory agent may be one which significantly reduces the percentage of cells in S phase. Examples of growth inhibitory agents include agents that block cell cycle progression (at a place other than S phase), such as agents that induce G1 arrest and M-phase arrest. Classical M-phase blockers include the vincas (vincristine and vinblastine), taxanes, and topoisomerase II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in Mendelsohn and Israel, eds., The Molecular Basis of Cancer, Chapter 1, entitled "Cell cycle regulation, oncogenes, and antineoplastic drugs" by Murakami et al. (W.B. Saunders, Philadelphia, 1995), e.g., p. 13. The taxanes (paclitaxel and docetaxel) are anticancer drugs both derived from the yew tree. Docetaxel (TAXOTERE®, Rhone-Poulenc Rorer), derived from the European yew, is a semisynthetic analogue of paclitaxel (TAXOL®, Bristol-Myers Squibb). Paclitaxel and docetaxel promote the assembly of microtubules from tubulin dimers and stabilize microtubules by preventing depolymerization, which results in the inhibition of mitosis in cells.

The term "HER2-positive" cancer comprises cancer cells which have higher than normal levels of HER2. Examples of HER2-positive cancer include HER2-positive breast cancer and HER2-positive gastric cancer. Optionally, HER2-positive cancer has an immunohistochemistry (IHC) score of 2+ or 3+ and/or an in situ hybridization (ISH) amplification ratio 22.0.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues. Human antibodies can be produced using various techniques known in the art, including phage-display libraries. Hoogenboom and Winter, *J. Mol. Biol.*, 227:381 (1991); Marks et al., *J. Mol. Biol.*, 222:581 (1991). Also available for the preparation of human monoclonal antibodies are methods described in Cole et al., *Monoclonal Antibodies and Cancer Therapy*, Alan R. Liss, p. 77 (1985); Boerner et al., *J. Immunol.*, 147(1):86-95 (1991). See also van Dijk and van de Winkel, *Curr. Opin. Pharmacol.*, 5:368-74 (2001).

Human antibodies can be prepared by administering the antigen to a transgenic animal that has been modified to produce such antibodies in response to antigenic challenge, but whose endogenous loci have been disabled, e.g., immunized xenomice (see, e.g., U.S. Pat. Nos. 6,075,181 and 6,150,584 regarding XENOMOUSE™ technology). See also, for example, Li et al., *Proc. Natl. Acad. Sci. USA*, 103:3557-3562 (2006) regarding human antibodies generated via a human B-cell hybridoma technology.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., *Sequences of Proteins of Immunological Interest*, Fifth Edition, NIH Publication 91-3242, Bethesda Md. (1991), vols. 1-3. In one embodiment, for the VL, the subgroup is subgroup kappa I as in Kabat et al., supra. In one embodiment, for the VH, the subgroup is subgroup III as in Kabat et al., supra.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "hypervariable region" or "HVR" as used herein refers to each of the regions of an antibody variable domain which are hypervariable in sequence ("complementarity determining regions" or "CDRs") and/or form structurally defined loops ("hypervariable loops") and/or contain the antigen-contacting residues ("antigen contacts"). Generally, antibodies comprise six HVRs: three in the VH (H1, H2, H3), and three in the VL (L1, L2, L3). Exemplary HVRs herein include:

(a) hypervariable loops occurring at amino acid residues 26-32 (L1), 50-52 (L2), 91-96 (L3), 26-32 (H1), 53-55 (H2), and 96-101 (H3) (Chothia and Lesk, *J. Mol. Biol.* 196:901-917 (1987));

(b) CDRs occurring at amino acid residues 24-34 (L1), 50-56 (L2), 89-97 (L3), 31-35b (H1), 50-65 (H2), and 95-102 (H3) (Kabat et al., *Sequences of Proteins of Immunological Interest*, 5th Ed. Public Health Service, National Institutes of Health, Bethesda, Md. (1991));

(c) antigen contacts occurring at amino acid residues 27c-36 (L1), 46-55 (L2), 89-96 (L3), 30-35b (H1), 47-58 (H2), and 93-101 (H3) (MacCallum et al. *J. Mol. Biol.* 262: 732-745 (1996)); and (d) combinations of (a), (b), and/or (c), including HVR amino acid residues 46-56 (L2), 47-56 (L2), 48-56 (L2), 49-56 (L2), 26-35 (H1), 26-35b (H1), 49-65 (H2), 93-102 (H3), and 94-102 (H3).

Unless otherwise indicated, HVR residues and other residues in the variable domain (e.g., FR residues) are numbered herein according to Kabat et al., supra.

An "immunoconjugate" is an antibody conjugated to one or more heterologous molecule(s), including but not limited to a cytotoxic agent.

A "subject" or an "individual" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the subject or individual is a human.

An "isolated" antibody is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman et al., *J. Chromatogr. B* 848:79-87 (2007).

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

"Isolated nucleic acid encoding an anti-CD3 antibody" refers to one or more nucleic acid molecules encoding antibody heavy and light chains (or fragments thereof), including such nucleic acid molecule(s) in a single vector or separate vectors, and such nucleic acid molecule(s) present at one or more locations in a host cell.

The term "Ly6G6D" or "lymphocyte antigen 6 complex, locus G61," as used herein, refers to any native Ly6G6D from any vertebrate source, including mammals such as primates (e.g. humans) and rodents (e.g., mice and rats), unless otherwise indicated, and encompasses "full-length," unprocessed Ly6G6D, as well as any form of Ly6G6D that results from processing in the cell. The term also encompasses naturally occurring variants of Ly6G6D, including, for example, splice variants or allelic variants. Ly6G6D is also referred to as G6D, Ly6-D, C6orf23, megakaryocyte-enhanced gene transcript 1 (MEGT1), and NG25 and is disclosed in U.S. Pat. No. 7,951,546, which is incorporated by reference herein in its entirety, as TAT201, with an amino acid sequence of SEQ ID NO: 92 and a nucleotide sequence, DNA234441, of SEQ ID NO: 36. Ly6G6D includes, for example, human Ly6G6D protein (NCBI RefSeq No. NP_067079.2), which is 133 amino acids in length.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoconal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

A "naked antibody" refers to an antibody that is not conjugated to a heterologous moiety (e.g., a cytotoxic moiety) or radiolabel. The naked antibody may be present in a pharmaceutical formulation.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain.

The term "package insert" is used to refer to instructions customarily included in commercial packages of therapeutic products, that contain information about the indications, usage, dosage, administration, combination therapy, contraindications and/or warnings concerning the use of such therapeutic products.

The term "PD-1 axis binding antagonist" refers to a molecule that inhibits the interaction of a PD-1 axis binding partner with either one or more of its binding partners, so as to remove T cell dysfunction resulting from signaling on the PD-1 signaling axis—with a result being to restore or enhance T cell function (e.g., proliferation, cytokine production, target cell killing). As used herein, a PD-1 axis binding antagonist includes a PD-1 binding antagonist, a PD-L1 binding antagonist, and a PD-L2 binding antagonist.

The term "PD-1 binding antagonist" refers to a molecule that decreases, blocks, inhibits, abrogates or interferes with signal transduction resulting from the interaction of PD-1 with one or more of its binding partners, such as PD-1, PD-L2. In some embodiments, the PD-1 binding antagonist is a molecule that inhibits the binding of PD-1 to one or more of its binding partners. In a specific embodiment, the PD-binding antagonist inhibits the binding of PD-1 to PD-L1 and/or PD-L2. For example, PD-1 binding antagonists include anti-PD-1 antibodies, antigen binding fragments thereof, immunoadhesins, fusion proteins, oligopeptides and other molecules that decrease, block, inhibit, abrogate or interfere with signal transduction resulting from the interaction of PD-1 with PD-L1 and/or PD-L2. In one embodiment, a PD-1 binding antagonist reduces the negative co-stimulatory signal mediated by or through cell surface proteins expressed on T lymphocytes, such as signaling mediated through PD-1, so as render a dysfunctional T cell less dysfunctional (e.g., enhancing effector responses to antigen recognition). In some embodiments, the PD-1 binding antagonist is an anti-PD-1 antibody. In a specific embodiment, a PD-1 binding antagonist is MDX-1106 (nivolumab). In another specific embodiment, a PD-1 binding antagonist is MK-3475 (pembrolizumab). In another specific embodiment, a PD-1 binding antagonist is CT-011 (pidilizumab). In another specific embodiment, a PD-1 binding antagonist is AMP-224. In another specific embodiment, a PD-1 binding antagonist is MED1-0680. In another specific embodiment, a PD-1 binding antagonist is PDR001. In another specific embodiment, a PD-1 binding antagonist is REGN2810. In another specific embodiment, a PD-1 binding antagonist is BGB-108.

The term "PD-L1 binding antagonist" refers to a molecule that decreases, blocks, inhibits, abrogates or interferes with signal transduction resulting from the interaction of PD-L1 with either one or more of its binding partners, such as PD-1, B7-1. In some embodiments, a PD-L1 binding antagonist is a molecule that inhibits the binding of PD-L1 to its binding partners. In a specific embodiment, the PD-L1 binding antagonist inhibits binding of PD-L1 to PD-1 and/or B7-1. In some embodiments, the PD-L1 binding antagonists include anti-PD-L1 antibodies, antigen binding fragments thereof, immunoadhesins, fusion proteins, oligopeptides and other molecules that decrease, block, inhibit, abrogate or interfere with signal transduction resulting from the interaction of PD-L1 with one or more of its binding partners, such as PD-1, B7-1. In one embodiment, a PD-L1 binding antagonist reduces the negative co-stimulatory signal mediated by or through cell surface proteins expressed on T lymphocytes, such as signaling mediated through PD-1, so as to render a dysfunctional T cell less dysfunctional (e.g., enhancing effector responses to antigen recognition). In some embodiments, a PD-L1 binding antagonist is an anti-PD-1 antibody. In still another specific embodiment, an anti-PD-L1 antibody is MPDL3280A (atezolizumab). In a specific embodiment, an anti-PD-L1 antibody is YW243.55.S70. In another specific embodiment, an anti-PD-L1 antibody is MDX-1105. In another specific embodiment, an anti PD-L1 antibody is MSB0015718C. In still another specific embodiment, an anti-PD-L1 antibody is MED14736.

The term "PD-L2 binding antagonist" refers to a molecule that decreases, blocks, inhibits, abrogates or interferes with signal transduction resulting from the interaction of PD-L2 with either one or more of its binding partners, such as PD-1. In some embodiments, a PD-L2 binding antagonist is a molecule that inhibits the binding of PD-L2 to one or more of its binding partners. In a specific embodiment, the PD-L2 binding antagonist inhibits binding of PD-L2 to PD-1. In some embodiments, the PD-L2 antagonists include anti-PD-L2 antibodies, antigen binding fragments thereof, immunoadhesins, fusion proteins, oligopeptides and other molecules that decrease, block, inhibit, abrogate or interfere with signal transduction resulting from the interaction of PD-L2 with either one or more of its binding partners, such as PD-1. In one embodiment, a PD-L2 binding antagonist reduces the negative co-stimulatory signal mediated by or through cell surface proteins expressed on T lymphocytes, such as signaling mediated through PD-L2, so as render a dysfunctional T cell less dysfunctional (e.g., enhancing effector responses to antigen recognition). In some embodiments, a PD-L2 binding antagonist is an immunoadhesin.

The term "protein," as used herein, refers to any native protein from any vertebrate source, including mammals such as primates (e.g. humans) and rodents (e.g., mice and rats), unless otherwise indicated. The term encompasses "full-length," unprocessed protein as well as any form of the protein that results from processing in the cell. The term also encompasses naturally occurring variants of the protein, e.g., splice variants or allelic variants. Proteins according to the invention include, for example, any protein listed in Table 1.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

$$100 \text{ times the fraction } X/Y$$

where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or to slow the progression of a disease.

As used herein, "delaying progression" of a disorder or disease means to defer, hinder, slow, retard, stabilize, and/or postpone development of the disease or disorder (e.g., a cell proliferative disorder, e.g., cancer). This delay can be of varying lengths of time, depending on the history of the disease and/or individual being treated. As is evident to one skilled in the art, a sufficient or significant delay can, in effect, encompass prevention, in that the individual does not develop the disease. For example, a late stage cancer, such as development of metastasis, may be delayed.

By "reduce" or "inhibit" is meant the ability to cause an overall decrease, for example, of 20% or greater, of 50% or greater, or of 75%, 85%, 90%, 95%, or greater. In certain embodiments, reduce or inhibit can refer to the effector function of an antibody that is mediated by the antibody Fc region, such effector functions specifically including complement-dependent cytotoxicity (CDC), antibody-dependent cellular cytotoxicity (ADCC), and antibody-dependent cellular phagocytosis (ADCP).

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt et al. *Kuby Immunology*, 6$^{th}$ed., W.H. Freeman and Co., page 91 (2007).) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., *J. Immunol.* 150:880-887 (1993); Clarkson et al., *Nature* 352:624-628 (1991).

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

As used herein, "administering" is meant a method of giving a dosage of a compound (e.g., an anti-CD3 antibody of the invention or a nucleic acid encoding an anti-CD3 antibody of the invention) or a composition (e.g., a pharmaceutical composition, e.g., a pharmaceutical composition including an anti-CD3 antibody of the invention) to a subject. The compositions utilized in the methods described herein can be administered, for example, intramuscularly, intravenously, intradermally, percutaneously, intraarterially, intraperitoneally, intralesionally, intracranially, intraarticularly, intraprostatically, intrapleurally, intratracheally, intranasally, intravitreally, intravaginally, intrarectally, topically, intratumorally, peritoneally, subcutaneously, subconjunctivally, intravesicularily, mucosally, intrapericardially, intraumbilically, intraocularly, orally, topically, locally, by inhalation, by injection, by infusion, by continuous infusion, by localized perfusion bathing target cells directly, by catheter, by lavage, in cremes, or in lipid compositions. The method of administration can vary depending on various factors (e.g., the compound or composition being administered and the severity of the condition, disease, or disorder being treated).

II. Compositions and Methods

In one aspect, the invention is based, in part, on anti-CD3 antibodies. In certain embodiments, the anti-CD3 antibodies are multispecific (e.g., bispecific) and bind, in addition to CD3 or a fragment thereof, a second biological molecule (e.g., a cell surface antigen, e.g., a tumor antigen). Antibodies of the invention are useful, for example, for treating or delaying the progression of a cell proliferative disorder (e.g., cancer) or an autoimmune disorder, or for enhancing immune function in a subject having such a disorder.

A. Affinity Improved Anti-CD3 Antibodies

In one aspect, the invention provides isolated antibodies that bind to CD3 (e.g., CD3ε and/or CD3γ). In some instances the anti-CD3 antibody binds to a human CD3 polypeptide or a cynomolgus monkey (cyno) CD3 polypeptide. In some instances, the human CD3 polypeptide or the cyno CD3 polypeptide is a human CD3ε polypeptide (SEQ ID NO: 73) or a cyno CD3ε polypeptide (SEQ ID NO: 74), respectively. In some instances, the human CD3 polypeptide or the cyno CD3 polypeptide is a human CD3γ polypeptide (SEQ ID NO: 75) or a cyno CD3γ polypeptide (SEQ ID NO: 76), respectively. In some instances, the anti-CD3 antibody binds to an epitope within a fragment of CD3 (e.g., human CD3ε) consisting of amino acids 1-26 (SEQ ID NO: 77) or 1-27 (SEQ ID NO: 78) of human CD3ε.

In some instances, the CD3 binding domain binds to an epitope consisting of amino acids of human CD3ε selected from Gln1, Asp2, Asn4, Glu6, and Met7. In one particular embodiment, the CD3 binding domain binds to an epitope that specifically includes Glu6. In certain other embodiments, the CD3 binding domain is provided that does not bind to an epitope that includes human CD3 amino acid Glu5. In certain other embodiments, the CD3 binding domain is provided that does not bind to an epitope that includes human CD3 amino acids Gly3 and Glu5.

A CD3 epitope may be determined by the CD3 binding domain binding to peptide fragments of the epitope. Alternatively, a CD3 epitope may be determined by alanine scanning mutagenesis. In one embodiment, a reduction in binding of a CD3 binding domain to mutated CD3 by 20%, 30%, 50%, 80% or more indicates the amino acid residue of CD3 mutated in an alanine scanning mutagenesis assay is an epitope residue for that CD3 binding domain. Alternatively, a CD3 epitope may be determined by mass spectrometry. In some embodiments, the epitope is determined by crystallography (e.g., crystallography methods). In some embodiments, the CD3 epitope as determined by crystallography is determined using amino acids Q1-M7 of CD3. In some embodiments, the CD3 epitope as determined by crystallography is determined using amino acids QDGNEEMGGITQTPYK (SEQ ID NO: 79) of CD3.

In some embodiments, the CD3 epitope as determined by crystallography may be performed by combining the anti-CD3 antibody Fab, dissolved in 0.15 M NaCl, 25 mM tris, pH 7.5 at 10 mg/ml, with a 2-fold molar excess (1 mg) of CD3ε peptide and initially screening a sparse matrix of precipitants in a sitting drop vapor diffusion format. Optimized crystals may be grown from a1:1 mixture with reservoir solution containing 70% v/v methyl-pentanediol, and 0.1 M HEPES buffer at pH 7.5. The reservoir may be used as a cryoprotectant. The crystals may be transferred to cryogenic temperature by sudden immersion into liquid nitrogen.

The diffraction data for crystals may be collected at Advanced Photon Source beam line 221D, using a MAR300 CCD detector. The recorded diffractions may be integrated and scaled using the program HKL2000.

The structure may be phased by molecular replacement (MR) method using program Phaser. For example, the MR search model is a Fab subunit derived from a crystal structure of HGFA/Fab complex (PDB code: 2R0L). The CD3ε peptide is built into the structure based on a Fo-Fc map. The structure may be subsequently refined with programs REFMAC5 and PHENIX using the maximum likelihood target functions, anisotropic individual B-factor refinement method, and TLS refinement method, to achieve convergence.

In some instances, the invention provides an anti-CD3 antibody having a binding domain comprising at least an HVR-L3 sequence of TQSFILRT (SEQ ID NO: 6) and one, two, three, four, or five HVRs selected from (a) HVR-H1 comprising the amino acid sequence of SEQ ID NO: 1; (b) HVR-H2 comprising the amino acid sequence of SEQ ID NO: 2; (c) HVR-H3 comprising the amino acid sequence of SEQ ID NO: 3; (d) HVR-L1 comprising the amino acid sequence of SEQ ID NO: 4; and (e) HVR-L2 comprising the amino acid sequence of SEQ ID NO: 5.

In some instances, the invention provides an anti-CD3 antibody having a binding domain comprising at least one, two, three, four, five, or six HVRs selected from (a) HVR-H1 comprising the amino acid sequence of SEQ ID NO: 1; (b) HVR-H2 comprising the amino acid sequence of SEQ ID NO: 2; (c) HVR-H3 comprising the amino acid sequence of SEQ ID NO: 3; (d) HVR-L1 comprising the amino acid sequence of SEQ ID NO: 4; (e) HVR-L2 comprising the amino acid sequence of SEQ ID NO: 5; and (f) HVR-L3 comprising the amino acid sequence of SEQ ID NO: 6. In some instances, the anti-CD3 antibody may have a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 7 and/or a VL domain comprising an amino acid sequence having at least 90% sequence identity (e.g., at least 91%, 92, 93%, 94%, 95%, 96%, 97%, 98%, or 99% sequence identity) to, or the sequence of, SEQ ID NO: 8. In a particular instance, the anti-CD3 antibody can be 38E4v11, or a derivative or clonal relative thereof.

In some instances, an anti-CD3 antibody may comprise at least one (e.g., 1, 2, 3, or 4) of heavy chain framework regions FR-H1, FR-H2, FR-H3, and FR-H4 comprising the sequences of SEQ ID NOs: 9-12, respectively, and/or at least one (e.g., 1, 2, 3, or 4) of the light chain framework regions FR-L1, FR-L2, FR-L3, and FR-L4 comprising the sequences of SEQ ID NOs: 13-16, respectively.

In any of the above embodiments, an anti-CD3 antibody is humanized. In one embodiment, an anti-CD3 antibody comprises HVRs as in any of the above embodiments, and further comprises an acceptor human framework, e.g., a human immunoglobulin framework or a human consensus framework.

In another aspect, an anti-CD3 antibody is provided, wherein the antibody comprises a VH as in any of the embodiments provided above, and a VL as in any of the embodiments provided above, wherein one or both of the variable domain sequences include post-translational modifications.

In a further aspect, the invention provides an antibody that binds to the same epitope as an anti-CD3 antibody provided herein. For example, in certain embodiments, an antibody is provided that binds to the same epitope as an anti-CD3 antibody comprising a VH sequence of SEQ ID NO: 7 and a VL sequence of SEQ ID NO: 8. In certain embodiments, an antibody is provided that binds to an epitope within a fragment of CD3 (e.g., human CD3ε) consisting of amino acids 1-26 (SEQ ID NO: 77) or 1-27 (SEQ ID NO: 78) of human CD3ε.

In a further aspect of the invention, an anti-CD3 antibody according to any of the above embodiments is a monoclonal antibody. In other embodiments, the anti-CD3 antibody is a chimeric or human antibody. In one embodiment, an anti-CD3 antibody is an antibody fragment, for example, a Fv, Fab, Fab', scFv, diabody, or F(ab')$_2$ fragment. In another embodiment, the antibody is a full-length antibody, e.g., an intact IgG antibody (e.g., an intact IgG1 antibody) or other antibody class or isotype as defined herein.

In a further aspect, an anti-CD3 antibody according to any of the above embodiments may incorporate any of the features, singly or in combination, as described in Sections 1-8 below.

1. Antibody Affinity

In certain embodiments, an antibody provided herein has a dissociation constant (Kd) of $\leq 1$ μM, $\leq 100$ nM, $\leq 10$ nM, $\leq 1$ nM, $\leq 0.1$ nM, $\leq 0.01$ nM, or $\leq 0.001$ nM (e.g., $10^{-8}$M or less, e.g., from $10^{-8}$M to $10^{-13}$M, e.g., from $10^{-9}$M to $10^{-13}$M).

In one embodiment, Kd is measured by a radiolabeled antigen binding assay (RIA). In one embodiment, an RIA is performed with the Fab version of an antibody of interest and its antigen. For example, solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen et al., *J. Mol. Biol.* 293:865-881 (1999)). To establish conditions for the assay, MICROTITER® multi-well plates (Thermo Scientific) are coated overnight with 5 μg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 pM or 26 pM [$^{125}$I]-antigen are mixed with serial dilutions of a Fab of interest (e.g., consistent with assessment of the anti-VEGF antibody, Fab-12, in Presta et al., *Cancer Res.* 57:4593-4599 (1997)). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN-20®) in PBS. When the plates have dried, 150 μl/well of scintillant (MICROSCINT-20™; Packard) is added, and the plates are counted on a TOPCOUNT™ gamma counter (Packard) for ten minutes. Concentrations of each Fab that give less than or equal to 20% of maximal binding are chosen for use in competitive binding assays.

According to another embodiment, Kd is measured using a BIACORE® surface plasmon resonance assay. For example, an assay using a BIACORE®-2000 or a BIACORE®000 (BIACORE®, Inc., Piscataway, N.J.) is performed at 25° C. with immobilized antigen CM5 chips at ~10 response units (RU). In one embodiment, carboxymethylated dextran biosensor chips (CM5, BIACORE®, Inc.) are activated with N-ethyl-N' (3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 µg/ml (~0.2 µM) before injection at a flow rate of 5 µl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20™) surfactant (PBST) at 25° C. at a flow rate of approximately 25 µl/min. Association rates ($k_{on}$, or $k_a$) and dissociation rates ($k_{off}$, or $k_d$) are calculated using a simple one-to-one Langmuir binding model (BIACORE® Evaluation Software version 3.2) by simultaneously fitting the association and dissociation sensorgrams. The equilibrium dissociation constant ($K_D$) is calculated as the ratio $k_{off}/k_{on}$. See, for example, Chen et al., *J. Mol. Biol.* 293:865-881 (1999). If the on-rate exceeds $10^6 M^{-1}s^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophometer (Aviv Instruments) or a 8000-series SLM-AMINCO™ spectrophotometer (ThermoSpectronic) with a stirred cuvette.

2. Antibody Fragments

In certain embodiments, an antibody provided herein is an antibody fragment. Antibody fragments include, but are not limited to, Fab, Fab', Fab'-SH, F(ab')$_2$, Fv, and scFv fragments, and other fragments described below. For a review of certain antibody fragments, see Hudson et al. *Nat. Med.* 9:129-134 (2003). For a review of scFv fragments, see, e.g., Pluckthun, in *The Pharmacology of Monoclonal Andbodies*, vol. 113, Rosenburg and Moore eds., (Springer-Verlag, New York), pp. 269-315 (1994); see also WO 93/16185; and U.S. Pat. Nos. 5,571,894 and 5,587,458. For discussion of Fab and F(ab')$_2$ fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP 404,097; WO 1993/01161; Hudson et al. *Nat. Med.* 9:129-134 (2003); and Hollinger et al. *Proc. Natl. Acad. Sci. USA* 90: 6444-6448 (1993). Triabodies and tetrabodies are also described in Hudson et al. *Nat. Med.* 9:129-134 (2003).

Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, Mass.; see, e.g., U.S. Pat. No. 6,248,516B1).

Antibody fragments can be made by various techniques, including but not limited to proteolytic digestion of an intact antibody as well as production by recombinant host cells (e.g. *E. coli* or phage), as described herein.

3. Chimeric and Humanized Antibodies

In certain embodiments, an antibody provided herein is a chimeric antibody. Certain chimeric antibodies are described, e.g., in U.S. Pat. No. 4,816,567; and Morrison et al. *Proc. Natl. Acad. Sci. USA*, 81:6851-6855 (1984)). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs (or portions thereof), for example, are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro and Fransson, *Front. Biosci.* 13:1619-1633 (2008), and are further described, e.g., in Riechmann et al., *Nature* 332:323-329 (1988); Queen et al., *Proc. Nat'l Acad. Sci. USA* 86:10029-10033 (1989); U.S. Pat. Nos. 5,821,337, 7,527,791, 6,982,321, and 7,087,409; Kashmiri et al., *Methods* 36:25-34 (2005) (describing specificity determining region (SDR) grafting); Padlan, *Mol. Immunol.* 28:489-498 (1991) (describing "resurfacing"); Dall'Acqua et al., *Methods* 36:43-60 (2005) (describing "FR shuffling"); and Osbourn et al., *Methods* 36:61-68 (2005) and Klimka et al., *Br. J. Cancer*, 83252-260 (2000) (describing the "guided selection" approach to FR shuffling).

Human framework regions that may be used for humanization include but are not limited to: framework regions selected using the "best-fit" method (see, e.g., Sims et al. *J. Immunol.* 151:2296 (1993)); framework regions derived from the consensus sequence of human antibodies of a particular subgroup of light or heavy chain variable regions (see, e.g., Carter et al. *Proc. Natl. Acad. Sci. USA*, 89:4285 (1992); and Presta et al. *J. Immunol.*, 151:2623 (1993)); human mature (somatically mutated) framework regions or human germline framework regions (see, e.g., Almagro and Fransson, *Front. Biosci.* 13:1619-1633 (2008)); and framework regions derived from screening FR libraries (see, e.g., Baca et al., *J. Biol. Chem.* 272:10678-10684 (1997) and Rosok et al., *J. Biol. Chem.* 271:22611-22618 (1996)).

4. Human Antibodies

In certain embodiments, an antibody provided herein is a human antibody. Human antibodies can be produced using various techniques known in the art. Human antibodies are described generally in van Dijk and van de Winkel, *Curr. Opin. Pharmacol.* 5:368-74 (2001) and Lonberg, *Curr. Opin. Immunol.* 20:450-459 (2008).

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, *Nat. Biotech.* 23:1117-1125 (2005). See also, e.g., U.S. Pat. Nos. 6,075,181 and 6,150,584 describing XENO-MOUSE™ technology; U.S. Pat. No. 5,770,429 describing HUMAB® technology; U.S. Pat. No. 7,041,870 describing K-M MOUSE® technology, and U.S. Patent Application Publication No. US 2007/0061900, describing VELOCI-MOUSE® technology). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor *J. Immunol.,* 133: 3001 (1984); Brodeur et al., *Monoclonal Antibody Production Techniques and Applications,* pp. 51-63 (Marcel Dekker, Inc., New York, 1987); and Boerner et al., *J. Immunol.,* 147: 86 (1991).) Human antibodies generated via human B-cell hybridoma technology are also described in Li et al., *Proc. Natl. Acad. Sci. USA,* 103:3557-3562 (2006). Additional methods include those described, for example, in U.S. Pat. No. 7,189,826 (describing production of monoclonal human IgM antibodies from hybridoma cell lines) and Ni, Xiandai Mianyixue, 26(4):265-268 (2006) (describing human-human hybridomas). Human hybridoma technology (Trioma technology) is also described in Vollmers and Brandlein, *Histology and Histopathology,* 20(3):927-937 (2005) and Vollmers and Brandlein, *Methods and Findings in Experimental and Clinical Pharmacology,* 27(3):185-91 (2005).

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

5. Library-Derived Antibodies

Antibodies of the invention may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom et al. in *Methods in Molecular Biology* 178: 1-37 (O'Brien et al., ed., Human Press, Totowa, N.J., 2001) and further described, e.g., in the McCafferty et al., *Nature* 348:552-554; Clackson et al., *Nature* 352: 624-628 (1991); Marks et al., *J. Mol. Biol.* 222: 581-597 (1992); Marks and Bradbury, in *Methods in Molecular Biology* 248:161-175 (Lo, ed., Human Press, Totowa, N.J., 2003); Sidhu et al., *J. Mol. Biol.* 338(2): 299-310 (2004); Lee et al., *J. Mol. Biol.* 340(5):1073-1093 (2004); Fellouse, *Proc. Natl. Acad. Sci. USA* 101(34): 12467-12472 (2004); and Lee et al., *J. Immunol. Methods* 284(1-2): 119-132 (2004).

In certain phage display methods, repertoires of VH and VL genes are separately cloned by polymerase chain reaction (PCR) and recombined randomly in phage libraries, which can then be screened for antigen-binding phage as described in Winter et al., *Ann. Rev. Immunol.,* 12:433-455 (1994). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self antigens without any immunization as described by Griffiths et al., *EMBO J,* 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, *J. Mol. Biol.,* 227: 381-388 (1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

Antibodies or antibody fragments isolated from human antibody libraries are considered human antibodies or human antibody fragments herein.

6. Multispecific Antibodies

In any one of the above aspects, the anti-CD3 antibody provided herein is a multispecific antibody, for example, a bispecific antibody. Multispecific antibodies are antibodies (e.g., monoclonal antibodies) that have binding specificities for at least two different sites. In certain embodiments, bispecific antibodies may bind to two different epitopes of CD3 (e.g., CD3ε or CD3γ). In certain embodiments, one of the binding specificities is for CD3 (e.g., CD3ε or CD3γ) and the other is for any other antigen (e.g., a second biological molecule, e.g., a cell surface antigen, e.g., a tumor antigen). Accordingly, a bispecific anti-CD3 antibody may have binding specificities for CD3 and a second biological molecule, such as a second biological molecule (e.g., a tumor antigen) listed in Table 1 and described herein and in U.S. Pub. No. 2010/0111856.

TABLE 1

Tumor antigen targets of the bispecific anti-CD3 antibodies of the invention

| | | | | | | |
|---|---|---|---|---|---|---|
| Ly6G6D | CD79a | ETBR | IL13Ralpha2 | M-CSF | P2X5 | SSX-2 |
| 0772P | CD79b | ETV6-AML1 fusion protein | IL20Rα | MCSP | p53 | SSX-4 |
| adipophilin | Cdc27 | EZH2 | Intestinal carboxyl esterase | mdm-2 | PAP | STEAP1 |
| AIM-2 | CDK4 | FcRH1 | IRTA2 | MDP | PAX5 | STEAP1 |
| ALDH1A1 | CDKN2A | FcRH2 | Kallikrein 4 | ME1 | PBF | STEAP2 |
| alpha-actinin-4 | CEA | FcRH5 | KIF20A | Melan-A/MART-1 | PMEL17 | survivin |
| alpha-foetoprotein | CLL1 | FLT3-ITD | KK-LC-1 | Meloe | pml-RARalpha fusion protein | SYT-SSX1 or -SSX2 fusion protein |

TABLE 1-continued

Tumor antigen targets of the bispecific anti-CD3 antibodies of the invention

| | | | | | | |
|---|---|---|---|---|---|---|
| Amphiregulin | CLPP | FN1 | KM-HN-1 | MMP-2 | PRAME | TAG-1 |
| ARTC1 | COA-1 | G250/MN/CAIX | K-ras | MMP-7 | PRDX5 | TAG-2 |
| ASLG659 | CPSF | GAGE-1,2,8 | LAGE-1 | MPF | PSCA | Telomerase |
| ASPHD1 | CRIPTO | GAGE-3,4,5,6,7 | LDLR-fucosyltransferase ASfusion protein | MRP4 | PSCA hIg | TENB2 |
| B7-H4 | Cw6 | GDNF-Ra1 | Lengsin | MSG783 | PSMA | TGF-betaRII |
| BAFF-R | CXCR5 | GEDA | LGR5 | MUC1 | PTPRK | TMEFF1 |
| BAGE-1 | CXORF61 | GFRA1 | LY64 | MUC5AC | RAB38/NY-MEL-1 | TMEM118 |
| BCLX (L) | cyclin D1 | glypican-3 | Ly6E | mucin | RAGE-1 | TMEM46 |
| BCR-ABL fusion protein (b3a2) | Cyclin-A1 | GnTVf | CD20 | MUM-1f | RBAF600 | TRAG-3 |
| beta-catenin | dek-can fusion protein | gp100/Pmel17 | LY6K | MUM-2 | RET | Triosephosphate isomerase |
| BING-4 | DKK1 | GPC3 | LYPD1 | MUM-3 | RGS5 | TRP-1/gp75 |
| B-RAF | DR1 | GPNMB | MAGE-A1 | Myosin class I | RhoC | TRP-2 |
| Brevican | DR13 | GPR172A | MAGE-A10 | NA88-A | RNF43 | TRP2-INT2 |
| CALCA | E16 | GPR19 | MAGE-A12 | Napi2b | RNF43 | TrpM4 |
| CASP-5 | EDAR | GPR54 | MAGE-A2 | NCA | RU2AS | Tyrosinase |
| CASP-8 | EFTUD2 | HAVCR1 | MAGE-A3 | neo-PAP | SAGE | tyrosinase |
| CD19 | Elongation factor 2 | HER2 | MAGE-A4 | NFYC | secernin 1 | VEGF |
| CD21 | ENAH (hMena) | HER-2/neu | MAGE-A6 | N-ras | Sema 5b | WT1 |
| CD22 | EpCAM | HERV-K-MEL | MAGE-A9 | NY-BR-1 | SIRT2 | XAGE-1b/GAGED2a |
| CD33 | EphA3 | HLA-DOB | MAGE-C1 | NY-ESO-1/LAGE-2 | SLC35D3 | EGFR-T790M; |
| CD45 | EphB2R | hsp70-2 | MAGE-C2 | OA1 | SNRPD1 | BMPR1B |
| CD70 | Epiregulin | IDO1 | mammaglobin-A | OGT | SOX10 | |
| CD72 | EGFR | IGF2B3 | MART2 | OS-9 | Sp17 | |
| EGFR-G719A | EGFR-G719C; | EGFR-G719S; | EGFR-L858R | EGFR-S768I | EGFR-L861Q | |

The bispecific anti-CD3 antibody (e.g., any one of the anti-CD3 antibodies described above) may have binding specificities for CD3 and a second biological molecule, such as a human leukocyte antigen (HLA)-peptide complex presented on the cell surface by MHC. The bispecific anti-CD3 antibody (e.g., any one of the anti-CD3 antibodies described above) may have binding specificities for CD3 and a second biological molecule, such as the peptide of the HLA-peptide complex, which may be selected from the group consisting of Ly6G6D (lymphocyte antigen 6 complex, locus G6D; Ly6-D, MEGT; NP_067079.2); 0772P (CA125, MUC16; GENBANK® accession no. AF36148); adipophilin (perilipin-2, Adipose differentiation-related protein, ADRP, ADFP, MGC10598; NCBI Reference Sequence: NP_001113.2); AIM-2 (Absent In Melanoma 2, PYHIN4, Interferon-inducible Protein AIM2; NCBI Reference Sequence: NP_004824.1); ALDH1A1 (Aldehyde Dehydrogenase 1Family, Member A1, ALDH1, PUMB1, Retinaldehyde Dehydrogenase 1, ALDC, ALDH-E1, ALHDII, RALDH 1, EC 1.2.1.36, ALDH11, HEL-9, HEL-S-53e, HEL2, RALDH1, Acetaldehyde Dehydrogenase 1, Aldehyde Dehydrogenase 1, Soluble, Adehyde Dehydrogenase, Liver Cytosolic, ALDH Class 1, Epididymis Luminal Protein 12, Epididymis Luminal Protein 9, Epididymis Secretory Sperm Binding Protein Li 53e, Retinal Dehydrogenase 1, RalDH1, Aldehyde Dehydrogenase Family 1 Member A1, Aldehyde Dehydrogenase, Cytosolic, EC 1.2.1; NCBI Reference Sequence: NP_000680.2); alpha-actinin-4 (ACTN4, Actinin, Alpha 4, FSGS1, Focal Segmental Glomerulosclerosis 1, Non-Muscle Alpha-Actinin 4, F-Actin Cross-Linking Protein, FSGS, ACTININ-4, Actinin Alpha4 Isoform, alpha-actinin-4; NCBI Reference Sequence: NP_004915.2); alpha-fetoprotein (AFP, HPAFP, FETA, alpha-1-fetoprotein, alpha-fetoglobulin, Alpha-1-fetoprotein, Alpha-fetoglobulin, HP; GENBANK®: AAB58754.1); Amphiregulin (AREG, SDGF, Schwannoma-Derived Growth Factor, Colorectum Cell-Derived Growth Factor, AR, CRDGF; GENBANK®: AAA51781.1); ARTC1 (ART1, ADP-Ribosytransferase 1, Mono(ADP-Ribosyl)Transferase 1, ADP-Ribosytransferase C2 And C3 Toxin-Like 1, ART2, CD296, RT6, ADP-Ribosytransferase 2, GPI-Linked NAD(P)(+)-Arginine ADP-Ribosytransferase 1, EC 2.4.2.31, CD296 Antigen; NP); ASLG659; ASPHD1 (Aspartate Beta-Hydroxylase Domain Containing 1, Aspartate Beta-Hydroxylase Domain-Containing Protein 1, EC 1.14.11.-, EC 1.14.11; GENBANK®: AAI44153.1); B7-H4 (VTCN1, V-Set Domain Containing T Cell Activation Inhibitor 1, B7H4, B7 Superfamily Member 1, Immune Costimulatory Protein B7-H4, B7h.5, T-Cell Costimulatory Molecule B7x, B7S1, B7X, VCTN1, H4, B7 Family Member, PRO1291, B7 Family Member, H4, T Cell Costimulatory Molecule B7x, V-Set Domain-Containing T-Cell Activation Inhibitor 1, Protein B7S1; GENBANK®: AAZ17406.1); BAFF-R (TNFRSF13C, Tumor Necrosis Factor Receptor Superfamily, Member 13C, BAFFR, B-Cell-Activating Factor Receptor, BAFF Receptor, BLyS Receptor 3, CVID4, BROMIX, CD268, B Cell-Activating Factor Receptor, prolixin, Tumor Necrosis Factor Receptor Superfamily Member 13C, BR3, CD268 Antigen; NCBI Reference Sequence: NP_443177.1); BAGE-1; BCLX (L); BCR-ABL fusion protein (b3a2); beta-catenin (CTNNB1, Catenin (Cadherin-Associated Protein), Beta 1, 88 kDa, CTNNB, MRD19, Catenin (Cadherin-Associated Protein), Beta 1 (88kD), armadillo, Catenin Beta-1; GENBANK®: CAA61107.1); BING-4 (WDR46, WD Repeat Domain 46, C6orf11, BING4, WD Repeat-Containing Protein BING4, Chromosome 6 Open Reading Frame 11, FP221, UTP7, WD Repeat-Containing Protein 46; NP); BMPR1B (bone morphogenetic protein receptor-type IB, GENBANK® accession no. NM_00120; NP); B-RAF (Brevican (BCAN, BEHAB, GENBANK® accession no. AF22905); Brevican (BCAN, Chondroitin Sulfate Proteoglycan 7, Brain-Enriched Hyaluronan-Binding Protein, BEHAB, CSPG7, Brevican Proteoglycan, Brevican Core Protein, Chondroitin Sulfate Proteoglycan BEHAB; GENBANK®: AAH27971.1); CALCA (Calcitonin-Related Polypeptide Alpha, CALC1, Calcitonin 1, calcitonin, Alpha-Type CGRP, Calcitonin Gene-Related Peptide I, CGRP-I, CGRP, CGRP1, CT, KC, Calcitonin/Calcitonin-Related Polypeptide, Alpha, katacalcin; NP); CASP-5 (CASP5, Caspase 5, Apoptosis-Related Cysteine Peptidase, Caspase 5, Apoptosis-Related Cysteine Protease, Protease ICH-3, Protease TY, ICE(rel)-III, ICE (rel)III, ICEREL-Ill, ICH-3, caspase-5, TY Protease, EC 3.4.22.58, ICH3, EC 3.4.22; NP); CASP-8; CD19 (CD19-B-lymphocyte antigen CD19 isoform 2 precursor, B4, CVID3 [*Homo sapiens*], NCBI Reference Sequence: NP_001761.3); CD20 (CD20-B-lymphocyte antigen CD20, membrane-spanning 4-domains, subfamily A, member 1, B1, Bp35, CD20, CVID5, LEU-16, MS4A2, S7; NCBI Reference Sequence: NP_690605.1); CD21 (CD21 (CR2 (Complement receptor or C3DR (C3d/Epstein Barr virus receptor) or Hs.73792 GENBANK® accession no. M2600); (CD22 (B-cell receptor CD22-B isoform, BL-CAM, Lyb-8, Lyb8, SIGLEC-2, FLJ22814, GENBANK® accession No. AK02646); CD22; CD33 (CD33 Molecule, CD33 Antigen (Gp67), Sialic Acid Binding Ig-Like Lectin 3, Sialic Acid-Binding Ig-Like Lectin 3, SIGLEC3, gp67, SIGLEC-3, Myeloid Cell Surface Antigen CD33, p67, Siglec-3, CD33 Antigen; GENBANK®: AAH28152.1); CD45; CD70 (CD70-tumor necrosis factor (ligand) superfamily, member 7; surface antigen CD70; Ki-24 antigen; CD27 ligand; CD27-L; tumor necrosis factor ligand superfamily member 7; NCBI Reference Sequence for species *Homo sapiens*: NP_001243.1); CD72 (CD72 (B-cell differentiation antigen CD72, Lyb-; 359 aa, pI: 8.66, MW: 40225, TM: 1 [P] Gene Chromosome: 9p13.3, GENBANK® accession No. NP_001773.); CD79a (CD79a (CD79A, CD79a, immunoglobulin-associated alpha, a B cell-specific protein that covalently interacts with Ig beta (CD79B) and forms a complex on the surface with Ig M molecules, transduces a signal involved in B-cell differentiation), pI: 4.84, MW: 25028 TM: 2 [P] Gene Chromosome: 19q13.2, GENBANK® accession No. NP_001774.1); CD79b (CD79b (CD79B, CD79b, IGb (immunoglobulin-associated beta), B29, GENBANK® accession no. NM_000626 or 1103867); Cdc27 (Cell Division Cycle 27, D0S1430E, D17S978E, Anaphase Promoting Complex Subunit 3, Anaphase-Promoting Complex Subunit 3, ANAPC3, APC3, CDC127Hs, H-NUC, CDC27 Homolog, Cell Division Cycle 27 Homolog (*S. cerevisiae*), HNUC, NUC2, Anaphase-Promoting Complex, Protein 3, Cell Division Cycle 27 Homolog, Cell Division Cycle Protein 27 Homolog, Nuc2 Homolog; GENBANK®: AAH11656.1); CDK4 (Cyclin-Dependent Kinase 4, Cell Division Protein Kinase 4, PSK-J3, EC 2.7.11.22, CMM3, EC 2.7.11; NCBI Reference Sequence: NP_000066.1); CDKN2A (Cyclin-Dependent Kinase Inhibitor 2A, MLM, CDKN2, MTS1, Cyclin-Dependent Kinase Inhibitor 2A (Melanoma, P16, Inhibits CDK4), Cyclin-Dependent Kinase 4 Inhibitor A, Multiple Tumor Suppressor 1, CDK41, MTS-1, CMM2, P16, ARF, INK4, INK4A, P14, P14ARF, P16-INK4A, P161NK4, P161NK4A, P19, P19ARF, TP16, CDK4 Inhibitor P16-INK4, Cell Cycle Negative Regulator Beta, p14ARF, p16-INK4, p16-INK4a, p161NK4A, p19ARF; NP); CEA; CLL1 (CLL-1 (CLEC12A, MICL, and DCAL, encodes a member of the C-type lectin/C-type lectin-like domain (CTL/CTLD) superfamily. Members of this family share a common protein fold and have diverse functions, such as cell adhesion, cell-cell signaling, glycoprotein turnover, and roles in inflammation and immune response. The protein encoded by this gene is a negative regulator of granulocyte and monocyte function. Several alternatively spliced transcript variants of this gene have been described, but the full-length nature of some of these variants has not been determined. This gene is closely linked to other CTL/CTLD superfamily members in the natural killer gene complex region on chromosome 12p13 (Drickamer K *Curr. Opin. Struct. Biol.* 9):585-90; van Rhenen A, et al., *Blood* 110):2659-66; Chen C H, et al. *Blood* 107):1459-67; Marshall A S, et al. *Eur. J. Immunol.* 36): 2159-69; Bakker A B, et al *Cancer Res.* 64:8443-; Marshall A S, et al *J. Biol. Chem.* 279:14792-80. CLL-1 has been shown to be a type II transmembrane receptor comprising a single C-type lectin-like domain (which is not predicted to bind either calcium or sugar), a stalk region, a transmembrane domain and a short cytoplasmic tail containing an ITIM motif.); CLPP (Caseinolytic Mitochondrial Matrix Peptidase Proteolytic Subunit, Endopeptidase Clp, EC 3.4.21.92, PRLTS3, ATP-Dependent Protease ClpAP (*E. Coli*), ClpP (Caseinolytic Protease, ATP-Dependent, Proteolytic Subunit, *E. Coli*) Homolog, ClpP Caseinolytic Peptidase, ATP-Dependent, Proteolytic Subunit Homolog (*E. Coli*), ClpP Caseinolytic Protease, ATP-Dependent, Proteolytic Subunit Homolog (*E. Coli*), human, Proteolytic Subunit, ATP-Dependent Protease ClpAP, Proteolytic Subunit, Human, ClpP Caseinolytic Peptidase ATP-Dependent, Proteolytic Subunit, ClpP Caseinolytic Peptidase, ATP-Dependent, Proteolytic Subunit Homolog, ClpP Caseinolytic Protease, ATP-Dependent, Proteolytic Subunit Homolog, Putative ATP-Dependent Clp Protease Proteolytic Subunit, Mitochondrial; NP); COA-1; CPSF; CRIPTO (CRIPTO (CR, CR1, CRGF, CRIPTO, TDGF1, teratocarcinoma-derived growth factor, GENBANK® accession no. NP_003203 or NM_00321); Cw6; CXCR5 CXCR5 (Burkitt's lymphoma receptor 1, a G protein-coupled receptor that is activated by the CXCL13 chemokine, functions in lymphocyte migration and humoral defense, plays a role in HIV-2 infection and perhaps development of AIDS, lymphoma, myeloma, and leukemia); 372 aa, pI: 8.54 MW: 41959 TM: 7 [P] Gene Chromosome: 11q23.3, GENBANK® accession No. NP_001707.); CXORF61 CXORF61-chromosome X open reading frame 61[*Homo sapiens*], NCBI Reference Sequence: NP_001017978.1); cyclin D1 (CCND1, BCL1, PRAD1, D11S287E, B-Cell CLL/Lymphoma 1, B-Cell Lymphoma 1 Protein, BCL-1 Oncogene, PRAD1 Oncogene, Cyclin D1 (PRAD1: Parathyroid Adenomatosis 1), G1/S-Specific Cyclin D1, Parathyroid Adenomatosis 1, U21B31, G1/S-Specific Cyclin-D1, BCL-1; NCBI Reference Sequence: NP_444284.1);

Cyclin-A1 (CCNA1, CT146, Cyclin A1; GENBANK®: AAH36346.1); dek-can fusion protein; DKK1 (Dickkopf WNT Signaling Pathway Inhibitor 1, SK, hDkk-1, Dickkopf (*Xenopus Laevis*) Homolog 1, Dickkopf 1 Homolog (*Xenopus Laevis*), DKK-1, Dickkopf 1 Homolog, Dickkopf Related Protein-1, Dickkopf-1 Like, Dickkopf-Like Protein 1, Dickkopf-Related Protein 1, Dickkopf-1, Dkk-1; GENBANK®: AAQ89364.1); DR1 (Down-Regulator Of Transcription 1, TBP-Binding (Negative Cofactor 2), Negative Cofactor 2-Beta, TATA-Binding Protein-Associated Phosphoprotein, NC2, NC2-BETA, Protein Dr1, NC2-beta, Down-Regulator Of Transcription 1; NCBI Reference Sequence: NP_001929.1); DR13 (Major Histocompatibility Complex, Class 11, DR Beta 1, HLA-DR1B, DRw10, DW2.21DR2.2, SS1, DRB1, HLA-DRB, HLA Class II Histocompatibility Antigen, DR-1 Beta Chain, Human Leucocyte Antigen DRB1, Lymphocyte Antigen DRB1, MHC Class II Antigen, MHC Class II HLA-DR Beta 1 Chain, MHC Class II HLA-DR-Beta Cell Surface Glycoprotein, MHC Class II HLA-DRw10-Beta, DR-1, DR-12, DR-13, DR-14, DR-16, DR-4, DR-5, DR-7, DR-8, DR-9, DR1, DR12, DR13, DR14, DR16, DR4, DR5, DR7, DR8, DR9, DRw11, DRw8, HLA-DRB2, Clone P2-Beta-3, MHC Class II Antigen DRB1*1, MHC Class II Antigen DRB1*10, MHC Class II Antigen DRB1*11, MHC Class II Antigen DRB1*12, MHC Class II Antigen DRB1*13, MHC Class II Antigen DRB1*14, MHC Class II Antigen DRB1*15, MHC Class II Antigen DRB1*16, MHC Class II Antigen DRB1*3, MHC Class II Antigen DRB1*4, MHC Class II Antigen DRB1*7, MHC Class II Antigen DRB1*8, MHC Class II Antigen DRB1*9; NP); E16 (E16 (LAT1, SLC7A5, GENBANK® accession no. NM_00348); EDAR (EDAR—tumor necrosis factor receptor superfamily member EDAR precursor, EDA-A1 receptor; downless homolog; ectodysplasin-A receptor; ectodermal dysplasia receptor; anhidrotic ectodysplasin receptor 1, DL; ECTD10A; ECTD10B; ED1R; ED3; ED5; EDA-A1R; EDA1R; EDA3; HRM1 [*Homo sapiens*]; NCBI Reference Sequence: NP_071731.1); EFTUD2 (Elongation Factor Tu GTP Binding Domain Containing 2, Elongation Factor Tu GTP-Binding Domain-Containing Protein 2, hSNU114, SNU114 Homolog, U5 SnRNP-Specific Protein, 116 KDa, MFDGA, KIAA0031, 116 KD, U5 SnRNP Specific Protein, 116 KDa U5 Small Nuclear Ribonucleoprotein Component, MFDM, SNRNP116, Snrp116, Snu114, U5-116KD, SNRP116, U5-116 KDa; GENBANK®: AAH02360.1); EGFR (Epidermal Growth Factor Receptor, ERBB, Proto-Oncogene C-ErbB-1, Receptor Tyrosine-Protein Kinase ErbB-1, ERBB1, HER1, EC 2.7.10.1, Epidermal Growth Factor Receptor (Avian Erythroblastic Leukemia Viral (V-Erb-B) Oncogene Homolog), Erythroblastic Leukemia Viral (V-Erb-B) Oncogene Homolog (Avian), PIG61, Avian Erythroblastic Leukemia Viral (V-Erb-B) Oncogene Homolog, Cell Growth Inhibiting Protein 40, Cell Proliferation-Inducing Protein 61, mENA, EC 2.7.10; GENBANK®: AAH94761.1); EGFR-G719A; EGFR-G719C; EGFR-G719S; EGFR-L858R; EGFR-L861Q; EGFR-S7681; EGFR-T790M; Elongation factor 2 (EEF2, Eukaryotic Translation Elongation Factor 2, EF2, Polypeptidyl-TRNA Translocase, EF-2, SCA26, EEF-2; NCBI Reference Sequence: NP_001952.1); ENAH (hMena) (Enabled Homolog (*Drosophila*), MENA, Mammalian Enabled, ENA, NDPP1, Protein Enabled Homolog; GENBANK®: AAH95481.1)—results for just "ENAH" not "ENAH (hMena)"; EpCAM (Epithelial Cell Adhesion Molecule, M4S1, MIC18, Tumor-Associated Calcium Signal Transducer 1, TACSTD1, TROP1, Adenocarcinoma-Associated Antigen, Cell Surface Glycoprotein Trop-1, Epithelial Glycoprotein 314, Major Gastrointestinal Tumor-Associated Protein GA733-2, EGP314, KSA, DIAR5, HNPCC8, Antigen Identified By Monoclonal Antibody AUA1, EGP-2, EGP40, ESA, KS1/4, MK-1, Human Epithelial Glycoprotein-2, Membrane Component, Chromosome 4, Surface Marker (35kD Glycoprotein), EGP, Ep-CAM, GA733-2, M1S2, CD326 Antigen, Epithelial Cell Surface Antigen, hEGP314, KS 1/4 Antigen, ACSTD1; GENBANK®: AAH14785.1); EphA3 (EPH Receptor A3, ETK1, ETK, TYRO4, HEK, Eph-Like Tyrosine Kinase 1, Tyrosine-Protein Kinase Receptor ETK1, EK4, EPH-Like Kinase 4, EC 2.7.10.1, EPHA3, HEK4, Ephrin Type-A Receptor 3, Human Embryo Kinase 1, TYRO4 Protein Tyrosine Kinase, hEK4, Human Embryo Kinase, Tyrosine-Protein Kinase TYRO4, EC 2.7.10; GENBANK®: AAH63282.1); EphB2R; Epiregulin (EREG, ER, proepiregulin; GENBANK®: AAI36405.1); ETBR (EDNRB, Endothelin Receptor Type B, HSCR2, HSCR, Endothelin Receptor Non-Selective Type, ET-B, ET-BR, ETRB, ABCDS, WS4A, ETB, Endothelin B Receptor; NP); ETV6-AML1 fusion protein; EZH2 (Enhancer Of Zeste Homolog 2 (*Drosophila*), Lysine N-Methytransferase 6, ENX-1, KMT6 EC 2.1.1.43, EZH1, WVS, Enhancer Of Zeste (*Drosophila*) Homolog 2, ENX1, EZH2b, KMT6A, WVS2, Histone-Lysine N-Methyltransferase EZH2, Enhancer Of Zeste Homolog 2, EC 2.1.1; GENBANK®: AAH10858.1); FcRH1 (FCRL1, Fc Receptor-Like 1, FCRH1, Fc Receptor Homolog 1, FcR-Like Protein 1, Immune Receptor Translocation-Associated Protein 5, IFGP1, IRTA5, hIFGP1, IFGP Family Protein 1, CD307a, Fc Receptor-Like Protein 1, Immunoglobulin Superfamily Fc Receptor, Gp42, FcRL1, CD307a Antigen; GENBANK®: AAH33690.1); FcRH2 (FCRL2, Fc Receptor-Like 2, SPAP1, SH2 Domain-Containing Phosphatase Anchor Protein 1, Fc Receptor Homolog 2, FcR-Like Protein 2, Immunoglobulin Receptor Translocation-Associated Protein 4, FCRH2, IFGP4, IRTA4, IFGP Family Protein 4, SPAP1A, SPAP1B, SPAP1C, CD307b, Fc Receptor-Like Protein 2, Immune Receptor Translocation-Associated Protein 4, Immunoglobulin Superfamily Fc Receptor, Gp42, SH2 Domain Containing Phosphatase Anchor Protein 1, FcRL2, CD307b Antigen; GENBANK®: AAQ88497.1); FcRH5 (FCRL5, Fc Receptor-Like 5, IRTA2, Fc Receptor Homolog 5, FcR-Like Protein 5, Immune Receptor Translocation-Associated Protein 2, BXMAS1, FCRH5, CD307, CD307e, PRO820, Fc Receptor-Like Protein 5, Immunoglobulin Superfamily Receptor Translocation Associated 2 (IRTA2), FcRL5, CD307e Antigen; GENBANK®: AAI01070.1); FLT3-ITD; FN1 (Fibronectin 1, Cold-Insoluble Globulin, FN, Migration-Stimulating Factor, CIG, FNZ, GFND2, LETS, ED-B, FINC, GFND, MSF, fibronectin; GENBANK®: AAI43764.1); G250 MN, CAIX, Carbonic Anhydrase IX, Carbonic Dehydratase, RCC-Associated Protein G250, Carbonate Dehydratase IX, Membrane Antigen MN, Renal Cell Carcinoma-Associated Antigen G250, CA-IX, P54/58N, pMW1, RCC-Associated Antigen G250, Carbonic Anhydrase 9; NP);—alias results for "G250" not "G250/MN/CAIX"; GAGE-1,2,8; GAGE-3,4,5,6,7; GDNF-Ra1 (GDNF family receptor alpha 1; GFRA1; GDNFR; GDNFRA; RETL1; TRNR1; RET1L; GDNFR-alpha1; GFR-ALPHA-; U95847; BC014962; NM_145793 NM_005264); GEDA (GENBANK® accession No. AY26076); GFRA1-GDNF family receptor alpha-1; GDNF receptor alpha-1; GDNFR-alpha-1; GFR-alpha-1; RET ligand 1; TGF-beta-related neurotrophic factor receptor 1 [*Homo sapiens*]; ProtKB/Swiss-Prot: P56159.2; glypican-3 (GPC3, Glypican 3, SDYS, Glypican Proteoglycan 3, Intestinal Protein OCI-5, GTR2-2, MXR7, SGBS1, DGSX, OCI-5. SGB, SGBS, Heparan Sulphate Proteoglycan, Secreted Glypican-3, OC15; GENBANK®: AAH35972.1); GnTVf; gp100 (PMEL, Premelanosome Protein, SILV, D12S53E, PMEL17, SIL, Melanocyte Protein Pmel 17, Melanocytes Lineage-Specific Antigen GP100, Melanoma-Associated ME20 Antigen, Silver Locus Protein Homolog, ME20-M, ME20M, P1, P100, Silver (Mouse Homolog) Like, Silver Homolog (Mouse), ME20, SI, Melanocyte Protein Mel 17, Melanocyte Protein PMEL, Melanosomal Matrix Protein7, Silver, Mouse, Homolog Of; GENBANK®: AAC60634.1); GPC; GPNMB (Glycoprotein (Transmembrane) Nmb, Glycoprotein NMB, Glycoprotein Nmb-Like Protein, osteoactivin, Transmembrane Glycoprotein HGFIN, HGFIN, NMB, Transmembrane Glycoprotein, Transmembrane Glycoprotein NMB; GENBANK®: AAH32783.1); GPR172A (G protein-coupled receptor 172A; GPCR41; FLJ11856; D15Ertd747e); NP_078807.1; NM_024531.3); GPR19 (G protein-coupled receptor 19; Mm.478; NP_006134.1; NM_006143.2); GPR54 (KISS1 receptor; KISS1R; GPR54; HOT7T175; AXOR1; NP_115940.2; NM_032551.4); HAVCR1 (Hepatitis A Virus Cellular Receptor 1, T-Cell Immunoglobulin Mucin Family Member 1, Kidney Injury Molecule 1, KIM-1, KIM1, TIM, TIM-1, TIM1, TIMD-1, TIMD1, T-Cell Immunoglobulin Mucin Receptor 1, T-Cell Membrane Protein 1, HAVCR, HAVCR-1, T Cell Immunoglobin Domain And Mucin Domain Protein 1, HAVcr-1, T-Cell Immunoglobulin And Mucin Domain-Containing Protein 1; GENBANK®: AAH13325.1); HER2 (ERBB2, V-Erb-B2 Avian Erythroblastic Leukemia Viral Oncogene Homolog 2, NGL, NEU, Neuro/Glioblastoma Derived Oncogene Homolog, Metastatic Lymph Node Gene 19 Protein, Proto-Oncogene C-ErbB-2, Proto-Oncogene Neu, Tyrosine Kinase-Type Cell Surface Receptor HER2, MLN 19, p185erbB2, EC 2.7.10.1, V-Erb-B2 Avian Erythroblastic Leukemia Viral Oncogene Homolog 2 (Neuro/Glioblastoma Derived Oncogene Homolog), CD340, HER-2, HER-2/neu, TKR1, C-Erb B2/Neu Protein, herstatin, Neuroblastoma/Glioblastoma Derived Oncogene Homolog, Receptor Tyrosine-Protein Kinase ErbB-2, V-Erb-B2 Erythroblastic Leukemia Viral Oncogene Homolog 2, Neuro/Glioblastoma Derived Oncogene Homolog, MLN19, CD340 Antigen, EC 2.7.10; NP); HER-2/neu—alias of above; HERV-K-MEL; HLA-DOB (Beta subunit of MHC class II molecule (Ia antigen) that binds peptides and presents them to CD4+ T lymphocytes); 273 aa, pI: 6.56, MW: 30820.TM: 1 [P] Gene Chromosome: 6p21.3, GENBANK® accession No. NP_002111); hsp70-2 (HSPA2, Heat Shock 70 kDa Protein 2, Heat Shock 70kD Protein 2, HSP70-3, Heat Shock-Related 70 KDa Protein 2, Heat Shock 70 KDa Protein 2; GENBANK®: AAD21815.1); IDO1 (Indoleamine 2,3-Dioxygenase 1, IDO, INDO, Indoleamine-Pyrrole 2,3-Dioxygenase, IDO-1, Indoleamine-Pyrrole 2,3 Dioxygenase, Indolamine 2,3 Dioxygenase, Indole 2,3 Dioxygenase, EC 1.13.11.52; NCBI Reference Sequence: NP_002155.1); IGF2B3; IL13Ralpha2 (IL13RA2, Interleukin 13 Receptor, Alpha 2, Cancer/Testis Antigen 19, Interleukin-13-Binding Protein, IL-13R-alpha-2, IL-13RA2, IL-13 Receptor Subunit Alpha-2, IL-13R Subunit Alpha-2, CD213A2, CT19, IL-13R, IL13BP, Interleukin 13 Binding Protein, Interleukin 13 Receptor Alpha 2 Chain, Interleukin-13 Receptor Subunit Alpha-2, IL13R, CD213a2 Antigen; NP); IL20Rα; Intestinal carboxyl esterase; IRTA2 (alias of FcRH5); Kallikrein 4 (KLK4, Kallikrein-Related Peptidase 4, PRSS17, EMSP1, Enamel Matrix Serine Proteinase 1, Kallikrein-Like Protein 1, Serine Protease 17, KLK-L1, PSTS, A12A1, Kallikrein 4 (Prostase, Enamel Matrix, Prostate), ARM1, EMSP, Androgen-Regulated Message 1, Enamel Matrix Serine Protease 1, kallikrein, kallikrein-4, prostase, EC 3.4.21.-, Prostase, EC 3.4.21; GENBANK®: AAX30051.1); KIF20A (Kinesin Family Member 20A, RAB6KIFL, RAB6 Interacting, Kinesin-Like (Rabkinesin6), Mitotic a; LAGE-1; LDLR-fucosyttransferaseASfusion protein; Lengsin (LGSN, Lengsin, Lens Protein With Glutamine Synthetase Domain, GLULD1, Glutamate-Ammonia Ligase Domain-Containing Protein 1, LGS, Glutamate-Ammonia Ligase (Glutamine Synthetase) Domain Containing 1, Glutamate-Ammonia Ligase (Glutamine Synthase) Domain Containing 1, Lens Glutamine Synthase-Like; GENBANK®: AAF61255.1); LGR5 (leucine-rich repeat-containing G protein-coupled receptor 5; GPR49, GPR6; NP_003658.1; NM_003667.2; LY64 (Lymphocyte antigen 64 (RP10, type I membrane protein of the leucine rich repeat (LRR) family, regulates B-cell activation and apoptosis, loss of function is associated with increased disease activity in patients with systemic lupus erythematosis); 661 aa, pI: 6.20, MW: 74147 TM: 1 [P] Gene Chromosome: 5q12, GENBANK® accession No. NP_005573.; Ly6E (lymphocyte antigen 6 complex, locus E; Ly67, RIG-E, SCA-2, TSA-; NP_002337.1; NM_002346.2); LY6K (lymphocyte antigen 6 complex, locus K; LY6K; HSJ001348; FLJ3522; NP_059997.3; NM_017527.3); LyPD1-LY6/PLAUR domain containing 1, PHTS [Homo sapiens], GENBANK®: AAH17318.1); MAGE-A1 (Melanoma Antigen Family A, 1 (Directs Expression Of Antigen MZ2-E, MAGE1, Melanoma Antigen Family A 1, MAGEA1, Melanoma Antigen MAGE-1, Melanoma-Associated Antigen 1, Melanoma-Associated Antigen MZ2-E, Antigen MZ2-E, Cancer/Testis Antigen 1.1, CT1.1, MAGE-1 Antigen, Cancer/Testis Antigen Family 1, Member 1, Cancer/Testis Antigen Family 1, Member 1, MAGE1A; NCBI Reference Sequence: NP_004979.3); MAGE-A10 (MAGEA10, Melanoma Antigen Family A, 10, MAGE10, MAGE-10 Antigen, Melanoma-Associated Antigen 10, Cancer/Testis Antigen 1.10, CT1.10, Cancer/Testis Antigen Family 1, Member 10, Cancer/Testis Antigen Family 1, Member 10; NCBI Reference Sequence: NP_001238757.1); MAGE-A12 (MAGEA12, Melanoma Antigen Family A, 12, MAGE12, Cancer/Testis Antigen 1.12, CT1.12, MAGE12F Antigen, Cancer/Testis Antigen Family 1, Member 12, Cancer/Testis Antigen Family 1, Member 12, Melanoma-Associated Antigen 12, MAGE-12 Antigen; NCBI Reference Sequence: NP_001159859.1); MAGE-A2 (MAGEA2, Melanoma Antigen Family A, 2, MAGE2, Cancer/Testis Antigen 1.2, CT1.2, MAGEA2A, MAGE-2 Antigen, Cancer/Testis Antigen Family 1, Member 2, Cancer/Testis Antigen Family 1, Member 2, Melanoma Antigen 2, Melanoma-Associated Antigen 2; NCBI Reference Sequence: NP_001269434.1); MAGE-A3 (MAGEA3, Melanoma Antigen Family A, 3, MAGE3, MAGE-3 Antigen, Antigen MZ2-D, Melanoma-Associated Antigen 3, Cancer/Testis Antigen 1.3, CT1.3, Cancer/Testis Antigen Family 1, Member 3, HIP8, HYPD, MAGEA6, Cancer/Testis Antigen Family 1, Member 3; NCBI Reference Sequence: NP_005353.1); MAGE-A4 (MAGEA4, Melanoma Antigen Family A, 4, MAGE4, Melanoma-Associated Antigen 4, Cancer/Testis Antigen 1.4, CT1.4, MAGE-4 Antigen, MAGE-41 Antigen, MAGE-X2 Antigen, MAGE4A, MAGE4B, Cancer/Testis Antigen Family 1, Member 4, MAGE-41, MAGE-X2, Cancer/Testis Antigen Family 1, Member 4; NCBI Reference Sequence: NP_001011550.1); MAGE-A6 (MAGEA6, Melanoma Antigen Family A, 6, MAGE-6 Antigen, Melanoma-Associated Antigen 6, Cancer/Testis Antigen 1.6, CT1.6, MAGE3B Antigen, Cancer/Testis Antigen Family 1, Melanoma Antigen Family A 6, Member 6, MAGE-3b, MAGE3B, Cancer/Testis Antigen Family 1, Member 6; NCBI Reference Sequence: NP_787064.1); MAGE-A9 (MAGEA9, Melanoma Antigen Family A, 9, MAGE9, MAGE-9 Antigen, Melanoma-Associated Antigen 9, Cancer/Testis Antigen 1.9, CT1.9, Cancer/Testis Antigen Family 1, Member 9, Cancer/Testis Antigen Family 1, Member 9, MAGEA9A; NCBI Reference Sequence: NP_005356.1); MAGE-C1 (MAGEC1, Melanoma Antigen Family C, 1, Cancer/Testis Antigen 7.1, CT7.1, MAGE-C1 Antigen, Cancer/Testis Antigen Family 7, Member 1, CT7, Cancer/Testis Antigen Family 7, Member 1, Melanoma-Associated Antigen C1; NCBI Reference Sequence: NP_005453.2); MAGE-C2 (MAGEC2, Melanoma Antigen Family C, 2, MAGEE1, Cancer/Testis Antigen 10, CT10, HCA587, Melanoma Antigen, Family E, 1, Cancer/Testis Specific, Hepatocellular Carcinoma-Associated Antigen 587, MAGE-C2 Antigen, MAGE-E1 Antigen, Hepatocellular Cancer Antigen 587, Melanoma-Associated Antigen C2; NCBI Reference Sequence: NP_057333.1); mammaglobin-A (SCGB2A2, Secretoglobin, Family 2A, Member 2, MGB1, Mammaglobin 1, UGB2, Mammaglobin A, mammaglobin-A, Mammaglobin-1, Secretoglobin Family 2A Member 2; NP); MART2 (HHAT, Hedgehog Acyltransferase, SKI1, Melanoma Antigen Recognized By T-Cells 2, Skinny Hedgehog Protein 1, Skn, Melanoma Antigen Recognized By T Cells 2, Protein-Cysteine N-Palmitoyltransferase HHAT, EC 2.3.1.-; GENBANK®: AAH39071.1); M-CSF (CSF1, Colony Stimulating Factor 1 (Macrophage), MCSF, CSF-1, lanimostim, Macrophage Colony-Stimulating Factor 1, Lanimostim; GENBANK®: AAH21117.1); MCSP (SMCP, Sperm Mitochondria-Associated Cysteine-Rich Protein, MCS, Mitochondrial Capsule Selenoprotein, HSMCSGEN1, Sperm Mitochondrial-Associated Cysteine-Rich Protein; NCBI Reference Sequence: NP_109588.2); XAGE-1b/GAGED2a; WT1 (Wilms Tumor 1, WAGR, GUD, WIT-2, WT33, Amino-Terminal Domain Of EWS, NPHS4, Last Three Zinc Fingers Of The DNA-Binding Domain Of WT1, AWT1, Wilms Tumor Protein, EWS-WT1; GENBANK®: AAB33443.1); VEGF; Tyrosinase (TYR; OCAIA; OCA1A; tyrosinase; SHEP; NP_000363.1; NM_000372.4; GENBANK®: AAB60319.1); TrpM4 (BR22450, FLJ20041, TRPM4, TRPM4B, transient receptor potential cation channel, subfamily M, member 4, GENBANK® accession no. NM_01763); TRP2-INT2; TRP-2; TRP-1/gp75 (Tyrosinase-Related Protein 1, 5,6-Dihydroxyindole-2-Carboxyic Acid Oxidase, CAS2, CATB, TYRP, OCA3, Catalase B, b-PROTEIN, Glycoprotein 75, EC 1.14.18., Melanoma Antigen Gp75, TYRP1, TRP, TYRRP, TRP1, SHEP11, DHICA Oxidase, EC 1.14.18, GP75, EC 1.14.18.1; Triosephosphate isomerase (Triosephosphate isomerase 1, TPID, Triose-Phosphate Isomerase, HEL-S-49, TIM, Epididymis Secretory Protein Li 49, TPI, Triosephosphate Isomerase, EC 5.3.1.1; TRAG-3 (CSAG Family Member 2, Cancer/Testis Antigen Family 24, CSAG3B, Member 2, CSAG Family Member 3B, Cancer/Testis Antigen Family 24 Member 2, Cancer/Testis Antigen 24.2, Chondrosarcoma-Associated Gene 2/3 Protein, Taxol-Resistant-Associated Gene 3 Protein, Chondrosarcoma-Associated Gene 2/3 Protein-Like, CT24.2, Taxol Resistance Associated Gene 3, TRAG-3, CSAG3A, TRAG3); TMEM46 (shisa homolog 2 (Xenopus laevis); SHISA; NP_001007539.1; NM_001007538.1; TMEM118 (ring finger protein, transmembrane 2; RNFT2; FLJ1462; NP_001103373.1; NM_001109903.1; TMEFF1 (transmembrane protein with EGF-like and two follistatin-like domains 1; Tomoregulin-; H7365; C9orf2; C9ORF2; U19878; X83961; NM_080655; NM_003692; TGF-betaRil (TGFBR2, Transforming Growth Factor, Beta Receptor II (70/80 kDa), TGFbeta-RII, MFS2, tbetaR-II, TGFR-2, TGF-Beta Receptor Type IIB, TGF-Beta Type II Receptor, TGF-Beta Receptor Type-2, EC 2.7.11.30, Transforming Growth Factor Beta Receptor Type IIC, AAT3, TbetaR-II, Transforming Growth Factor, Beta Receptor II (70-80kD), TGF-Beta Receptor Type II, FAA3, Transforming Growth Factor-Beta Receptor Type II, LDS1B, HNPCC6, LDS2B, LDS2, RIIC, EC 2.7.11, TAAD2; TENB2 (TMEFF2, tomoregulin, TPEF, HPP1, TR, putative transmembrane proteoglycan, related to the EGF/heregulin family of growth factors and follistatin); 374 aa, NCBI Accession: AAD55776, AAF91397, AAG49451, NCBI RefSeq: NP_057276; NCBI Gene: 23671; OMIM: 605734; SwissProt Q9UIK5; GENBANK® accession No. AF179274; AY358907, CAF85723, CQ782436; TAG-2; TAG-1 (Contactin 2 (Axonal), TAG-1, AXT, Axonin-1 Cell Adhesion Molecule, TAX, Contactin 2 (transiently Expressed), TAX1, Contactin-2, Axonal Glycoprotein TAG-1, Transiently-Expressed Axonal Glycoprotein, Transient Axonal Glycoprotein, Axonin-1, TAX-1, TAG1, FAME5; PRF: 444868); SYT-SSX1 or -SSX2 fusion protein; survivin; STEAP2 (HGNC_8639, IPCA-1, PCANAP, STAMP, STEAP2, STMP, prostate cancer associated gene 1, prostate cancer associated protein 1, six transmembrane epithelial antigen of prostate 2, six transmembrane prostate protein, GENBANK® accession no. AF45513; STEAP1 (six transmembrane epithelial antigen of prostate, GENBANK® accession no. NM_01244; SSX-4; SSX-2 (SSX2, Synovial Sarcoma, X Breakpoint2, X Breakpoint 2, SSX, X Breakpoint 2B, Cancer/Testis Antigen 5.2, X-Chromosome-Related 2, Tumor Antigen HOM-MEL-40, CT5.2, HD21, Cancer/Testis Antigen Family 5, HOM-MEL-40, Isoform B, Cancer/Testis Antigen Family 5 member 2a, member 2a, Protein SSX2, Sarcoma, Sarcoma, Synovial, X-Chromosome-Related 2, synovial, Synovial Sarcoma, X Breakpoint 2B, Synovial Sarcomam, SSX2A; Sp17; SOX10 (SRY (Sex Determining Region Y)-Box 10, mouse, PCWH, DOM, WS4, WS2E, WS4C, Dominant Megacolon, mouse, Human Homolog Of, Dominant Megacolon, SRY-Related HMG-Box Gene 10, Human Homolog Of, transcription Factor SOX-10; GENBANK®: CAG30470.1); SNRPD1 (Small Nuclear Ribonucleoprotein D1, Small Nuclear Ribonucleoprotein D1, Polypeptide 16 kDa, Polypeptide (16kD), SNRPD, HsT2456, Sm-D1, SMD1, Sm-D Autoantigen, Small Nuclear Ribonucleoprotein D1 Polypeptide 16 kDa Pseudogene, SnRNP Core Protein D1, Small Nuclear Ribonucleoprotein Sm D1; SLC35D3 (Solute Carrier Family 35, Member D3, FRCL1, Fringe Connection-Like Protein 1, bA55K22.3, Frc, Fringe-Like 1, Solute Carrier Family 35 Member D3; NCBI GENBANK®: NC_000006.11 NC_018917.2 NT_025741.16); SIRT2 (Sirtuin 2, NAD-Dependent Deacetylase Sirtuin-2, SIRL2, Silent Information Regulator 2, Regulatory Protein SIR2 Homolog 2, Sir2-Related Protein Type 2, SIR2-Like Protein 2, Sirtuin Type 2, Sirtuin (Silent Mating Type Information Regulation 2 Homolog) 2 (S. Cerevisiae), Sirtuin-2, Sirtuin (Silent Mating Type Information Regulation 2, S. Cerevisiae, Homolog) 2, EC 3.5.1., SIR2; GENBANK®: AAK51133.1); Sema 5b (FLJ10372, KIAA1445, Mm.42015, SEMA5B, SEMAG, Semaphorin 5b Hlog, sema domain, seven thrombospondin repeats (type 1 and type 1-like), transmembrane domain (TM) and short cytoplasmic domain, (semaphorin) 5B, GENBANK® accession no. AB04087; secernin 1 (SCRN1, SES1, KIAA0193, secerin-1; GENBANK®: EAL24458.1); SAGE (SAGE, Sarcoma Antigen 1, Cancer/Testis Antigen 14, CT14, Putative Tumor Antigen; NCBI Reference Sequence: NP_061136.2); RU2AS (KAAG1, Kidney Associated Antigen 1, RU2AS, RU2 Antisense Gene Protein, Kidney-Associated Antigen 1; GENBANK®: AAF23613.1); RNF43-E3 ubiquitin-protein ligase RNF43 precursor [Homo sapiens], RNF124; URCC; NCBI Reference Sequence: NP_060233.3; RhoC (RGS5 (Regulator Of G-Protein Signaling 5, MSTP032, Regulator Of G-Protein Signalling 5, MSTP092, MST092, MSTP106, MST106, MSTP129, MST129; GENBANK®: AAB84001.1); RET (ret proto-oncogene; MEN2A; HSCR1; MEN2B; MTC1; PTC; CDHF12; Hs.168114; RET51; RET-ELE; NP_066124.1; NM_020975.4); RBAF600 (UBR4, Ubiquitin Protein Ligase E3 Component N-Recognin 4, Zinc Finger, UBR1 Type 1, ZUBR1, E3 Ubiquitin-Protein Ligase UBR4, RBAF600, 600 KDa Retinoblastoma Protein-Associated Factor, Zinc Finger UBR1-Type Protein 1, EC 6.3.2., N-recognin-4, KIAA0462, p600, EC 6.3.2, KIAA1307; GENBANK®: AAL83880.1); RAGE-1 (MOK, MOK Protein Kinase, Renal Tumor Antigen, RAGE, MAPK/MAK/MRK Overlapping Kinase, Renal Tumor Antigen 1, Renal Cell Carcinoma Antigen, RAGE-1, EC 2.7.11.22, RAGE1; UniProtKB/Swiss-Prot: Q9U007.1); RAB38/NY-MEL-1 (RAB38, NY-MEL-1, RAB38, Member RAS Oncogene Family, Melanoma Antigen NY-MEL-1, Rab-Related GTP-Binding Protein, Ras-Related Protein Rab-38, rrGTPbp; GENBANK®: AAH15808.1); PTPRK (DJ480J14.2.1 (Protein Tyrosine Phosphatase, Receptor Type, K R-PTP-KAPPA, Protein Tyrosine Phosphatase Kappa, Protein Tyrosine Phosphatase Kappa), Protein Tyrosine Phosphatase, Receptor Type, K, Protein-Tyrosine Phosphatase Kappa, Protein-Tyrosine Phosphatase, Receptor Type, Kappa, R-PTP-kappa, Receptor-Type Tyrosine-Protein Phosphatase Kappa, EC 3.1.3.48, PTPK; GENBANK®: AAI44514.1); PSMA; PSCA hig(2700050C12Rik, C530008O16Rik, RIKEN cDNA 2700050C12, RIKEN cDNA 2700050C12 gene, GENBANK® accession no. AY358628); PSCA (Prostate stem cell antigen precursor, GENBANK® accession no. AJ29743; PRDX5 (Peroxiredoxin 5, EC 1.11.1.15, TPx Type VI, B166, Antioxidant Enzyme B166, HEL-S-55, Liver Tissue 2D-Page Spot 71B, PMP20, Peroxisomal Antioxidant Enzyme, PRDX6, Thioredoxin Peroxidase PMP20, PRXV, AOEB166, Epididymis Secretory Protein Li 55, Alu Co-Repressor 1, Peroxiredoxin-5, Mitochondrial, Peroxiredoxin V, prx-V, Thioredoxin Reductase, Prx-V, ACR1, Alu Corepressor, PLP; GENBANK®: CAG33484.1); PRAME (Preferentially Expressed Antigen In Melanoma, Preferentially Expressed Antigen Of Melanoma, MAPE, OIP-4, OIPA, CT130, Cancer/Testis Antigen 130, Melanoma Antigen Preferentially Expressed In Tumors, Opa-Interacting Protein 4, Opa-Interacting Protein OIP4; GENBANK®: CAG30435.1); pml-RARalpha fusion protein; PMEL17 (silver homolog; SILV; D12S53E; PMEL17; SI; SIL); ME20; gp10 BC001414; BT007202; M32295; M77348; NM_006928; PBF (ZNF395, Zinc Finger Protein 395, PRF-1, Huntington disease regulatory, HD Gene Regulatory Region-Binding Protein, Region-Binding Protein 2, Protein 2, Papillomavirus Regulatory Factor 1, HD-Regulating Factor 2, Papillomavirus-Regulatory Factor, PRF1, HDBP-2, Si-1-8-14, HDBP2, Huntington'S Disease Gene Regulatory Region-Binding Protein 2, HDRF-2, Papillomavirus Regulatory Factor PRF-1, PBF; GENBANK®: AAH01237.1); PAX5 (Paired Box 5, Paired Box Homeotic Gene 5, BSAP, Paired Box Protein Pax-5, B-Cell Lineage Specific Activator, Paired Domain Gene 5, Paired Box Gene 5 (B-Cell Lineage Specific Activator Protein), B-Cell-Specific Transcription Factor, Paired Box Gene 5 (B-Cell Lineage Specific Activator); PAP (REG3A, Regenerating Islet-Derived 3 Alpha, INGAP, PAP-H, Hepatointestinal Pancreatic Protein, PBBCGF, Human Proislet Peptide, REG-Ill, Pancreatitis-Associated Protein 1, Reg3, Reg III-Alpha, hepatocarcinoma-intestine-pancreas, Regenerating Islet-Derived Protein III-Alpha, Pancreatic Beta Cell Growth Factor, HIP, PAP Homologous Protein, HIP/PAP, Proliferation-Inducing Protein 34, PAP1, Proliferation-Inducing Protein 42, REG-3-alpha, Regenerating Islet-Derived Protein 3-Alpha, Pancreatitis-Associated Protein; GENBANK®: AAH36776.1); p53 (TP53, Tumor Protein P53, TPR53, P53, Cellular Tumor Antigen P53, Antigen NY-CO-13, Mutant Tumor Protein 53, Phosphoprotein P53, P53 Tumor Suppressor, BCC7, Transformation-Related Protein 53, LFS1, tumor Protein 53, Li-Fraumeni Syndrome, Tumor Suppressor P53; P2X5 (Purinergic receptor P2X ligand-gated ion channel 5, an ion channel gated by extracellular ATP, may be involved in synaptic transmission and neurogenesis, deficiency may contribute to the pathophysiology of idiopathic detrusor instability); 422 aa), pI: 7.63, MW: 47206 TM: 1 [P] Gene Chromosome: 17p13.3, GENBANK® accession No. NP_002552; OGT (O-Linked N-Acetylglucosamine (GlcNAc) Transferase, 0-GlcNAc Transferase P110 Subunit, O-Linked N-Acetylglucosamine (GlcNAc) Transferase (UDP-N-Acetylglucosamine:Polypeptide-N-Acetylglucosaminyl Transferase, UDP-N-Acetylglucosamine-Peptide N-Acetylglucosaminyltransferase 110 KDa Subunit, UDP-N-Acetylglucosamine:Polypeptide-N-Acetylglucosaminyl Transferase, Uridinediphospho-N-Acetylglucosamine:Polypeptide Beta-N-Acetylglucosaminyl Transferase, O-GlcNAc Transferase Subunit P110, EC 2.4.1.255, 0-Linked N-Acetylglucosamine Transferase 110 KDa Subunit, EC 2.4.1, HRNT1, EC 2.4.1.186, 0-GLCNAC; GENBANK®: AAH38180.1); OA1 (Osteoarthritis QTL 1, OASD; GENBANK®: CAA88742.1); NY-ESO-1/LAGE-2 (Cancer/Testis Antigen 1B, CTAG1B, NY-ESO-1, LAGE-2, ESO1, CTAG1, CTAG, LAGE2B, Cancer/Testis Antigen 1, Autoimmunogenic Cancer/Testis Antigen NY-ESO-1, Ancer Antigen 3, Cancer/Testis Antigen 6.1, New York Esophageal Squamous Cell Carcinoma 1, L Antigen Family Member 2, LAGE2, CT6.1, LAGE2A; GENBANK®: AAI30365.1); NY-BR-1 (ANKRD30A, Ankyrin Repeat Domain 30A, Breast Cancer Antigen NY-BR-1, Serologically Defined Breast Cancer Antigen NY-BR-1, Ankyrin Repeat Domain-Containing Protein 30A; NCBI Reference Sequence: NP_443723.2); N-ras (NRAS, Neuroblastoma RAS Viral (V-Ras) Oncogene Homolog, NRAS1, Transforming Protein N-Ras, GTPase NRas, ALPS4, N-Ras Protein Part 4, NS6, Oncogene Homolog, HRAS1; GENBANK®: AAH05219.1); NFYC (Nuclear Transcription Factor Y, Gamma, HAP5, HSM, Nuclear Transcription Factor Y Subunit C, Transactivator HSM-1/2, CCAAT Binding Factor Subunit C, NF-YC, CCAAT Transcription Binding Factor Subunit Gamma, CAAT Box DNA-Binding Protein Subunit C, Histone H1 Transcription Factor Large Subunit 2A, CBFC, Nuclear Transcription Factor Y Subunit Gamma, CBF-C, Transactivator HSM-1, H1TF2A, Transcription Factor NF-Y, C Subunit; neo-PAP (PAPOLG, Poly(A) Polymerase Gamma, Neo-Poly(A) Polymerase, Nuclear Poly(A) Polymerase Gamma, Polynucleotide Adenylytransferase Gamma, SRP RNA 3' Adenylating Enzyme/Pap2, PAP-gamma, Neo-PAP, SRP RNA 3'-Adenylating Enzyme, PAP2, EC 2.7.7.19, PAPG; NCBI Reference Sequence: NP_075045.2); NCA (CEACAM6, GENBANK® accession no. M1872); Napi3b (NAPI-3B, NPTIlb, SLC34A2, solute carrier family 34 (sodium phosphate), member 2, type II sodium-dependent phosphate transporter 3b, GENBANK® accession no. NM_00642); Myosin class I; MUM-3;

MUM-2 (TRAPPC1, Trafficking Protein Particle Complex 1, BET5, BET5 Homolog, MUM2, Melanoma Ubiquitous Mutated 2, Multiple Myeloma Protein 2, Trafficking Protein Particle Complex Subunit 1; MUM-1f; Mucin (MUC1, Mucin 1, Cell Surface Associated, PEMT, PUM, CA 15-3, MCKD1, ADMCKD, Medullary Cystic Kidney Disease 1 (Autosomal Dominant), ADMCKD1, Mucin 1, Transmembrane, CD227, Breast Carcinoma-Associated Antigen DF3, MAM6, Cancer Antigen 15-3, MCD, Carcinoma-Associated Mucin, MCKD, Krebs Von Den Lungen-6, MUC-1/SEC, Peanut-Reactive Urinary Mucin, MUC1/ZD, Tumor-Associated Epithelial Membrane Antigen, DF3 Antigen, Tumor-Associated Mucin, episialin, EMA, H23 Antigen, H23AG, Mucin-1, KL-6, Tumor Associated Epithelial Mucin, MUC-1, Episialin, PEM, CD227 Antigen; UniProtKB/Swiss-Prot: P15941.3); MUCSAC (Mucin 5AC, Oligomeric Mucus/Gel-Forming, Tracheobronchial Mucin MUC5, TBM, Mucin 5, Subtypes A And C, Tracheobronchial/Gastric, leB, Gastric Mucin, Mucin 5AC, Oligomeric Mucus/Gel-Forming Pseudogene, Lewis B Blood Group Antigen, LeB, Major Airway Glycoprotein, MUC-5AC, Mucin-5 Subtype AC, Tracheobronchial; MUC1 (Mucin 1, Cell Surface Associated, PEMT, PUM, CA 15-3, MCKD1, ADMCKD, Medullary Cystic Kidney Disease 1 (Autosomal Dominant), ADMCKD1, Mucin 1, Transmembrane, CD227, Breast Carcinoma-Associated Antigen DF3, MAM6, Cancer Antigen 15-3, MCD, Carcinoma-Associated Mucin, MCKD, Krebs Von Den Lungen-6, MUC-1/SEC, Peanut-Reactive Urinary Mucin, MUC-1/X, Polymorphic Epithelial Mucin, MUC1/ZD, Tumor-Associated Epithelial Membrane Antigen, DF3 Antigen, Tumor-Associated Mucin, episialin, EMA, h23 Antigen, H23AG, mucin-1, KL-6, Tumor Associated Epithelial Mucin, MUC-1, Episialin, PEM, CD227 Antigen; MSG783 (RNF124, hypothetical protein FLJ20315, GENBANK® accession no. NM-01776; MRP4-multidrug resistance-associated protein 4 isoform 3, MOAT-B; MOATB [*Homo sapiens*]; NCBI Reference Sequence: NP_001288758.1; MPF (MPF, MSLN, SMR, megakaryocyte potentiating factor, mesothelin, GENBANK® accession no. NM_00582; MMP-7 (MMP7, matrilysin, MPSL1, matrin, Matrix Metalloproteinase 7 (Matrilysin, Uterine), Uterine Matrilysin, Matrix Metalloproteinase-7, EC 3.4.24.23, Pump-1 Protease, Matrin, Uterine Metalloproteinase, PUMP1, MMP-7, EC 3.4.24, PUMP-1; GENBANK®: AAC37543.1); MMP-2 (MMP2, Matrix Metallopeptidase 2 (Gelatinase A, 72 kDa Gelatinase, 72 kDa Type IV Collagenase), MONA, CLG4A, Matrix Metalloproteinase 2 (Gelatinase A, 72kD Gelatinase, 72kD Type IV Collagenase), CLG4, 72 kDa Gelatinase, 72 kDa Type IV Collagenase), Matrix Metalloproteinase-2, MMP-II, 72 KDa Gelatinase, Collagenase Type IV-A, MMP-2, Matrix Metalloproteinase-II, TBE-1, Neutrophil Gelatinase, EC 3.4.24.24, EC 3.4.24; GENBANK®: AAH02576.1); and Meloe.

For example, in some instances, an anti-CD3 antibody having a first binding domain comprising at least an HVR-L3 sequence of TQSFILRT (SEQ ID NO: 6) and one, two, three, four, or five HVRs selected from (a) HVR-H1 comprising the amino acid sequence of SEQ ID NO: 1; (b) HVR-H2 comprising the amino acid sequence of SEQ ID NO: 2; (c) HVR-H3 comprising the amino acid sequence of SEQ ID NO: 3; (d) HVR-L1 comprising the amino acid sequence of SEQ ID NO: 4; and (e) HVR-L2 comprising the amino acid sequence of SEQ ID NO: 5, may have a second binding domain that binds to Ly6G6D. In some instances, the first binding domain that binds CD3 comprises at least one (e.g., 1, 2, 3, or 4) of heavy chain framework regions FR-H1, FR-H2, FR-H3, and FR-H4 comprising the sequences of SEQ ID NOs: 9-12, respectively, and/or at least one (e.g., 1, 2, 3, or 4) of the light chain framework regions FR-L1, FR-L2, FR-L3, and FR-L4 comprising the sequences of SEQ ID NOs: 13-16, respectively. In some instances, the first binding domain that binds to CD3 may, for example, comprise a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 8. In some instances, the first binding domain that binds to CD3 may, for example, comprise (a) a VL domain comprising an amino acid sequence having at least 90% sequence identity (e.g., at least 91%, 92%, 93%, 94%, 95%, 96%, 97%, 98%, or 99/sequence identity) to, or the sequence of, SEQ ID NO: 8 and (b) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 7, such as possessed by the anti-CD3 antibody, 38E4v11, described herein.

In other instances, an anti-CD3 antibody having a first binding domain comprising at least one, two, three, four, five, or six HVRs selected from (a) HVR-H1 comprising the amino acid sequence of SEQ ID NO: 1; (b) HVR-H2 comprising the amino acid sequence of SEQ ID NO: 2; (c) HVR-H3 comprising the amino acid sequence of SEQ ID NO: 3; (d) HVR-L1 comprising the amino acid sequence of SEQ ID NO: 4; (e) HVR-L2 comprising the amino acid sequence of SEQ ID NO: 5; and (f) HVR-L3 comprising the amino acid sequence of SEQ ID NO: 6, such as 38E4v11, may have a second binding domain that binds to a cell surface antigen (e.g., a tumor antigen) on a target cell other than an immune effector cell.

In some instances, the cell surface antigen may be expressed in low copy number on the target cell. For example, in some instances, the cell surface antigen is expressed or present at less than 35,000 copies per target cell. In some embodiments, the low copy number cell surface antigen is present between 100 and 35,000 copies per target cell; between 100 and 30,000 copies per target cell; between 100 and 25,000 copies per target cell; between 100 and 20,000 copies per target cell; between 100 and 15,000 copies per target cell; between 100 and 10,000 copies per target cell; between 100 and 5,000 copies per target cell; between 100 and 2,000 copies per target cell; between 100 and 1,000 copies per target cell; or between 100 and 500 copies per target cell. Copy number of the cell surface antigen can be determined, for example, using a standard Scatchard plot.

In some instances, an anti-CD3 antibody having a first binding domain comprising at least one, two, three, four, five, or six HVRs selected from (a) HVR-H1 comprising the amino acid sequence of SEQ ID NO: 1; (b) HVR-H2 comprising the amino acid sequence of SEQ ID NO: 2; (c) HVR-H3 comprising the amino acid sequence of SEQ ID NO: 3; (d) HVR-L1 comprising the amino acid sequence of SEQ ID NO: 4; (e) HVR-L2 comprising the amino acid sequence of SEQ ID NO: 5; and (f) HVR-L3 comprising the amino acid sequence of SEQ ID NO: 6, such as 38E4v11, may have a second binding domain that binds to Ly6G6D. Ly6G6D may be expressed or present in low copy number on the target cell, for example, at about 20,000 copies per target cell to about 30,000 copies per target cell (e.g., between about 20,000 copies per target cell to about 25,000 copies per target cell, or between about 25,000 copies per target cell to about 30,000 copies per target cell), depending on the target cell. The copy number of Ly6G6D can be determined using a standard Scatchard plot. In some instances, the first binding domain that binds CD3 comprises at least one (e.g., 1, 2, 3, or 4) of heavy chain framework regions FR-H1, FR-H2, FR-H3, and FR-H4 comprising the sequences of SEQ ID NOs: 9-12, respectively, and/or at least one (e.g., 1, 2, 3, or 4) of the light chain framework regions FR-L1, FR-L2, FR-L3, and FR-L4 comprising the sequences of SEQ ID NOs: 13-16, respectively. In some instances, the first binding domain that binds to CD3 may, for example, comprise a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 8. In some instances, the first binding domain that binds to CD3 may, for example, comprise (a) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 8 and (b) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 7, such as possessed by the anti-CD3 antibody, 38E4v11, described herein.

In other instances, an anti-CD3 antibody having a first binding domain comprising at least one, two, three, four, five, or six hypervariable regions (HVRs) selected from (a) HVR-H1 comprising the amino acid sequence of SEQ ID NO: 1; (b) HVR-H2 comprising the amino acid sequence of SEQ ID NO: 2; (c) HVR-H3 comprising the amino acid sequence of SEQ ID NO: 3; (d) HVR-L1 comprising the amino acid sequence of SEQ ID NO: 4; (e) HVR-L2 comprising the amino acid sequence of SEQ ID NO: 5; and (f) HVR-L3 comprising the amino acid sequence of SEQ ID NO: 6, such as 38E4v11, may have a second binding domain that binds to CD20. The second binding domain that binds to CD20 may, for example, comprise at least one, two, three, four, five, or six hypervariable regions (HVRs) selected from (a) HVR-H1 comprising the amino acid sequence of SEQ ID NO: 17; (b) HVR-H2 comprising the amino acid sequence of SEQ ID NO: 18; (c) HVR-H3 comprising the amino acid sequence of SEQ ID NO: 19; (d) HVR-L1 comprising the amino acid sequence of SEQ ID NO: 20; (e) HVR-L2 comprising the amino acid sequence of SEQ ID NO: 21; and (f) HVR-L3 comprising the amino acid sequence of SEQ ID NO: 22, such as possessed by the anti-CD20 antibody, 2H7.v16 (described in U.S. Pat. No. 7,799,900). In some instances, the second binding domain that binds CD20 comprises at least one (e.g., 1, 2, 3, or 4) of heavy chain framework regions FR-H1, FR-H2, FR-H3, and FR-H4 comprising the sequences of SEQ ID NOs: 23-26, respectively, and/or at least one (e.g., 1, 2, 3, or 4) of the light chain framework regions FR-L1, FR-L2, FR-L3, and FR-L4 comprising the sequences of SEQ ID NOs: 27-30, respectively. In some instances, the second binding domain that binds to CD20 may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 31; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 32; or (c) a VH domain as in (a) and a VL domain as in (b), such as possessed by the anti-CD20 antibody, 2H7.v16 (described in U.S. Pat. No. 7,799,900).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 1; (b) HVR-H2 comprising the amino acid sequence of SEQ ID NO: 2; (c) HVR-H3 comprising the amino acid sequence of SEQ ID NO: 3; (d) HVR-L1 comprising the amino acid sequence of SEQ ID NO: 4; (e) HVR-L2 comprising the amino acid sequence of SEQ ID NO: 5; and (f) HVR-L3 comprising the amino acid sequence of SEQ ID NO: 6, such as 38E4v11, may have a second binding domain that binds to FcRH5. The second binding domain that binds to FcRH5 may, for example, comprise at least one, two, three, four, five, or six hypervariable regions (HVRs) selected from (a) HVR-H1 comprising the amino acid sequence of SEQ ID NO: 33; (b) HVR-H2 comprising the amino acid sequence of SEQ ID NO: 34; (c) HVR-H3 comprising the amino acid sequence of SEQ ID NO: 35; (d) HVR-L1 comprising the amino acid sequence of SEQ ID NO: 36; (e) HVR-L2 comprising the amino acid sequence of SEQ ID NO: 37; and (f) HVR-L3 comprising the amino acid sequence of SEQ ID NO: 38, such as possessed by the anti-FcRH5 antibody, 1G7. In some instances, the second binding domain that binds FcRH5 comprises at least one (e.g., 1, 2, 3, or 4) of heavy chain framework regions FR-H1, FR-H2, FR-H3, and FR-H4 comprising the sequences of SEQ ID NOs: 39-42, respectively, and/or at least one (e.g., 1, 2, 3, or 4) of the light chain framework regions FR-1, FR-L2, FR-L3, and FR-L4 comprising the sequences of SEQ ID NOs: 43-46, respectively. In some instances, the second binding domain that binds to FcRH5 may, for example, comprise (a) a VH domain comprising an amino acid sequence having at least 90% sequence identity (e.g., at least 91%, 92, 93%, 94%, 95%, 96%, 97%, 98%, or 99% sequence identity) to, or the sequence of, SEQ ID NO: 47; (b) a VL domain comprising an amino acid sequence having at least 90% sequence identity (e.g., at least 91%, 92, 93%, 94%, 95%, 96%, 97%, 98%, or 99% sequence identity) to, or the sequence of, SEQ ID NO: 48; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 1; (b) HVR-H2 comprising the amino acid sequence of SEQ ID NO: 2; (c) HVR-H3 comprising the amino acid sequence of SEQ ID NO: 3; (d) HVR-L1 comprising the amino acid sequence of SEQ ID NO: 4; (e) HVR-L2 comprising the amino acid sequence of SEQ ID NO: 5; and (f) HVR-L3 comprising the amino acid sequence of SEQ ID NO: 6, such as 38E4v11, may have a second binding domain that binds to PMEL17.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 1; (b) HVR-H2 comprising the amino acid sequence of SEQ ID NO: 2; (c) HVR-H3 comprising the amino acid sequence of SEQ ID NO: 3; (d) HVR-L1 comprising the amino acid sequence of SEQ ID NO: 4; (e) HVR-L2 comprising the amino acid sequence of SEQ ID NO: 5; and (f) HVR-L3 comprising the amino acid sequence of SEQ ID NO: 6, such as 38E4v11, may have a second binding domain that binds to LY6E.

In some instances, an anti-CD3 antibody having a first binding domain comprising at least one, two, three, four, five, or six hypervariable regions (HVRs) selected from (a)

HVR-H1 comprising the amino acid sequence of SEQ ID NO: 1; (b) HVR-H2 comprising the amino acid sequence of SEQ ID NO: 2; (c) HVR-H3 comprising the amino acid sequence of SEQ ID NO: 3; (d) HVR-L1 comprising the amino acid sequence of SEQ ID NO: 4; (e) HVR-L2 comprising the amino acid sequence of SEQ ID NO: 5; and (f) HVR-L3 comprising the amino acid sequence of SEQ ID NO: 6, such as 38E4v11, may have a second binding domain that binds to CD19.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 1; (b) HVR-H2 comprising the amino acid sequence of SEQ ID NO: 2; (c) HVR-H3 comprising the amino acid sequence of SEQ ID NO: 3; (d) HVR-L1 comprising the amino acid sequence of SEQ ID NO: 4; (e) HVR-L2 comprising the amino acid sequence of SEQ ID NO: 5; and (f) HVR-L3 comprising the amino acid sequence of SEQ ID NO: 6, such as 38E4v11, may have a second binding domain that binds to CD33.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 1; (b) HVR-H2 comprising the amino acid sequence of SEQ ID NO: 2; (c) HVR-H3 comprising the amino acid sequence of SEQ ID NO: 3; (d) HVR-L1 comprising the amino acid sequence of SEQ ID NO: 4; (e) HVR-L2 comprising the amino acid sequence of SEQ ID NO: 5; and (f) HVR-L3 comprising the amino acid sequence of SEQ ID NO: 6, such as 38E4v11, may have a second binding domain that binds to CD22.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 1; (b) HVR-H2 comprising the amino acid sequence of SEQ ID NO: 2; (c) HVR-H3 comprising the amino acid sequence of SEQ ID NO: 3; (d) HVR-L1 comprising the amino acid sequence of SEQ ID NO: 4; (e) HVR-L2 comprising the amino acid sequence of SEQ ID NO: 5; and (f) HVR-L3 comprising the amino acid sequence of SEQ ID NO: 6, such as 38E4v11, may have a second binding domain that binds to CD79A.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 1; (b) HVR-H2 comprising the amino acid sequence of SEQ ID NO: 2; (c) HVR-H3 comprising the amino acid sequence of SEQ ID NO: 3; (d) HVR-L1 comprising the amino acid sequence of SEQ ID NO: 4; (e) HVR-L2 comprising the amino acid sequence of SEQ ID NO: 5; and (f) HVR-L3 comprising the amino acid sequence of SEQ ID NO: 6, such as 38E4v11, may have a second binding domain that binds to CD79B.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 1; (b) HVR-H2 comprising the amino acid sequence of SEQ ID NO: 2; (c) HVR-H3 comprising the amino acid sequence of SEQ ID NO: 3; (d) HVR-L1 comprising the amino acid sequence of SEQ ID NO: 4; (e) HVR-L2 comprising the amino acid sequence of SEQ ID NO: 5; and (f) HVR-L3 comprising the amino acid sequence of SEQ ID NO: 6, such as 38E4v11, may have a second binding domain that binds to EDAR.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 1; (b) HVR-H2 comprising the amino acid sequence of SEQ ID NO: 2; (c) HVR-H3 comprising the amino acid sequence of SEQ ID NO: 3; (d) HVR-L1 comprising the amino acid sequence of SEQ ID NO: 4; (e) HVR-L2 comprising the amino acid sequence of SEQ ID NO: 5; and (f) HVR-L3 comprising the amino acid sequence of SEQ ID NO: 6, such as 38E4v11, may have a second binding domain that binds to GFRA1.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 1; (b) HVR-H2 comprising the amino acid sequence of SEQ ID NO: 2; (c) HVR-H3 comprising the amino acid sequence of SEQ ID NO: 3; (d) HVR-L1 comprising the amino acid sequence of SEQ ID NO: 4; (e) HVR-L2 comprising the amino acid sequence of SEQ ID NO: 5; and (f) HVR-L3 comprising the amino acid sequence of SEQ ID NO: 6, such as 38E4v11, may have a second binding domain that binds to MRP4.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 1; (b) HVR-H2 comprising the amino acid sequence of SEQ ID NO: 2; (c) HVR-H3 comprising the amino acid sequence of SEQ ID NO: 3; (d) HVR-L1 comprising the amino acid sequence of SEQ ID NO: 4; (e) HVR-L2 comprising the amino acid sequence of SEQ ID NO: 5; and (f) HVR-L3 comprising the amino acid sequence of SEQ ID NO: 6, such as 38E4v11, may have a second binding domain that binds to RET. The second binding domain that binds to RET may, for example, comprise at least one, two, three, four, five, or six hypervariable regions (HVRs) selected from (a) HVR-H1 comprising the amino acid sequence of SEQ ID NO: 49; (b) HVR-H2 comprising the amino acid sequence of SEQ ID NO: 50; (c) HVR-H3 comprising the amino acid sequence of SEQ ID NO: 51; (d) HVR-L1 comprising the amino acid sequence of SEQ ID NO: 52; (e) HVR-L2 comprising the amino acid sequence of SEQ ID NO: 53; and (f) HVR-L3 comprising the amino acid sequence of SEQ ID NO: 54, such as possessed by the anti-RET antibody, 41205.v6. In some instances, the second binding domain that binds to RET may, for example, comprise (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 55; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 56; or (c) a VH domain as in (a) and a VL domain as in (b).

In some instances, an anti-CD3 antibody having a first binding domain comprising at least one, two, three, four, five, or six hypervariable regions (HVRs) selected from (a) HVR-H1 comprising the amino acid sequence of SEQ ID NO: 1; (b) HVR-H2 comprising the amino acid sequence of SEQ ID NO: 2; (c) HVR-H3 comprising the amino acid sequence of SEQ ID NO: 3; (d) HVR-L1 comprising the amino acid sequence of SEQ ID NO: 4; (e) HVR-L2 comprising the amino acid sequence of SEQ ID NO: 5; and (f) HVR-L3 comprising the amino acid sequence of SEQ ID NO: 6, such as 38E4v11, may have a second binding domain that binds to Steap1.

In some instances, an anti-CD3 antibody having a first binding domain comprising at least one, two, three, four, five, or six hypervariable regions (HVRs) selected from (a) HVR-H1 comprising the amino acid sequence of SEQ ID NO: 1; (b) HVR-H2 comprising the amino acid sequence of SEQ ID NO: 2; (c) HVR-H3 comprising the amino acid sequence of SEQ ID NO: 3; (d) HVR-L1 comprising the amino acid sequence of SEQ ID NO: 4; (e) HVR-L2 comprising the amino acid sequence of SEQ ID NO: 5; and (f) HVR-L3 comprising the amino acid sequence of SEQ ID NO: 6, such as 38E4v11, may have a second binding domain that binds to TenB2.

In some embodiments, bispecific antibodies may also be used to localize cytotoxic agents to cells which express a tumor antigen, such as a tumor antigen listed in Table 1 (e.g., Ly6G6D, CD20, FcRH5, HER2, LYPD1, PMEL17, LY6E, CD19, CD33, CD22, CD79A, CD79B, EDAR, GFRA1, MRP4, RET, Steap1, or TenB2). Bispecific antibodies can also be prepared as full-length antibodies or antibody fragments.

Techniques for making multispecific antibodies include, but are not limited to, recombinant co-expression of two immunoglobulin heavy chain-light chain pairs having different specificities (see Milstein and Cuello, *Nature* 305: 537 (1983)), WO 93/08829, and Traunecker et al., *EMBO J.* 10: 3655 (1991)), and "knob-in-hole" engineering (see, e.g., U.S. Pat. No. 5,731,168). "Knob-in-hole" engineering of multispecific antibodies may be utilized to generate a first arm containing a knob and a second arm containing the hole into which the knob of the first arm may bind. The knob of the multispecific antibodies of the invention may be an anti-CD3 arm in one embodiment. Alternatively, the knob of the multispecific antibodies of the invention may be an anti-target/antigen arm in one embodiment. The hole of the multispecific antibodies of the invention may be an anti-CD3 arm in one embodiment. Alternatively, the hole of the multispecific antibodies of the invention may be an anti-target/antigen arm in one embodiment. Multispecific antibodies may also be engineered using immunoglobulin cross-over (also known as Fab domain exchange or CrossMab format) technology (see eg., WO2009/080253; Schaefer et al., *Proc. Natl. Acad. Sci. USA*, 108:11187-11192 (2011)). Multi-specific antibodies may also be made by engineering electrostatic steering effects for making antibody Fc-heterodimeric molecules (WO 2009/089004A1); cross-linking two or more antibodies or fragments (see, e.g., U.S. Pat. No. 4,676,980, and Brennan et al., *Science*, 229: 81 (1985)); using leucine zippers to produce bi-specific antibodies (see, e.g., Kostelny et al., *J. Immunol.*, 148(5):1547-1553 (1992)); using "diabody" technology for making bispecific antibody fragments (see, e.g., Hollinger et al., *Proc. Natl. Acad. Sci. USA*, 90:6444-6448 (1993)); and using single-chain Fv (sFv) dimers (see, e.g. Gruber et al., *J. Immunol*, 152:5368 (1994)); and preparing trispecific antibodies as described, e.g., in Tutt et al. *J. Immunol.* 147: 60 (1991).

Engineered antibodies with three or more functional antigen binding sites, including "Octopus antibodies," are also included herein (see, e.g. US 2006/0025576A1).

The antibodies, or antibody fragments thereof, may also include a "Dual Acting FAb" or "DAF" comprising an antigen binding site that binds to CD3 as well as another, different antigen (e.g., a second biological molecule) (see, e.g., US 2008/0069820).

7. Antibody Variants

In certain embodiments, amino acid sequence variants of the anti-CD3 antibodies of the invention (e.g., bispecific anti-CD3 antibodies of the invention that bind to CD3, e.g., with high affinity (e.g., 38E4v11), and a second biological molecule, e.g., a cell surface antigen, e.g., a tumor antigen, such as TDB antibodies of the invention or variants thereof) are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, for example, antigen-binding.

a. Substitution, Insertion, and Deletion Variants

In certain embodiments, antibody variants having one or more amino acid substitutions are provided. Sites of interest for substitutional mutagenesis include the HVRs and FRs. Conservative substitutions are shown in Table 2 under the heading of "preferred substitutions." More substantial changes are provided in Table 2 under the heading of "exemplary substitutions," and as further described below in reference to amino acid side chain classes. Amino acid substitutions may be introduced into an antibody of interest and the products screened for a desired activity, for example, retained/improved antigen binding, decreased immunogenicity, or improved ADCC or CDC.

TABLE 2

Exemplary and Preferred Amino Acid Substitutions

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:

(1) hydrophobic: Norleucine, Met, Ala, Val, Leu, Ie;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

One type of substitutional variant involves substituting one or more hypervariable region residues of a parent antibody (e.g. a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g. binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, *Methods Mol. Biol.* 207:179-196 (2008)), and/or residues that contact antigen, with the resulting variant VH or VL being tested for binding affinity. Affinity maturation by constructing and reselecting from secondary libraries has been described, e.g., in Hoogenboom et al. in *Methods in Molecular Biology* 178:1-37 (O'Brien et al., ed., Human Press, Totowa, N.J., (2001).) In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may, for example, be outside of antigen contacting residues in the HVRs. In certain embodiments of the variant VH and VL sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham and Wells (1989) *Science*, 244:1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for ADEPT) or a polypeptide which increases the serum half-life of the antibody.

b. Glycosylation Variants

In certain embodiments, anti-CD3 antibodies of the invention (e.g., bispecific anti-CD3 antibodies of the invention that bind to CD3, preferably with high affinity (e.g., 38E4v11), and a second biological molecule, e.g., a cell surface antigen, e.g., a tumor antigen, such as TDB antibodies of the invention or variants thereof) can be altered to increase or decrease the extent to which the antibody is glycosyated. Addition or deletion of glycosylation sites to anti-CD3 antibody of the invention may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. *TIBTECH* 1526-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

In one embodiment, anti-CD3 antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e. g. complex, hybrid and high mannose structures) as measured by MALDI-TOF mass spectrometry, as described in WO 2008/077546, for example. Asn297 refers to the asparagine residue located at about position 297 in the Fc region (EU numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. *J. Mol. Biol.* 336:1239-1249 (2004); Yamane-Ohnuki et al. *Biotech. Bioeng.* 87: 614 (2004). Examples of cell lines capable of producing defucosylated antibodies include Lec13 CHO cells deficient in protein fucosylation (Ripka et al. *Arch. Biochem. Biophys.* 249:533-545 (1986); US Pat Appl No US 2003/0157108 A1, Presta, L; and WO 2004/056312 A1, Adams et al., especially at Example 11), and knockout cell lines, such as alpha-1,6-fucosyltransferase gene, FUT8, knockout CHO cells (see, e.g., Yamane-Ohnuki et al. *Biotech. Bioeng.* 87: 614 (2004); Kanda, Y. et al., *Biotechnol. Bioeng.*, 94(4):680-688 (2006); and WO2003/085107).

Anti-CD3 antibodies variants are further provided with bisected oligosaccharides, for example, in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878 (Jean-Mairet et al.); U.S. Pat. No. 6,602,684 (Umana et al.); and US 2005/0123546 (Umana et al.). Antibody variants with at least one galactose residue in the oligosaccharide attached to the Fc region are also provided. Such antibody variants may have improved CDC function. Such antibody variants are described, e.g., in WO 1997/30087 (Patel et al.); WO 1998/58964 (Raju, S.); and WO 1999/22764 (Raju, S.).

c. Fc Region Variants

In certain embodiments, one or more amino acid modifications may be introduced into the Fc region of an anti-CD3 antibody of the invention (e.g., a bispecific anti-CD3 antibody of the invention that binds to CD3, preferably with high affinity (e.g., 38E4v11), and a second biological molecule, e.g., a cell surface antigen, e.g., a tumor antigen, such as a TDB antibody of the invention or variant thereof), thereby generating an Fc region variant (see e.g., US 2012/0251531). The Fc region variant may comprise a human Fc region sequence (e.g., a human IgG1, IgG2, IgG3 or IgG4 Fc region) comprising an amino acid modification (e.g., a substitution) at one or more amino acid positions.

In certain embodiments, the invention contemplates an anti-CD3 antibody variant that possesses some but not all effector functions, which make it a desirable candidate for applications in which the half life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express Fc(RIII only, whereas monocytes express Fc(RI, Fc(RII and Fc(RIII. FcR expression on hematopoietic cells is summarized in Table 3 on page 464 of Ravetch and Kinet, *Annu. Rev. Immunol.* 9:457-492 (1991). Non-limiting examples of in vitro assays to assess ADCC activity of a molecule of interest is described in U.S. Pat. No. 5,500,362 (see, e.g. Hellstrom, I. et al. *Proc. Nat'l Acad. Sci. USA* 83:7059-7063 (1986)) and Hellstrom, I et al., *Proc. Nat Acad. Sci. USA* 82:1499-1502 (1985); U.S. Pat. No. 5,821,337 (see Bruggemann, M. et al., *J. Exp. Med.* 166:1351-1361 (1987)). Alternatively, non-radioactive assays methods may be employed (see, for example, ACTI™ non-radioactive cytotoxicity assay for flow cytometry (CellTechnology, Inc. Mountain View, Calif.; and CYTOTOX 96® non-radioactive cytotoxicity assay (PROMEGA®, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. *Proc. Nat'l Acad. Sci. USA* 95:652-656 (1998). C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al. *J. Immunol. Methods* 202:163 (1996); Cragg, M. S. et al. *Blood.* 101:1045-1052 (2003); and Cragg, M. S. and M. J. Glennie *Blood.* 103:2738-2743 (2004)). FcRn binding and in vivo clearance/half life determinations can also be performed using methods known in the art (see, e.g., Petkova, S. B. et al. *Int'l. Immunol.* 18(12):1759-1769 (2006)).

Antibodies with reduced effector function include those with substitution of one or more of Fc region residues 238, 265, 269, 270, 297, 327 and 329 (U.S. Pat. Nos. 6,737,056 and 8,219,149). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. Nos. 7,332,581 and 8,219,149).

In certain embodiments, the proline at position 329 of a wild-type human Fc region in the antibody is substituted with glycine or arginine or an amino acid residue large enough to destroy the proline sandwich within the Fc/Fc.gamma. receptor interface that is formed between the proline 329 of the Fc and tryptophan residues Trp 87 and Trp 110 of FcgRIII (Sondermann et al. *Nature.* 406, 267-273, 2000). In certain embodiments, the antibody comprises at least one further amino acid substitution. In one embodiment, the further amino acid substitution is S228P, E233P, L234A, L235A, L235E, N297A, N297D, or P331S, and still in another embodiment the at least one further amino acid substitution is L234A and L235A of the human IgG1 Fc region or S228P and L235E of the human IgG4 Fc region (see e.g., US 2012/0251531), and still in another embodiment the at least one further amino acid substitution is L234A and L235A and P329G of the human IgG1 Fc region.

Certain antibody variants with improved or diminished binding to FcRs are described. (See, e.g., U.S. Pat. No. 6,737,056; WO 2004/056312, and Shields et al., *J. Biol. Chem.* 9(2): 6591-6604 (2001).)

In certain embodiments, an antibody variant comprises an Fc region with one or more amino acid substitutions which improve ADCC, e.g., substitutions at positions 298, 333, and/or 334 of the Fc region (EU numbering of residues).

In some embodiments, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie et al. *J. Immunol.* 164:4178-4184 (2000).

Antibodies with increased half lives and improved binding to the neonatal Fc receptor (FcRn), which is responsible for the transfer of maternal IgGs to the fetus (Guyer et al., *J. Immunol.* 117:587 (1976) and Kim et al., *J. Immunol.* 24249 (1994)), are described in US2005/0014934A1 (Hinton et al.). Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826).

See also Duncan & Winter, *Nature* 322:738-40 (1988); U.S. Pat. Nos. 5,648,260; 5,624,821; and WO 94/29351 concerning other examples of Fc region variants.

In some aspects the anti-CD3 antibody (e.g., bispecific anti-CD3 antibody) comprises an Fc region comprising an N297G mutation. In some embodiments, the anti-CD3 antibody comprising the N297G mutation comprises an anti-CD3 arm comprising a first binding domain comprising the following six HVRs: (a) an HVR-H1 comprising the amino acid sequence of SEQ ID NO: 1; (b) an HVR-H2 comprising the amino acid sequence of SEQ ID NO: 2; (c) an HVR-H3 comprising the amino acid sequence of SEQ ID NO: 3; (d) an HVR-L1 comprising the amino acid sequence of SEQ ID NO: 4; (e) an HVR-L2 comprising the amino acid sequence of SEQ ID NO: 5; and (f) an HVR-L3 comprising the amino acid sequence of SEQ ID NO: 6; and an anti-Ly6G6D arm.

In some embodiments, the anti-CD3 antibody comprising the N297G mutation comprises an anti-CD3 arm comprising a first binding domain comprising (a) a VH domain comprising an amino acid sequence of SEQ ID NO: 7 and (b) a VL domain comprising an amino acid sequence of SEQ ID NO: 8, and an anti-Ly6G6D arm.

In some embodiments, the anti-CD3 antibody comprising the N297G mutation comprises one or more heavy chain constant domains, wherein the one or more heavy chain constant domains are selected from a first CH1 ($CH1_1$) domain, a first CH2 ($CH2_1$) domain, a first CH3 ($CH3_1$) domain, a second CH1 ($CH1_2$) domain, second CH2 ($CH2_2$) domain, and a second CH3 ($CH3_2$) domain. In some instances, at least one of the one or more heavy chain constant domains is paired with another heavy chain constant domain. In some instances, the $CH3_1$ and $CH3_2$ domains each comprise a protuberance or cavity, and wherein the protuberance or cavity in the $CH3_1$ domain is positionable in the cavity or protuberance, respectively, in the $CH3_2$ domain. In some instances, the $CH3_1$ and $CH3_2$ domains meet at an interface between said protuberance and cavity. In some instances, the $CH2_1$ and $CH2_2$ domains each comprise a protuberance or cavity, and wherein the protuberance or cavity in the $CH2_1$ domain is positionable in the cavity or protuberance, respectively, in the $CH2_2$ domain. In other instances, the $CH2_1$ and $CH2_2$ domains meet at an interface between said protuberance and cavity. In some instances, the anti-CD3 antibody is an IgG1 antibody.

In other embodiments, the anti-CD3 antibody comprising the N297G mutation comprises an anti-CD3 arm comprising a first binding domain comprising (a) a VH domain comprising an amino acid sequence of SEQ ID NO: 7 and (b) a VL domain comprising an amino acid sequence of SEQ ID NO: 8, and an anti-Ly6G6D arm, wherein (a) the anti-CD3 arm comprises T366S, L368A, Y407V, and N297G substitution mutations and (b) the anti-Ly6G6D arm comprises T366W and N297G substitution mutations.

d. Cysteine Engineered Antibody Variants

In certain embodiments, it may be desirable to create cysteine engineered antibodies, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain embodiments, any one or more of the following residues may be substituted with cysteine: V205 (Kabat numbering) of the light chain; A118 (EU numbering) of the heavy chain; and S400 (EU numbering) of the heavy chain Fc region. Cysteine engineered antibodies may be generated as described, for example, in U.S. Pat. No. 7,521,541.

e. Antibody Derivatives

In certain embodiments, an anti-CD3 antibody of the invention (e.g., bispecific anti-CD3 antibody of the invention that binds to CD3, preferably with high affinity (e.g., 38E4v11), and a second biological molecule, e.g., a cell surface antigen, e.g., a tumor antigen, such as a TDB antibody of the invention or variant thereof) provided herein may be further modified to contain additional nonproteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1, 3-dioxolane, poly-1,3,6-trioxane, ethylene/maleic anhydride copolymer, polyaminoacids (either homopolymers or random copolymers), and dextran or poly(n-vinyl pyrrolidone)polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and nonproteinaceous moiety that may be selectively heated by exposure to radiation are provided. In one embodiment, the nonproteinaceous moiety is a carbon nanotube (Kam et al., *Proc. Na. Acad. Sci. USA* 102:11600-11605 (2005)). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

7. Masked Antibody Variants

In certain embodiments, any one of the anti-CD3 antibodies described herein (e.g., a bispecific anti-CD3 antibody, e.g., a Ly6G6D TDB antibody) may include a polypeptide mask, wherein the polypeptide mask comprises a masking moiety (MM) comprising the amino acid sequence of at least amino acid residues 1-3 of SEQ ID NO: 78 (e.g., a polypeptide mask comprising a MM comprising amino acid residues 1-3, 1-4, 1-5, 1-6, 1-7, 1-8, 1-9, 1-10, 1-11, 1-12, 1-13, 1-14, 1-15, 1-16, 1-17, 1-18, 1-19, 1-20, 1-21, 1-22, 1-23, 1-24, 1-25, 1-26, or 1-27 of SEQ ID NO: 78), or an N-terminal cyclicized glutamine derivative thereof (e.g., a polypeptide mask comprising a MM comprising 5-oxopyrrolidine-2-carboxyic acid (PCA)). For example, in some embodiments, the MM comprises at least the first three amino acid residues of SEQ ID NO: 78, except that the residue at position 1 is an N-terminal cyclicized glutamine (PCA) residue instead of a glutamine residue (e.g., the MM comprises the amino acid sequence PCA-D-G). In some embodiments, the anti-CD3 antibody comprises at least one anti-CD3 arm (e.g., an anti-CD3 arm comprising the heavy chain variable (VH) domain and a light chain variable (VL) domain of 38E4v11), and the polypeptide mask is joined to anti-CD3 arm (e.g., via the VH domain or the VL domain of the anti-CD3 arm). In some embodiments, the MM is extended at the C-terminus by all or a portion of the remaining sequence of SEQ ID NO: 78. For example, in some embodiments, the MM comprises the amino acid sequence of at least amino acid residues 1-5 of SEQ ID NO: 78, or an N-terminal cyclicized glutamine derivative thereof (e.g., a polypeptide mask comprising a MM comprising at least the first five amino acid residues of SEQ ID NO: 1, except that the residue at position 1 is PCA instead of a glutamine). In other embodiments, the MM comprises the amino acid sequence of at least amino acid residues 1-6 of SEQ ID NO: 78, or an N-terminal cyclicized glutamine derivative thereof (e.g., a polypeptide mask comprising a MM comprising at least the first six amino acid residues of SEQ ID NO: 78, except that the residue at position 1 is PCA instead of glutamine). In some embodiments, the anti-CD3 antibody and MM are positioned relative to each other in an N-terminal to C-terminal direction as (MM)-(anti-CD3 antibody). In some instances, the MM is extended, either directly or indirectly, at one end (i.e., the C-terminal end) by a non-native CD3 polypeptide sequence, such as a cleavable moiety (CM) and/or linker moiety (LM).

As noted above, the masked anti-CD3 antibody (e.g., a masked bispecific anti-CD3 antibody, e.g., a masked Ly6G6D TDB antibody) may comprise a polypeptide mask having both a MM and a cleavable moiety (CM). In some embodiments, the CM contains an amino acid sequence that is capable of being cleaved by an enzyme, such as a protease. In other embodiments, the CM provides a cysteine-cysteine disulfide bond that is cleavable by reduction. In additional embodiments, the CM provides an acid-labile linker that is cleaved in the presence of an acidic pH environment. In yet other embodiments, the CM provides a photolytic substrate that is activatable by photolysis.

Accordingly, a masked anti-CD3 antibody (e.g., a masked Ly6G6D TDB antibody) comprising a polypeptide mask with a CM can exist in either a cleaved state or an uncleaved state. As used herein, the term cleaved state refers to the condition of the anti-CD3 antibody following modification of the CM, for example, by a protease, reduction of a cysteine-cysteine disulfide bond of the CM, and/or photo-activation. The term uncleaved state, as used herein, refers to the condition of the anti-CD3 antibody in the absence of cleavage of the CM, for example, by a protease, in the absence reduction of a cysteine-cysteine disulfide bond of the CM, in the absence of an acidic pH environment (e.g., in a neutral or basic pH environment), and/or in the absence of light. It will be apparent to the ordinarily skilled artisan that in some embodiments a cleaved anti-CD3 antibody may lack an MM due to cleavage of the CM by, for example, a protease, resulting in release of at least the MM. Thus, when a masked anti-CD3 antibody is in the uncleaved state, the masked anti-CD3 antibody would show reduced binding to CD3 because the binding domain of the antibody is effectively masked from the CD3 target molecule. In the cleaved state, the anti-CD3 antibody would show higher affinity for CD3 than an antibody it would in its uncleaved state because the binding domain of the antibody would no longer be inhibited by the MM of the polypeptide mask.

When the CM is capable of being cleaved by an enzyme (e.g., a protease) and the masked anti-CD3 antibody is a TDB, the enzyme may be selected based on a protease that is co-localized in tissue with the desired target of the TDB. A variety of different conditions are known in which a target of interest is co-localized with a protease, where the substrate of the protease is known in the art. In the example of cancer, the target tissue can be a cancerous tissue, particularly cancerous tissue of a solid tumor. Increased levels of proteases having known substrates in a number of cancers, such as solid tumors, are known in the art (see, e.g., La Rocca et al. *British J. of Cancer.* 90(7):1414-1421, 2004 and Lopez-Otin et al. *Nat Rev Cancer.* 7: 800-808, 2007). Exemplary CMs can include, but are not limited to, substrates that are cleavable by one or more of the enzymes (e.g., proteases) specified in WO 2010/081173, WO 2009/025846, WO 2010/096838, and/or one or more of the following enzymes listed below in Table 3.

TABLE 3

Exemplary Enzymes

| Plasmin | Legumain asparaginyl endopeptidase | Transmembrane Protease | Serine (TMPRSS-3/4) |
|---|---|---|---|
| Matrix Metalloprotease (MMP)-1 | MMP-2 | MMP-3 | MMP-7 |
| MMP-8 | MMP-9 | MMP-12 | MMP-13 |
| MMP-14 | Membrane type 1 matrix metalloprotease (MT1-MMP) | Cathepsin A | Cathepsin B |
| Cathepsin D | Cathepsin E | Cathepsin F | Cathepsin H |
| Cathepsin K | Cathepsin K | Cathepsin L | Cathepsin L2 |
| Cathepsin O | Cathepsin S | Caspase 1 | Caspase 2 |
| Caspase 3 | Caspase 4 | Caspase 5 | Caspase 6 |
| Caspase 7 | Caspase 8 | Caspase 9 | Caspase 10 |
| Caspase 11 | Caspase 12 | Caspase 13 | Caspase 14 |
| Human Neutrophil Elastase | Urokinase/urokinase-Type Plasminogen Activator (uPA) | A Disintegrin and Metalloprotease (ADAM)10 | ADAM12 |
| ADAM17 | ADAM with Thrombospondin Motifs (ADAMTS) | ADAMTS5 | Beta Secretase (BACE) |
| Fibroblast Activation Protease (FAP) | Granzyme A | Granzyme B | Guanidinobenzoatase |
| Gepsin | Matriptase | Matriptase 2 | Meprin |
| Neprilysin | Prostate-Specific Membrane Antigen (PSMA) | Tumor Necrosis Factor-Converting Enzyme (TACE) | Kallikrein-Related Peptidase (KLK)3 |

TABLE 3-continued

Exemplary Enzymes

| Plasmin | Legumain asparaginyl endopeptidase | Transmembrane Protease | Serine (TMPRSS-3/4) |
|---|---|---|---|
| KLK5 | KLK7 | KLK11 | NS3/4 Protease of Hepatitis C Virus (HCV-NS3/4) |
| Tissue Plasminogen Activator (tPA) | Calpain | Calpain 2 | Glutamate Carboxypeptidase II |
| Plasma Kallikrein | AMSH-Like Protease | AMSH Apoptosis-Related Cysteine Peptidase | γ-Secretase Component N-Acetylated Alpha-Linked Acidic Dipeptidase-Like 1 |
| Antiplasmin Cleaving Enzyme (APCE) | Decysin 1 | | |
| Thrombin | | | |

Alternatively or in addition, the masked anti-CD3 antibody can comprise a CM that includes a disulfide bond of a cysteine pair, which is thus cleavable by a reducing agent. These include, but are not limited to, acellular reducing agent such as glutathione (GSH), thioredoxins, NADPH, flavins, ascorbate, and the like, which can be present in large amounts in tissue of or surrounding a solid tumor.

In other embodiments, the masked anti-CD3 antibody can comprise a CM that includes an acid-labile linker (e.g., a hydrazone, an imino, an ester, or an amido group) which is thus cleavable in the presence of an acidic pH environment, as described in PCT publication number WO 2006108052, which is herein incorporated by reference in its entirety. This includes, but is not limited to, an acidic pH environment that can be present in lysosomes of a cell or in a tumor microenvironment.

The CM may be positioned relative to the anti-CD3 antibody and MM in an N-terminal to C-terminal direction as (MM)-(CM)-(anti-CD3 antibody).

In other embodiments, the masked anti-CD3 antibody (e.g., a masked Ly6G6D TDB antibody) can include one or more (e.g., 2 or 3 or more) distinct CMs within its polypeptide mask.

As noted above, the masked anti-CD3 antibody (e.g., a masked Ly6G6D TDB antibody) may comprise a polypeptide mask having both a MM and a linker moiety (LM), or, alternatively, all three moieties (i.e., a MM, LM, and CM). LMs suitable for use in a polypeptide mask described herein are generally ones that provide flexibility and/or length to the mask to facilitate or modulate the degree of inhibition of the binding of the anti-CD3 antibody to CD3. Such LMs can also be referred to as flexible linkers. Suitable LMs can be readily selected and can be of different suitable lengths, such as from 1 amino acid (e.g., one glycine (G) or one serine (S) residue) to 30 amino acids (e.g., a LM containing a GS repeat sequence). A LM is preferably greater than one amino acid in length (e.g, 2, 3, 4, 5, 6, 7, 8, 9, 10, 11, 12, 13, 14, 15, 16, 17, 18, 19, 20, 21, 22, 23, 24, 25, 26, 27, 28, 29, or 30 or more amino acids in length). In some instances, the LM can be between 5 to 24 amino acids in length, such as between 5 to 15 amino acids in length. The LM may high in G and/or S content (i.e. a G/S-rich LM) and may include GS repeats. For example, the LM may include glycine polymers $(G)_n$, glycine-serine polymers (including, for example, $(GS)_n$, $(GSGGS)_n$ and $(GGGS)_n$, where n is an integer of at least one), glycine-alanine polymers, alanine-serine polymers, and other flexible linker combinations known in the art. Glycine and glycine-serine polymers are relatively unstructured, and therefore may be able to serve as a neutral LM that indirectly or directly joins the MM component of the polypeptide mask to the anti-CD3 antibody. Glycine accesses significantly more phi-psi space than even alanine, and is much less restricted than residues with longer side chains (see, e.g., Scheraga. Rev. Computational Chem. 11173-142, 1992). Exemplary flexible linkers include, but are not limited to Gly-Gly-Ser-Gly, Gly-Gly-Ser-Gly-Gly, Gly-Ser-Gly-Ser-Gly, Gly-Ser-Gly-Gly-Gly, Gly-Gly-Gly-Ser-Gly, Gly-Ser-Ser-Ser-Gly, and the like. The ordinarily skilled artisan will recognize that design of a polypeptide mask can include a LM that is completely or partially flexible. For example, a LM may include a flexible portion as well as one or more portions that confer less flexible structure to yield a masked anti-CD3 antibody exhibiting a desired degree of inhibition of CD3 binding, which can be assessed using, for example, an assay such as the phage binding ELISA described in detail below.

When the polypeptide mask does not include a CM, the LM may be positioned relative to the anti-CD3 antibody and MM in an N-terminal to C-terminal direction as (MM)-(LM)-(anti-CD3 antibody). When the polypeptide mask does include a CM, the LM may be positioned relative to the anti-CD3 antibody, MM, and CM in an N-terminal to C-terminal direction as (MM)-(LM)-(CM)-(anti-CD3 antibody) or (MM)-(CM)-(LM)-(anti-CD3 antibody).

In other embodiments, the masked anti-CD3 antibody (e.g., a masked Ly6G6D TDB antibody) can include one or more (e.g., 2 or 3 or more) distinct CMs within its polypeptide mask.

B. Recombinant Methods and Compositions

Anti-CD3 antibodies of the invention (e.g., bispecific anti-CD3 antibodies of the invention that bind to CD3, preferably with high affinity (e.g., 38E4v11), and a second biological molecule, e.g., a cell surface antigen, e.g., a tumor antigen, such as TDB antibodies of the invention or variants thereof) may be produced using recombinant methods and compositions, for example, as described in U.S. Pat. No. 4,816,567. In one embodiment, isolated nucleic acid encoding an anti-CD3 antibody described herein is provided. Such nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, e.g. a Chinese Hamster Ovary (CHO) cell or lymphoid cell (e.g., Y0, NS0, Sp20 cell). In one embodiment, a method of making an anti-CD3 antibody is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an anti-CD3 antibody, nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosyation and Fc effector function are not needed. For expression of antibody fragments and polypeptides in bacteria, see, e.g., U.S. Pat. Nos. 5,648,237, 5,789,199, and 5,840,523. (See also Charlton, *Methods in Molecular Biology*, Vol. 248 (B. K. C. Lo, ed., Humana Press, Totowa, N.J., 2003), pp. 245-254, describing expression of antibody fragments in *E. coli*.) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosyation pattern. See Gerngross, *Nat. Biotech.* 22:1409-1414 (2004), and Li et al., *Nat. Biotech.* 24:210-215 (2006).

Suitable host cells for the expression of glycosyated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., *J. Gen Virol.* 36:59 (1977)); baby hamster kidney cells (BHK); mouse sertoli cells (TM4 cells as described, e.g., in *Mather, Biol. Reprod.* 23:243-251 (1980)); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al., *Annals N. Y. Acad. Sci.* 383:44-68 (1982); MRC 5 cells; and FS4 cells. Other useful mammalian host cell lines include Chinese hamster ovary (CHO) cells, including DHFR$^-$ CHO cells (Urlaub et al., *Proc. Natl. Acad. Sci. USA* 77:4216 (1980)); and myeloma cell lines such as Y0, NS0 and Sp2/0. For a review of certain mammalian host cell lines suitable for antibody production, see, e.g., Yazaki and Wu, *Methods in Molecular Biology*, Vol. 248 (B. K. C. Lo, ed., Humana Press, Totowa, N.J.), pp. 255-268 (2003).

C. Assays

Anti-CD3 antibodies of the invention (e.g., bispecific anti-CD3 antibodies of the invention that bind to CD3, preferably with high affinity (e.g., 38E4v11), and a second biological molecule, e.g., a cell surface antigen, e.g., a tumor antigen, such as TDB antibodies of the invention or variants thereof) provided herein may be identified, screened for, or characterized for their physical/chemical properties and/or biological activities by various assays known in the art.

1. Binding Assays and Other Assays

In one aspect, an anti-CD3 antibody of the invention is tested for its antigen binding activity, for example, by known methods such as ELISA, Western blot, etc.

In another aspect, competition assays may be used to identify an antibody that competes with an anti-CD3 antibody of the invention for binding to CD3.

In an exemplary competition assay, immobilized CD3 is incubated in a solution comprising a first labeled antibody that binds to CD3 and a second unlabeled antibody that is being tested for its ability to compete with the first antibody for binding to CD3. The second antibody may be present in a hybridoma supernatant. As a control, immobilized CD3 is incubated in a solution comprising the first labeled antibody but not the second unlabeled antibody. After incubation under conditions permissive for binding of the first antibody to CD3, excess unbound antibody is removed, and the amount of label associated with immobilized CD3 is measured. If the amount of label associated with immobilized CD3 is substantially reduced in the test sample relative to the control sample, then that indicates that the second antibody is competing with the first antibody for binding to CD3. See, e.g., Harlow and Lane (1988) *Antibodies: A Laboratory Manual*. Ch. 14 (Cold Spring Harbor Laboratory, Cold Spring Harbor, N.Y.).

2. Activity Assays

In one aspect, assays are provided for identifying anti-CD3 antibodies thereof having biological activity. Biological activity may include, for example, binding to CD3 (e.g., CD3 on the surface of a T cell), or a peptide fragment thereof, either in vivo, in vitro, or ex vivo. In the case of a multispecific (e.g., bispecific) anti-CD3 antibody of the invention (e.g., a TDB antibody having one anti-CD3 arm, e.g., 38E4v11, and one arm that recognizes a second biological molecule, e.g., a cell surface antigen, e.g., a tumor antigen), biological activity may also include, for example, effector cell activation (e.g., T cell (e.g., CD8+ and/or CD4+ T cell) activation), effector cell population expansion (i.e., an increase in T cell count), target cell population reduction (i.e., a decrease in the population of cells expressing the second biological molecule on their cell surfaces), and/or target cell killing. Antibodies having such biological activity in vivo and/or in vitro are provided. In certain embodiments, an antibody of the invention is tested for such biological activity, as described in detail in the Example 2 herein below.

Further, cells may be washed in RPMI medium containing 10% FBS, supplemented with GlutaMax, penicillin & streptomycin, and ~0.2 million suspended cells added to a 96-well U-bottom plate. Cells may be cultured in RPMI1640 supplemented with 10% FBS at 37° C. in a humidified standard cell culture incubator. For BJAB cell killing assays, 20,000 BJAB cells may be incubated with effector cells, either as huPBMCs or purified T cells, as indicated ratios per assay, in the presence of various concentrations of TDB antibodies for 24 hours. For endogenous B cell killing assays, 200,000 huPBMCs may be incubated with various concentrations of TDB antibodies for 24 hours.

After culturing, cells may be washed with FACS buffer (0.5% BSA, 0.05% Na Azide in PBS). Cells may then be stained in FACS buffer, washed with FACS buffer and suspended in 100 µl of FACS buffer containing 1 µg/ml Propidium Iodide. Data may be collected on a FACSCalibur flow cytometer and analyzed using FlowJo. Live B cells may be gated out as PI-CD19+ or PI-CD20+ B cells by FACS, and absolute cell count may be obtained with FITC beads added to reaction mix as an internal counting control. The percent (%) of cell killing may be calculated based on non-TDB treated controls. Activated T cells may be detected by CD69 and CD25 surface expression using anti-CD69-FITC and anti-CD25-PE.

D. Immunoconjugates

The invention also provides immunoconjugates comprising an anti-CD3 antibody herein conjugated to one or more cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes.

In one embodiment, an immunoconjugate is an antibody-drug conjugate (ADC) in which an antibody is conjugated to one or more drugs, including but not limited to a maytansinoid (see U.S. Pat. Nos. 5,208,020, 5,416,064 and European Patent EP 0 425 235 B1); an auristatin such as monomethyauristatin drug moieties DE and DF (MMAE and MMAF) (see U.S. Pat. Nos. 5,635,483 and 5,780,588, and 7,498,298); a dolastatin; a calicheamicin or derivative thereof (see U.S. Pat. Nos. 5,712,374, 5,714,586, 5,739,116, 5,767,285, 5,770,701, 5,770,710, 5,773,001, and 5,877,296; Hinman et al., *Cancer Res.* 53:3336-3342 (1993); and Lode et al., *Cancer Res.* 58:2925-2928 (1998)); an anthracycline such as daunomycin or doxorubicin (see Kratz et al., *Current Med. Chem.* 13:477-523 (2006); Jeffrey et al., *Bloorganic & Med. Chem. Letters* 16:358-362 (2006); Torgov et al., *Bioconj. Chem.* 16:717-721 (2005); Nagy et al., *Proc. Natl. Acad. Sci. USA* 97:829-834 (2000); Dubowchik et al., *Bioorg. & Med. Chem. Letters* 12:1529-1532 (2002); King et al., *J. Med. Chem.* 45:4336-4343 (2002); and U.S. Pat. No. 6,630,579); methotrexate; vindesine; a taxane such as docetaxel, paclitaxel, larotaxel, tesetaxel, and ortataxel; a trichothecene; and CC1065.

In another embodiment, an immunoconjugate comprises an anti-CD3 antibody as described herein conjugated to an enzymatically active toxin or fragment thereof, including but not limited to diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes.

In another embodiment, an immunoconjugate comprises an anti-CD3 antibody as described herein conjugated to a radioactive atom to form a radioconjugate. A variety of radioactive isotopes are available for the production of radioconjugates. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the radioconjugate is used for detection, it may comprise a radioactive atom for scintigraphic studies, for example tc99m or 1123, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or iron.

Conjugates of an antibody and cytotoxic agent may be made using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., *Science* 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of a cytotoxic drug in the cell. For example, an acid-labile linker, peptidase-sensitive linker, photolabile linker, dimethyl linker or disulfide-containing linker (Chari et al., *Cancer Res.* 52:127-131 (1992); U.S. Pat. No. 5,208,020) may be used.

The immunoconjugates or ADCs herein expressly contemplate, but are not limited to such conjugates prepared with cross-linker reagents including, but not limited to, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinysulfone)benzoate) which are commercially available (e.g., from Pierce Biotechnology, Inc., Rockford, Ill., U.S.A).

E. Methods and Compositions for Diagnostics and Detection

In certain embodiments, any of the anti-CD3 antibodies of the invention (e.g., bispecific anti-CD3 antibodies of the invention that bind to CD3, preferably with high affinity (e.g., 38E4v11), and a second biological molecule, e.g., a cell surface antigen, e.g., a tumor antigen, such as TDB antibodies of the invention or variants thereof) is useful for detecting the presence of CD3 in a biological sample. The term "detecting" as used herein encompasses quantitative or qualitative detection. In certain embodiments, a biological sample comprises a cell or tissue.

In one embodiment, an anti-CD3 antibody for use in a method of diagnosis or detection is provided. In a further aspect, a method of detecting the presence of CD3 in a biological sample is provided. In certain embodiments, the method comprises contacting the biological sample with an anti-CD3 antibody as described herein under conditions permissive for binding of the anti-CD3 antibody to CD3, and detecting whether a complex is formed between the anti-CD3 antibody and CD3. Such method may be an in vitro or in vivo method.

In certain embodiments, labeled anti-CD3 antibodies are provided. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}$P, $^{14}$C, $^{125}$I, $^{3}$H, and $^{131}$I, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

F. Pharmaceutical Formulations

Pharmaceutical formulations of an anti-CD3 antibody of the invention (e.g., bispecific anti-CD3 antibody of the invention that binds to CD3, preferably with high affinity (e.g., 38E4v11), and a second biological molecule, e.g., a cell surface antigen, e.g., a tumor antigen, such as a TDB antibody of the invention or variant thereof) are prepared by mixing such antibody having the desired degree of purity with one or more optional pharmaceutically acceptable carriers (*Remington's Pharmaceutical Sciences* 16th edition, Osol, A. Ed. (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecydimethybenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Exemplary pharmaceutically acceptable carriers herein further include insterstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases.

Exemplary lyophilized antibody formulations are described in U.S. Pat. No. 6,267,958. Aqueous antibody formulations include those described in U.S. Pat. No. 6,171,586 and WO2006/044908, the latter formulations including a histidine-acetate buffer.

The formulation herein may also contain more than one active ingredients as necessary for the particular indication being treated, preferably those with complementary activities that do not adversely affect each other. For example, it may be desirable to further provide an additional therapeutic agent (e.g., a chemotherapeutic agent, a cytotoxic agent, a growth inhibitory agent, and/or an anti-hormonal agent, such as those recited herein above). Such active ingredients are suitably present in combination in amounts that are effective for the purpose intended.

Active ingredients may be entrapped in microcapsules prepared, for example, by coacervation techniques or by interfacial polymerization, for example, hydroxymethylcellulose or gelatin-microcapsules and poly-(methylmethacyate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

Sustained-release preparations may be prepared. Suitable examples of sustained-release preparations include semipermeable matrices of solid hydrophobic polymers containing the antibody, which matrices are in the form of shaped articles, for example, films, or microcapsules.

The formulations to be used for in vivo administration are generally sterile. Sterility may be readily accomplished, e.g., by filtration through sterile filtration membranes.

G. Therapeutic Methods and Compositions

Any of the anti-CD3 antibodies of the invention (e.g., bispecific anti-CD3 antibodies of the invention that bind to CD3, preferably with high affinity (e.g., 38E4v11), and a second biological molecule, e.g., a cell surface antigen, e.g., a tumor antigen, may be used in therapeutic methods. The high affinity anti-CD3 antibodies of the invention affinity, for example, 38E4v11, find particular use when paired with a targeting arm that binds to a cell surface antigen that is expressed at low copy number on tumor cells. In some embodiments, the low copy number cell surface antigen is Ly6G6D.

In one aspect, an anti-CD3 antibody for use as a medicament is provided. In further aspects, an anti-CD3 antibody for use in treating or delaying progression of a cell proliferative disorder (e.g., cancer, e.g., esophageal cancer or an adenocarcinoma) or an autoimmune disorder (e.g., arthritis) is provided. In certain embodiments, an anti-CD3 antibody for use in a method of treatment is provided. In certain embodiments, the invention provides an anti-CD3 antibody for use in a method of treating an individual having a cell proliferative disorder or an autoimmune disorder comprising administering to the individual an effective amount of the anti-CD3 antibody. In one such embodiment, the method further comprises administering to the individual an effective amount of at least one additional therapeutic agent, for example, as described below. In further embodiments, the invention provides an anti-CD3 antibody for use in enhancing immune function in an individual having a cell proliferative disorder or an autoimmune disorder. In certain embodiments, the invention provides an anti-CD3 antibody for use in a method of enhancing immune function in an individual having a cell proliferative disorder or an autoimmune disorder comprising administering to the individual an effective of the anti-CD3 antibody to activate effector cells (e.g., T cells, e.g., CD8+ and/or CD4+ T cells), expand (increase) an effector cell population, reduce a target cell (e.g., a cell expressing a second biological molecule recognized by an anti-CD3 antibody of the invention, such as a bispecific TDB antibody of the invention) population, and/or kill a target cell (e.g., target tumor cell). An "individual" according to any of the above embodiments may be a human.

In a further aspect, the invention provides for the use of an anti-CD3 antibody in the manufacture or preparation of a medicament. In one embodiment, the medicament is for treatment of a cell proliferative disorder (e.g., cancer, e.g., esophageal cancer or an adenocarcinoma) or an autoimmune disorder (e.g., arthritis). In a further embodiment, the medicament is for use in a method of treating a cell proliferative disorder or an autoimmune disorder comprising administering to an individual having a cell proliferative disorder or an autoimmune disorder an effective amount of the medicament. In one such embodiment, the method further comprises administering to the individual an effective amount of at least one additional therapeutic agent, for example, as described below. In a further embodiment, the medicament is for activating effector cells (e.g., T cells, e.g., CD8+ and/or CD4+ T cells), expanding (increasing) an effector cell population, reducing a target cell (e.g., a cell expressing a second biological molecule recognized by an anti-CD3 antibody of the invention, such as a bispecific TDB antibody of the invention) population, and/or killing target cells (e.g., target tumor cells) in the individual. In a further embodiment, the medicament is for use in a method of enhancing immune function in an individual having a cell proliferative disorder or an autoimmune disorder comprising administering to the individual an amount effective of the medicament to activate effector cells (e.g., T cells, e.g., CD8+ and/or CD4+ T cells), expand (increase) an effector cell population, reduce a target cell (e.g., a cell expressing a second biological molecule recognized by an anti-CD3 antibody of the invention, such as a bispecific TDB antibody of the invention) population, and/or kill a target cell (e.g., target tumor cell). An "individual" according to any of the above embodiments may be a human.

In a further aspect, the invention provides a method for treating a cell proliferative disorder (e.g., cancer, e.g., esophageal cancer or an adenocarcinoma) or an autoimmune disorder (e.g., arthritis). In one embodiment, the method comprises administering to an individual having such a cell proliferative disorder or an autoimmune disorder an effective amount of an anti-CD3 antibody. In one such embodiment, the method further comprises administering to the individual an effective amount of at least one additional therapeutic agent, for example, as described below. An "individual" according to any of the above embodiments may be a human.

In a further aspect, the invention provides a method for enhancing immune function in an individual having a cell proliferative disorder or an autoimmune disorder in an individual having a cell proliferative disorder or an autoimmune disorder. In one embodiment, the method comprises administering to the individual an effective amount of an anti-CD3 antibody to activate effector cells (e.g., T cells, e.g., CD8+ and/or CD4+ T cells), expand (increase) an effector cell population, reduce a target cell (e.g., a cell expressing a second biological molecule recognized by an anti-CD3 antibody of the invention, such as a bispecific TDB antibody of the invention) population, and/or kill a target cell (e.g., target tumor cell). In one embodiment, an "individual" is a human.

In a further aspect, the invention provides a method for treating esophageal cancer, stomach cancer, small intestine cancer, large intestine cancer, colorectal cancer, or an adenocarcinoma (e.g., colorectal adenocarcinoma, gastric adenocarcinoma, or pancreatic adenocarcinoma), which may be metastatic adenocarcinoma (e.g., metastatic colorectal adenocarcinoma, metastatic gastric adenocarcinoma, or metastatic pancreatic adenocarcinoma), by administering an effective amount of an anti-CD3 antibody of the invention, such as a bispecific TDB antibody of the invention, such as an anti-Ly6G6D targeting TDB, such as a Ly6G6D TDB having an affinity matured (e.g., high affinity) anti-CD3 arm, such as 38E4v11, and an anti-Ly6G6D arm. In other embodiments, a Ly6G6D TDB is co-administered (concurrently, as a single or multiple compositions (e.g., formulations)) with one or more additional therapeutic agents, such as any one, two, three, four, five, six, seven, eight, nine, ten, or all eleven of the following: FOLFOX (oxaliplatin (ELOXATIN™) combined with 5-fluorouracil and leucovorin), capecitabine (XELODA®), 5-fluorouracil (5-FU), CapeOx (XELOX®; capecitabine with oxaliplatin), leucovorin (folinic acid), bevacizumab (AVASTIN®), cetuximab (ERBITUX®), panitumumab (VECTIBIX®), regorafenib (STIVARGA®), irinotecan (CPT-11; CAMPTOSAR®), and FLOX (5-fluorouracil with oxaliplatin). In other embodiments, a Ly6G6D TDB is administered before one or more additional therapeutic agents, such as any one, two, three, four, five, six, seven, eight, nine, ten, or all eleven of the following: FOLFOX (oxaliplatin (ELOXATIN™) combined with 5-fluorouracil and leucovorin), capecitabine (XELODA®), 5-fluorouracil (5-FU), CapeOx (XELOX®; capecitabine with oxaliplatin), leucovorin (folinic acid), bevacizumab (AVASTIN®), cetuximab (ERBITUX®), panitumumab (VECTIBIX®), regorafenib (STIVARGA®), irinotecan (CPT-11; CAMPTOSAR®), and FLOX (5-fluorouracil with oxaliplatin). In other embodiments, a Ly6G6D TDB is administered after one or more additional therapeutic agents, such as any one, two, three, four, five, six, seven, eight, nine, ten, or all eleven of the following: FOLFOX (oxaliplatin (ELOXATIN™) combined with 5-fluorouracil and leucovorin), capecitabine (XELODA®), 5-fluorouracil (5-FU), CapeOx (XELOX®; capecitabine with oxaliplatin), leucovorin (folinic acid), bevacizumab (AVASTIN®), cetuximab (ERBITUX®), panitumumab (VECTIBIX®), regorafenib (STIVARGA®), irinotecan (CPT-11; CAMPTOSAR®), and FLOX (5-fluorouracil with oxaliplatin).

In another aspect, the invention provides a method for treating a hematological cancer, such as a B cell cancer (for example, mature B-cell lymphoma) by administering an effective amount of an anti-CD3 antibody of the invention, such as a bispecific TDB antibody of the invention, such as an anti-B cell targeting TDB, such as a CD20-TDB having an anti-CD3 arm and an anti-CD20 arm. In a further aspect of the embodiment, the mature B-cell lymphoma is a Non-Hodgkin's Lymphoma (NHL). In a further aspect of the embodiment, the NHL is selected from the group comprising: germinal-center B-cell-like (GCB) DLBCL, activated B-cell-like (ABC) DLBCL, follicular lymphoma (FL), mantle cell lymphoma (MCL), acute myeloid leukemia (AML), chronic lymphoid leukemia (CLL), marginal zone lymphoma (MZL), small lymphocytic leukemia (SLL), lymphoplasmacytic lymphoma (LL), Waldenstrom macroglobulinemia (WM), central nervous system lymphoma (CNSL), Burkitt's lymphoma (BL), B-cell prolymphocytic leukemia, Splenic marginal zone lymphoma, Hairy cell leukemia, Splenic lymphoma/leukemia, unclassifiable, Splenic diffuse red pulp small B-cell lymphoma, Hairy cell leukemia variant, Waldenstrom macroglobulinemia, Heavy chain diseases, a Heavy chain disease, γ Heavy chain disease, p Heavy chain disease, Plasma cell myeloma, Solitary plasmacytoma of bone, Extraosseous plasmacytoma, Extranodal marginal zone lymphoma of mucosa-associated lymphoid tissue (MALT lymphoma), Nodal marginal zone lymphoma, Pediatric nodal marginal zone lymphoma, Pediatric follicular lymphoma, Primary cutaneous follicle centre lymphoma, T-cell/histiocyte rich large B-cell lymphoma, Primary DLBCL of the CNS, Primary cutaneous DLBCL, leg type, EBV-positive DLBCL of the elderly, DLBCL associated with chronic inflammation, Lymphomatoid granulomatosis, Primary mediastinal (thymic) large B-cell lymphoma, Intravascular large B-cell lymphoma, ALK-positive large B-cell lymphoma, Plasmablastic lymphoma, Large B-cell lymphoma arising in HHV8-associated multicentric Castleman disease, Primary effusion lymphoma: B-cell lymphoma, unclassifiable, with features intermediate between diffuse large B-cell lymphoma and Burkitt lymphoma, and B-cell lymphoma, unclassifiable, with features intermediate between diffuse large B-cell lymphoma and classical Hodgkin lymphoma. In a preferred embodiment of the invention, the method comprises treating a cancer comprising germinal-center B-cell-like (GCB) DLBCL, activated B-cell-like (ABC) DLBCL, follicular lymphoma (FL), mantle cell lymphoma (MCL), acute myeloid leukemia (AML), chronic lymphoid leukemia (CLL), marginal zone lymphoma (MZL), small lymphocytic leukemia (SLL), lymphoplasmacytic lymphoma (LL), Waldenstrom macroglobulinemia (WM), central nervous system lymphoma (CNSL), or Burkitt's lymphoma (BL).

In a further aspect, the invention provides pharmaceutical formulations comprising any of the anti-CD3 antibodies provided herein, e.g., for use in any of the above therapeutic methods. In one embodiment, a pharmaceutical formulation comprises any of the anti-CD3 antibodies provided herein and a pharmaceutically acceptable carrier. In another embodiment, a pharmaceutical formulation comprises any of the anti-CD3 antibodies provided herein and at least one additional therapeutic agent, for example, as described herein.

Antibodies of the invention can be used either alone or in combination with other agents in a therapy. For instance, an antibody of the invention may be co-administered with at least one additional therapeutic agent. In certain embodiments, an additional therapeutic agent is a chemotherapeutic agent, growth inhibitory agent, cytotoxic agent, agent used in radiation therapy, anti-angiogenesis agent, apoptotic agent, anti-tubulin agent, or other agent, such as a epidermal growth factor receptor (EGFR) antagonist (e.g., a tyrosine kinase inhibitor), HER1/EGFR inhibitor (e.g., erlotinib (Tarceva™), platelet derived growth factor inhibitor (e.g., Gleevec™ (Imatinib Mesylate)), a COX-2 inhibitor (e.g., celecoxib), interferon, cytokine, antibody other than the anti-CD3 antibody of the invention, such as an antibody that bind to one or more of the following targets ErbB2, ErbB3, ErbB4, PDGFR-beta, BlyS, APRIL, BCMA VEGF, or VEGF receptor(s), TRAIL/Apo2, PD-1, PD-1, PD-L2, or another bioactive or organic chemical agent.

In some embodiments, the invention provides a method wherein the additional therapeutic agent is a glucocorticoid. In one embodiment, the glucocorticoid is dexamethasone.

Such combination therapies noted above encompass combined administration (where two or more therapeutic agents are included in the same or separate formulations), and separate administration, in which case, administration of the antibody of the invention can occur prior to, simultaneously, and/or following, administration of the additional therapeutic agent or agents. In one embodiment, administration of the anti-CD3 antibody and administration of an additional therapeutic agent occur within about one month, or within about one, two or three weeks, or within about one, two, three, four, five, or six days, of each other. Anti-CD3 antibodies of the invention (e.g., bispecific anti-CD3 antibodies of the invention that bind to CD3 and a second biological molecule, e.g., a cell surface antigen, e.g., a tumor antigen, such as a TDB antibody of the invention or variant thereof) can also be used in combination with radiation therapy.

An antibody of the invention (and/or any additional therapeutic agent) can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. In some embodiments, the antibody is administered by subcutaneous administration. In some embodiments, an anti-CD3 antibody administered by subcutaneous injection exhibits a less toxic response in a patient than the same anti-CD3 antibody administered by intravenous injection. Dosing can be by any suitable route, for example, by injections, such as intravenous or subcutaneous injections, depending in part on whether the administration is brief or chronic. Various dosing schedules including but not limited to single or multiple administrations over various time-points, bolus administration, and pulse infusion are contemplated herein.

Antibodies of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody need not be, but is optionally formulated with one or more agents currently used to prevent or treat the disorder in question. The effective amount of such other agents depends on the amount of antibody present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of an antibody of the invention (when used alone or in combination with one or more other additional therapeutic agents) will depend on the type of disease to be treated, the type of antibody, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments.

As a general proposition, the therapeutically effective amount of the anti-CD3 antibody administered to human will be in the range of about 0.01 to about 100 mg/kg of patient body weight whether by one or more administrations. In some embodiments, the antibody used is about 0.01 to about 45 mg/kg, about 0.01 to about 40 mg/kg, about 0.01 to about 35 mg/kg, about 0.01 to about 30 mg/kg, about 0.01 to about 25 mg/kg, about 0.01 to about 20 mg/kg, about 0.01 to about 15 mg/kg, about 0.01 to about 10 mg/kg, about 0.01 to about 5 mg/kg, or about 0.01 to about 1 mg/kg administered daily, for example. In one embodiment, an anti-CD3 antibody described herein is administered to a human at a dose of about 100 mg, about 200 mg, about 300 mg, about 400 mg, about 500 mg, about 600 mg, about 700 mg, about 800 mg, about 900 mg, about 1000 mg, about 1100 mg, about 1200 mg, about 1300 mg or about 1400 mg on day 1 of 21-day cycles. The dose may be administered as a single dose or as multiple doses (e.g., 2 or 3 doses), such as infusions. For repeated administrations over several days or longer, depending on the condition, the treatment would generally be sustained until a desired suppression of disease symptoms occurs. One exemplary dosage of the antibody would be in the range from about 0.05 mg/kg to about 10 mg/kg. Thus, one or more doses of about 0.5 mg/kg, 2.0 mg/kg, 4.0 mg/kg, or 10 mg/kg (or any combination thereof) may be administered to the patient. Such doses may be administered intermittently, for example, every week or every three weeks (e.g., such that the patient receives from about two to about twenty, or, for example, about six doses of the anti-CD3 antibody). An initial higher loading dose, followed by one or more lower doses may be administered. The progress of this therapy is easily monitored by conventional techniques and assays.

In some embodiments, the methods may further comprise an additional therapy. The additional therapy may be radiation therapy, surgery, chemotherapy, gene therapy, DNA therapy, viral therapy, RNA therapy, immunotherapy, bone marrow transplantation, nanotherapy, monoclonal antibody therapy, or a combination of the foregoing. The additional therapy may be in the form of adjuvant or neoadjuvant therapy.

In some embodiments, the additional therapy is the administration of small molecule enzymatic inhibitor or anti-metastatic agent. In some embodiments, the additional therapy is the administration of side-effect limiting agents (e.g., agents intended to lessen the occurrence and/or severity of side effects of treatment, such as anti-nausea agents, etc.). In some embodiments, the additional therapy is radiation therapy. In some embodiments, the additional therapy is surgery. In some embodiments, the additional therapy is a combination of radiation therapy and surgery. In some embodiments, the additional therapy is gamma irradiation. In some embodiments, the additional therapy may be a separate administration of one or more of the therapeutic agents described above.

H. Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is an antibody of the invention. The label or package insert indicates that the composition is used for treating the condition of choice. Moreover, the article of manufacture may comprise (a) a first container with a composition contained therein, wherein the composition comprises an antibody of the invention; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

III. Examples

The following are examples of methods and compositions of the invention. It is understood that various other embodiments may be practiced, given the general description provided above.

Example 1. Generation of a Affinity Matured Ant-CD3 Antibody

NNK Library Construction and Panning

To further improve the affinity of the humanized anti-CD3 antibody, 38E4v1 (having HVR-H1 to -H3 and HVR-L1 to -L3 of SEQ ID NOs: 57-62, respectively, and a VH and VL sequence of SEQ ID NOs: 63 and 64), phage libraries were constructed from variant 38E4v1 in Fab-amber format for monovalent Fab phage display with either light chain HVR residues (i.e., HVR-L1, HVR-L2, and HVR-L3) or heavy chain HVR residues (i.e., HVR-H1, HVR-H2, and HVR-H3) randomized using the NNK degenerate codon, which encodes for all 20 amino acids with 32 codons (see, e.g., Brenner et al. *Proc. Natl. Acad. Sci. USA* 89(12): 5381-5383, 1992). Libraries were designed to allow one NNK mutation in each of the three light chain or heavy chain HVRs. The resultant library DNA was electroporated into *E. coli* XL1 cells, yielding approximately $10^9$ transformants.

Phage libraries were incubated in PBS with 1% BSA and 0.05% Tween for 30 minutes and then applied on a CD3ε immobilized plate for first round panning. In the subsequent two rounds, decreased concentrations of biotinylated CD3ε antigen were used with 1000× non-biotinylated CD3ε as competitor in superblock buffer to increase the selection stringency. The phagemids of the third round panning were prepped for deep sequencing analysis.

Deep Sequencing of 38E4v1 Affinity Maturation Libraries

For deep sequencing, phagemid double-stranded DNA was isolated from *E. coli* XL-1 cells carrying phagemid vectors from the initial phage library and the third round of selection. Purified DNA was used as template for a limited cycle PCR-based amplification of VL and VH regions using PHUSION® DNA polymerase (New England Biolabs). PCR products were purified by agarose gel extraction and clean-up (QIAGEN® Gel Extraction Kit). Eluted amplicon DNA was used as the basis for deep sequencing library preparation with standard Illumina library preparation methods, using a TRUSEQ™ DNA Sample Prep kit (Illumina). Adapter-ligated libraries were subjected to a single cycle of PCR and sequenced on the Illumina MISEQ®, using paired-end sequencing with an insert size of 200 bp or 300 bp, as appropriate, to cover the entire length of the amplicon.

Deep Sequencing Analysis of 38E4v1 Affinity Maturation Libraries

Sequencing data were analyzed using the statistical programming language R (see, e.g., R Core Team, R: A language and environment for statistical computing, 2013) and the ShortRead package (see Morgan et al. *Bioinformatics* 25(19): 2607-2608). Quality control was performed on identified HVR sequences. Each HVR sequence was checked for the correct length and was allowed to carry only up to one NNK mutation and no non-NNK mutation. Position weight matrices were generated by calculating the frequency of all mutations of every randomized position.

Enrichment ratios for each mutation were calculated by dividing the frequency of a given mutation at a given position in the sorted sample with the frequency of the very same mutation in the unsorted sample, as described previously (Fowler et al. *Nature Methods* 7(9): 741-746, 2010). The single mutation from the light chain and heavy chain libraries with high enrichment ratio were selected to synthesize to clone into an mammalian Fab expression construct with Flag tag. The plasmids with both heavy and light chain were transfected into 293T cells for 30 ml expression and Fabs were purified using an anti-Flag column.

Fab Affinity Determination by BIACORE® SPR

The binding affinity of selected Fab variants for CD3ε was measured by SPR with a BIACORE® T200 instrument. Briefly, a series S sensor chip CM5 was activated with 1-ethyl-3-(3-dimethylaminopropyl) carbodiimide (EDC) and N-hydroxysuccinimide (NHS) reagents according to the supplier's instructions, and 5 μg/ml CD3ε in 10 mM sodium acetate (pH 4.0) was coupled to achieve 100 response units (RU), except for FC1 (which served as a reference). Unreacted groups were then blocked with 1 M ethanolamine. Next, three-fold serial dilutions of Fab in HBS-P buffer (0.01M HEPES pH 7.4, 0.15M NaCl, 0.005% surfactant P20) from low (0.02 nM) to high (20 nM) were injected (flow rate: 30 μl/min). The binding responses on Fab were corrected by subtracting of RU from a blank flow cell. The sensorgram was recorded and subject to reference and buffer subtraction before evaluating by BIACORE® T200 Evaluation Software (Version 2.0). Association rates ($k_a$) and dissociation rates ($k_d$) were calculated using a simple one-to-one *Langmuir* binding model. The equilibrium dissociation constant ($K_D$) was calculated as the ratio of $k_d/k_a$. The binding affinity kinetics were determined for a high-affinity anti-CD3 Fab, 38E4v11, having the heavy chain and light chain variable domain sequences set forth in FIG. 1. Compared to that of its parent, 38E4v11 displayed more than a 10-fold increase in binding affinity for CD3 (i.e., a greater than 10-fold decrease in $K_D$ compared to 38E4v1) (Table 4).

TABLE 4

38E4v11 binding affinity kinetics relative to 38E4v1

| Sample | $k_a$ (1/M · s) | $k_d$ (1/s) | $K_D$ (nM) |
|---|---|---|---|
| 38E4v11 | $5 \times 10^7$ | $1.6 \times 10^{-3}$ | 0.032 |
| 38E4v1 (parental Fab) | $8.15 \times 10^6$ | $3.17 \times 10^{-3}$ | 0.389 |

Example 2. Generation and Characterization of Exemplary Ly6G6D/CD3 TDBs (Ly6G6D TDBs)

Given the high affinity of 38E4v11 towards CD3, we tested its utility in the context of a T cell-targeting therapeutic antibody, also referred to as a "T cell-dependent bispecific" (TDB) antibody. TDB antibodies are capable of simultaneously binding cell surface antigens on T cells (e.g., CD3) and cell surface antigens on tumor cells, thereby enabling the bound T cells to contribute to the destruction of the tumor cells. However, TDB antibodies directed to a low copy number cell surface antigen target on the surface of tumor cells may exhibit decreased efficacy. Therefore, TDB antibodies having a high-affinity arm directed to a cell surface antigen on T cells, such as CD3, may be particularly useful for pairing with an arm directed to a low copy number target.

To test the utility of the high-affinity 38E4v11 in such a context, we generated a Ly6G6D TDB antibody having one high-affinity arm directed to CD3 (38E4v11) and one arm directed to the cell surface antigen Ly6G6D, which is often expressed in low copy number or inconsistently on the surface of certain tumors (see, e.g., U.S. Pat. No. 7,951,546, which is herein incorporated by reference in its entirety). The Ly6G6D TDBs were produced as full-length antibodies in the knob-into-hole format as human IgG1 (Atwell et al. *J. Mol. Biol.* 270: 26-35, 1997). Half antibodies were expressed in either *E. coli* or Chinese hamster ovary (CHO) cells, purified by Protein A-affinity chromatography, and the proper half antibody pairs were annealed in vitro as described previously (Spiess et al. *Nat. Biotechnol.* 2013). If TDB antibody production was carried out in CHO cells, the antibody included an aglycosylation mutation, for example, at residue N297 (e.g., N297G), such that the TDB antibody was an effector-less variant and unable to initiate antibody-dependent cell-mediated cytotoxicity (ADCC). After annealing, the Ly6G6D TDBs were purified by Hydrophobic Interaction Chromatography (HIC) and characterized by analytical gel filtration, mass spectrometry, and polyacrylamide gel electrophoresis. By these methods, a Ly6G6D TDB having 38E4v11 as its anti-CD3 arm was generated, which is referred to herein as Ly6G6D (38E4v11) TDB. In addition, two other Ly6G6D TDBs, referred to herein as Ly6G6D (40G5c) TDB and Ly6G6D (38E4v1) TDB, which share the same anti-Ly6G6D arm but possess either an anti-CD3 arm 40G5c (having HVR-H1 to -H3 and HVR-L1 to -L3 of SEQ ID NOs: 65-70, respectively, and a VH and VL sequence of SEQ ID NOs: 71 and 72) or an anti-CD3 arm 38E4v1 (described above), respectively, were also generated.

The three Ly6G6D TDBs (Ly6G6D (38E4v11) TDB, Ly6G6D (40G5c) TDB, and Ly6G6D (38E4v1) TDB) were then tested in in vitro cytotoxicity assays and T cell activation assays. For cell killing assays, 15,000 293 cells over-expressing human Ly6G6D antigens (293-Ly6G6D) were first labeled with the cell staining dye carboxyfluorescein succinimidyl ester (CFSE) and incubated with 75,000 human PBMCs as effector cells at a ratio of 5:1 for effector cell: target cell, in the presence of various concentrations of Ly6G6D TDB antibodies for 24 hours. At the end of each assay, live 293 cells were gated out as PI-CFSE+ cells by FACS, and absolute cell count was obtained by flow cytometry. The percentage of cell killing was calculated based on non-TDB treated controls. Compared to the Ly6G6D (40G5c) TDB and Ly6G6D (38E4v1) TDB, the Ly6G6D (38E4v11) TDB displayed enhanced cell killing at lower concentration (FIG. 2).

Figures 3A, 3B:
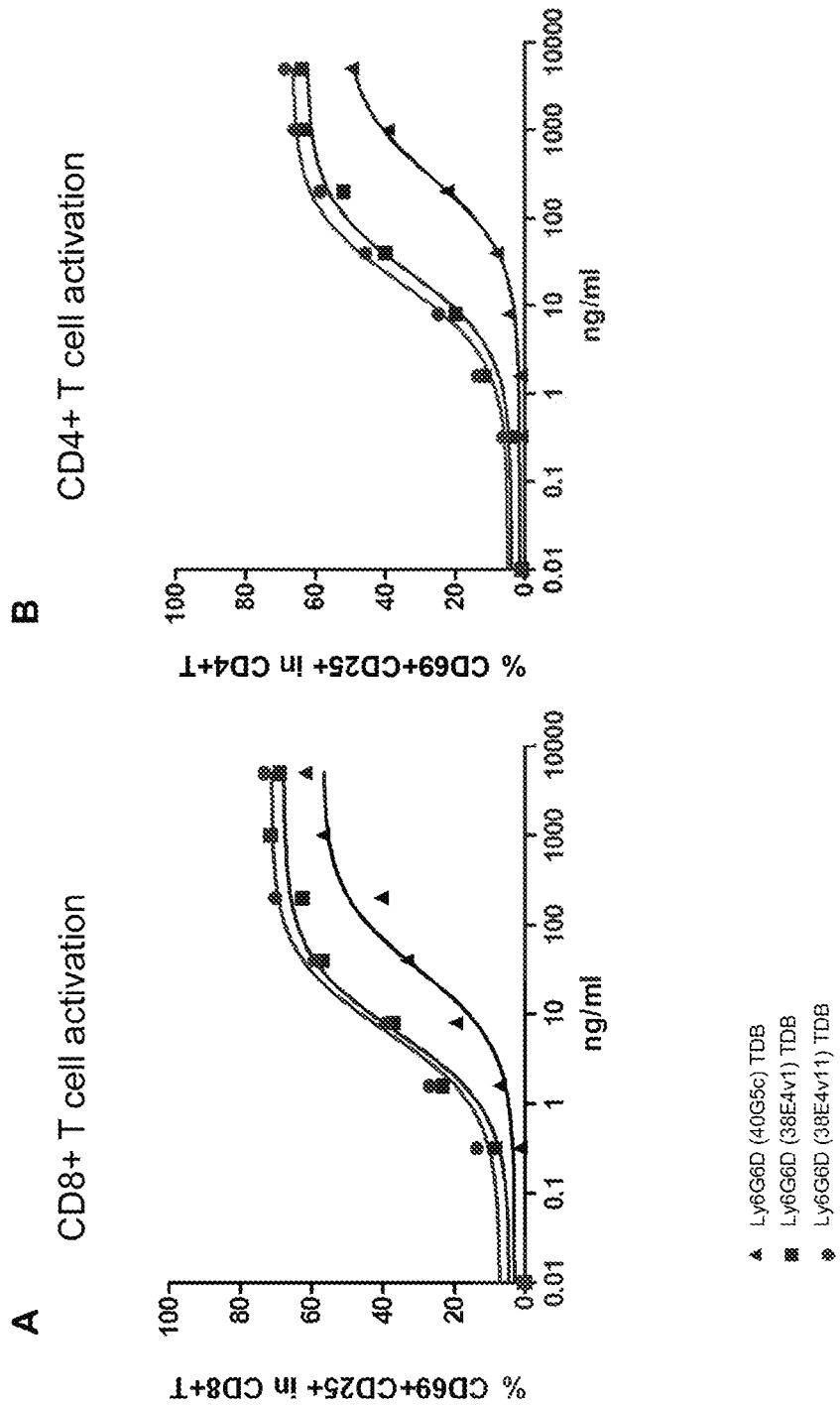
FIG. 3A is a graph showing the percentage of CD69+ CD25+ activated CD8+ T cells as a function of Ly6G6D TDB concentration for three different Ly6G6D TDBs (Ly6G6D (38E4v11) TDB, Ly6G6D (40G5c) TDB, and Ly6G6D (38E4v1) TDB), as assessed by flow cytometry analysis. Effector cell: target cell ratio=5:1.
FIG. 3B is a graph showing the percentage of CD69+ CD25+ activated CD4+ T cells as a function of Ly6G6D TDB concentration for three different Ly6G6D TDBs (Ly6G6D (38E4v11) TDB, Ly6G6D (40G5c) TDB, and Ly6G6D (38E4v1) TDB), as assessed by flow cytometry analysis. Effector cell: target cell ratio=5:1.

When tested for their ability to activate the cytotoxic effects of T cells in in vitro T cell activation assays, the three TDBs again displayed varying efficacy. In the T cell activation assays, the 293-Ly6G6D cells were incubated for 24 hours with human PBMCs were isolated from whole blood of healthy donors by Ficoll separation in the presence of various concentrations of Ly6G6D TDB antibodies, as described above. Activated CD8+ and CD4+ T cells were detected by CD69 and CD25 surface expression by flow cytometry analysis. The Ly6G6D (38E4v11) TDB displayed enhanced efficacy in both CD8+ T cell activation (FIG. 3A) and CD4+ T cell activation (FIG. 3B), compared to the other tested Ly6G6D TDBs, particularly the Ly6G6D (40G5c) TDB, which has a comparatively low binding affinity of 51 nM for CD3.

OTHER EMBODIMENTS

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

What is claimed is:

1. An anti-cluster of differentiation 3 (CD3) antibody, wherein the anti-CD3 antibody comprises a binding domain comprising the following six hypervariable regions (HVRs):
   (a) an HVR-H1 comprising the amino acid sequence of SEQ ID NO: 1;
   (b) an HVR-H2 comprising the amino acid sequence of SEQ ID NO: 2;
   (c) an HVR-H3 comprising the amino acid sequence of SEQ ID NO: 3;
   (d) an HVR-L1 comprising the amino acid sequence of SEQ ID NO: 4;
   (e) an HVR-L2 comprising the amino acid sequence of SEQ ID NO: 5; and
   (f) an HVR-L3 comprising the amino acid sequence of SEQ ID NO: 6; and
   wherein the binding domain comprises (i) a heavy chain variable (VH) domain comprising an amino acid sequence having at least 95% sequence identity to the amino acid sequence of SEQ ID NO: 7; and (ii) a light chain variable (VL) domain comprising an amino acid sequence having at least 95% sequence identity to the amino acid sequence of SEQ ID NO: 8; or (iii) a VH domain as in (i) and a VL domain as in (ii).

2. The anti-CD3 antibody of claim 1, wherein the VH domain comprises the amino acid sequence of SEQ ID NO: 7.

3. The anti-CD3 antibody of claim 1, wherein the VL domain comprises the amino acid sequence of SEQ ID NO: 8.

4. An anti-CD3 antibody, wherein the anti-CD3 antibody comprises a binding domain comprising (a) a VH domain comprising an amino acid sequence of SEQ ID NO: 7 and (b) a VL domain comprising an amino acid sequence of SEQ ID NO: 8.

5. The anti-CD3 antibody of claim 1, wherein the anti-CD3 antibody binds the human CD3ε polypeptide with a $K_D$ of 0.5 nM or lower.

6. The anti-CD3 antibody of claim 5, wherein the anti-CD3 antibody binds the human CD3ε polypeptide with a $K_D$ of 0.3 nM or lower.

7. The anti-CD3 antibody of claim 1, wherein the anti-CD3 antibody binds the human CD3ε polypeptide with a $K_D$ of 0.1 nM or lower.

8. The anti-CD3 antibody of claim 1, wherein the anti-CD3 antibody comprises an Fc region.

9. The anti-CD3 antibody of claim 8, wherein the anti-CD3 antibody comprises a substitution mutation in the Fc region at amino acid residue N297, L234, L235, and/or D265 (EU numbering).

10. The anti-CD3 antibody of claim 9, wherein the substitution mutation is selected from the group consisting of N297G, N297A, L234A, L235A, and D265A.

11. The anti-CD3 antibody of claim 1, wherein the anti-CD3 antibody is monoclonal, humanized, or chimeric.

12. The anti-CD3 antibody of claim 1, wherein the anti-CD3 antibody is an antibody fragment that binds CD3.

13. The anti-CD3 antibody of claim 12, wherein the antibody fragment is selected from the group consisting of Fab, Fab'-SH, Fv, scFv, and (Fab')$_2$ fragments.

14. The anti-CD3 antibody of claim 1, wherein the anti-CD3 antibody is a full-length antibody.

15. The anti-CD3 antibody of claim 1, wherein the anti-CD3 antibody is an IgG antibody.

16. The anti-CD3 antibody of claim 1, wherein the anti-CD3 antibody is a monospecific antibody.

17. The anti-CD3 antibody of claim 1, wherein the anti-CD3 antibody is a multispecific antibody.

18. The anti-CD3 antibody of claim 17, wherein the multispecific antibody is a bispecific antibody.

19. The anti-CD3 antibody of claim 18, wherein the bispecific antibody comprises a second binding domain that binds to a second biological molecule, wherein the second biological molecule is a cell surface antigen on a target cell other than an immune effector cell.

20. The anti-CD3 antibody of claim 19, wherein the cell surface antigen is a tumor antigen.

21. An anti-CD3 antibody, wherein the anti-CD3 antibody is a bispecific antibody that binds to CD3 located on an immune effector cell and a tumor antigen on a target cell other than the immune effector cell, wherein the bispecific antibody comprises an anti-CD3 arm comprising a first binding domain comprising the following six HVRs:
  (a) an HVR-H1 comprising the amino acid sequence of SEQ ID NO: 1;
  (b) an HVR-H2 comprising the amino acid sequence of SEQ ID NO: 2;
  (c) an HVR-H3 comprising the amino acid sequence of SEQ ID NO: 3;
  (d) an HVR-L1 comprising the amino acid sequence of SEQ ID NO: 4;
  (e) an HVR-L2 comprising the amino acid sequence of SEQ ID NO: 5; and
  (f) an HVR-L3 comprising the amino acid sequence of SEQ ID NO: 6; and
an anti-tumor antigen arm comprising a second binding domain.

22. An isolated nucleic acid encoding the anti-CD3 antibody of claim 1.

23. A vector comprising the isolated nucleic acid of claim 22.

24. A host cell comprising the vector of claim 23.

25. A method of producing an anti-CD3 antibody, wherein the anti-CD3 antibody comprises a binding domain comprising the following six HVRs:
  (a) an HVR-H1 comprising the amino acid sequence of SEQ ID NO: 1;
  (b) an HVR-H2 comprising the amino acid sequence of SEQ ID NO: 2;
  (c) an HVR-H3 comprising the amino acid sequence of SEQ ID NO: 3;
  (d) an HVR-L1 comprising the amino acid sequence of SEQ ID NO: 4;
  (e) an HVR-L2 comprising the amino acid sequence of SEQ ID NO: 5; and
  (f) an HVR-L3 comprising the amino acid sequence of SEQ ID NO: 6, and
wherein the method comprises culturing the host cell of claim 24 in a culture medium.

26. An immunoconjugate comprising the anti-CD3 antibody of claim 1 and a cytotoxic agent.

27. A composition comprising the anti-CD3 antibody of claim 1.

* * * * *

UNITED STATES PATENT AND TRADEMARK OFFICE
CERTIFICATE OF CORRECTION

PATENT NO. : 11,007,267 B2
APPLICATION NO. : 15/836107
DATED : May 18, 2021
INVENTOR(S) : Chingwei Vivian Lee et al.

It is certified that error appears in the above-identified patent and that said Letters Patent is hereby corrected as shown below:

In the Specification

Column 12, Line 26, replace "farnesytransferase" with --farnesyltransferase--;
  Lines 44-45, replace "hydroxytamoxfen" with --hydroxytamoxifen--;
  Lines 62-63, replace "r1L-2" with --rIL-2--.

Column 13, Line 24, replace "IgG1, IgG2, IgG3, IgG4" with --$IgG_1$, $IgG_2$, $IgG_3$, $IgG_4$--.

Column 15, Line 7, replace "a Heavy" with --α Heavy--;
  Lines 7-8, replace "p Heavy" with --μ Heavy--.

Column 17, Line 40, replace "ratio 22.0" with --ratio ≥2.0--.

Column 19, Line 58, replace "monoconal" with --monoclonal--.

Column 20, Line 45, replace "PD-" with --PD-1--.

Column 21, Line 32, replace "MED14736" with --MEDI4736--.

Column 24, Line 39, replace "human CD3" with --human CD3ε--;
  Line 42, replace "human CD3" with --human CD3ε--;
  Line 65, replace "a1:1" with --a 1:1--.

Column 25, Line 5, replace "221D" with --22ID--.

Column 26, Lines 64-65, replace "BIACORE®000" with --BIACORE®3000--.

Column 27, Line 38, replace "Pluckthun, in The Pharmacology of Monoclonal Andbodies" with --Pluckthün, in The Pharmacology of Monoclonal Antibodies--.

Signed and Sealed this
Tenth Day of January, 2023

Katherine Kelly Vidal
*Director of the United States Patent and Trademark Office*

CERTIFICATE OF CORRECTION (continued)
U.S. Pat. No. 11,007,267 B2

Column 28, Line 33, replace "83252" with --83:252--.

Column 31, Line 58, replace "1Family" with --1 Family--;
    Line 60, replace "HEL2" with --HEL12--;
    Line 62, replace "Adehyde" with --Aldehyde--.

Column 32, Lines 51-52, replace "ADP-Ribosytransferase" with --ADP-Ribosyltransferase--;
    Line 53, replace "Ribosytransferase" with --Ribosyltransferase--;
    Line 54, replace "Ribosytransferase" with --Ribosyltransferase--;
    Line 55, replace "Ribosytransferase" with --Ribosyltransferase--.

Column 33, Line 8, replace "88 kDa" with --88kDa--;
    Line 29, replace "ICEREL-I11" with --ICEREL-III--;
    Line 64, replace "CDCl27Hs" with --CDC27Hs--.

Column 34, Line 9, replace "CDK41" with --CDK4I--;
    Line 10, replace "P161NK4" with --P16INK4--;
    Line 11, replace "P161NK4A" with --P16INK4A--;
    Line 13, replace "p161NK4A" with --p16INK4A--.

Column 35, Line 14, replace "Class 11" with --Class II--;
    Line 15, replace "DW2.21DR2.2" with --DW2.2/DR2.2--;
    Line 58, replace "S7681" with --S768I--.

Column 36, Line 52, replace "G250 MN" with --G250 (MN--.

Column 37, Line 3, replace "OC15" with --OCI5--;
    Line 10, replace "Protein7" with --Protein17--;
    Line 66, replace "A12A1" with --AI2A1--.

Column 38, Lines 5-6, replace "LDLR-fucosyttransferaseASfusion" with --LDLR-fucosyltransferaseASfusion--.

Column 39, Line 47, replace "Carboxyic" with --Carboxylic--.

Column 40, Line 1, replace "TGF-betaRi1" with --TGF-betaRII--;
    Line 23, replace "STAMP" with --STAMP1--;
    Line 44, replace "16 kDa" with --16kDa--;
    Line 46, replace "16 kDa" with --16kDa--;
    Line 66, replace "(SAGE" with --(SAGE1--.

Column 41, Line 22, replace "Q9U007.1" with --Q9UQ07.1--;
    Line 34, replace "hig" with --hlg--.

Column 42, Line 2, replace "REG-I11" with --REG-III--;
    Line 31, replace "0-Linked" with --O-Linked--;

CERTIFICATE OF CORRECTION (continued)
U.S. Pat. No. 11,007,267 B2

Line 32, replace "0-GLCNAC" with --O-GLCNAC--;
Line 59, replace "Adenylytransferase" with --Adenylyltransferase--;
Line 64, replace "NPTI1b" with --NPTIIb--.

Column 43, Line 16, replace "MUCSAC" with --MUC5AC--;
Line 46, replace "72 kDa Gelatinase, 72 kDa" with --72kDa Gelatinase, 72kDa--;
Line 49, replace "72 kDa Gelatinase, 72 kDa" with --72kDa Gelatinase, 72kDa--.

Column 44, Line 14, replace "99/sequence" with --99% sequence--.

Column 50, Line 29, replace "Table 2under" with --Table 2 under--;
Line 62, replace "le;" with --Ile--.

Column 52, Line 21, replace "glycosyated" with --glycosylated--;
Line 30, replace "1526" with --15:26--.

Column 54, Line 60, replace "24249" with --24:249--.

Column 56, Line 41, replace "Proc. Na." with --Proc. Natl.--;
Line 60, replace "carboxyic" with --carboxylic--.

Column 59, Line 20, replace "acellular" with --a cellular--;
Line 29, replace "2006108052" with --2006/108052--.

Column 61, Line 24, replace "glycosyation" with --glycosylation--;
Line 38, replace "glycosyation" with --glycosylation--;
Line 41, replace "glycosyated" with --glycosylated--.

Column 63, Line 41, replace "Bloorganic" with --Bioorganic--.

Column 64, Line 2, replace "1123" with --I123--;
Line 35, replace "S1AB" with --SIAB--;
Lines 37-38, replace "4-vinysulfone" with --4-vinylsulfone--.

Column 65, Line 33, replace "octadecydimethybenzyl" with --octadecyldimethylbenzyl--.

Column 68, Line 60, replace "Waldenstrom" with --Waldenström--;
Line 61, replace "a Heavy" with --α Heavy--;
Lines 61-62, replace "p Heavy" with --μ Heavy--.

Column 69, Line 50, replace "PD-1" with --PD-L1--.

In the Claims

Column 114, Claim 7, Line 54, replace "of claim 1" with --of claim 6--.